US012295741B2

(12) United States Patent
Trabish et al.

(10) Patent No.: US 12,295,741 B2
(45) Date of Patent: *May 13, 2025

(54) WIRELESS SYSTEM TO POWER A LOW CURRENT DEVICE

(71) Applicant: HOWMEDICA OSTEONICS CORP., Mahwa, NJ (US)

(72) Inventors: Masei Trabish, Folsom, CA (US); Martin Roche, Fort Lauderdale, FL (US); Miro Kang, Yongin-si (KR); YoungCheol Yoon, San Diego, CA (US)

(73) Assignee: HOWMEDICA OSTEONICS CORP., Mahwa, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/343,596

(22) Filed: Jun. 28, 2023

(65) Prior Publication Data

US 2023/0337972 A1   Oct. 26, 2023

Related U.S. Application Data

(63) Continuation of application No. 16/913,233, filed on Jun. 26, 2020, now Pat. No. 11,723,594.
(Continued)

(51) Int. Cl.
*H01Q 1/24* (2006.01)
*A61B 5/00* (2006.01)
(Continued)

(52) U.S. Cl.
CPC .......... *A61B 5/4848* (2013.01); *A61B 5/0004* (2013.01); *A61B 5/0022* (2013.01);
(Continued)

(58) Field of Classification Search
CPC ............ A61B 17/8695; A61B 2505/05; A61B 2505/09; A61B 2560/0214;
(Continued)

(56) References Cited

U.S. PATENT DOCUMENTS 7,084,605 B2   8/2006   Mickle et al.
7,400,253 B2   7/2008   Cohen
(Continued)

*Primary Examiner* — Tho G Phan
(74) *Attorney, Agent, or Firm* — Bookoff McAndrews, PLLC

(57) ABSTRACT

A wireless system comprising a first wireless device and a second wireless device. The first wireless device is configured to operate with less than 15 milliamperes of current. The second wireless device has an internal power source and is configured to transmit one or more radio frequency signals to the first wireless device. The first wireless device is configured to receive the one or more radio frequency signals from the second wireless device. The first wireless device is configured to harvest energy from the one or more radio frequency signals. The first wireless device is enabled for operation after a predetermined amount of energy is harvested from the one or more radio frequency signals. A communication handshake occurs between the first and second wireless devices to indicate that the first wireless device is in communication with the second wireless device. The first wireless device is configured to perform at least one task from harvested energy.

20 Claims, 29 Drawing Sheets

Related U.S. Application Data

(60) Provisional application No. 62/868,621, filed on Jun. 28, 2019.

(51) Int. Cl.

| | |
|---|---|
| *A61B 5/01* | (2006.01) |
| *A61B 5/024* | (2006.01) |
| *A61B 5/07* | (2006.01) |
| *A61B 5/11* | (2006.01) |
| *A61B 5/145* | (2006.01) |
| *A61B 5/22* | (2006.01) |
| *A61B 5/282* | (2021.01) |
| *A61F 2/46* | (2006.01) |
| *A61F 13/00* | (2006.01) |
| *G16H 20/30* | (2018.01) |
| *H01Q 5/10* | (2015.01) |
| *H02J 7/00* | (2006.01) |
| *H02J 50/20* | (2016.01) |
| *A61B 17/86* | (2006.01) |
| *A61F 2/30* | (2006.01) |

(52) U.S. Cl.
CPC .......... *A61B 5/0031* (2013.01); *A61B 5/0077* (2013.01); *A61B 5/01* (2013.01); *A61B 5/02427* (2013.01); *A61B 5/076* (2013.01); *A61B 5/1114* (2013.01); *A61B 5/112* (2013.01); *A61B 5/1121* (2013.01); *A61B 5/14539* (2013.01); *A61B 5/224* (2013.01); *A61B 5/282* (2021.01); *A61B 5/4023* (2013.01); *A61B 5/4533* (2013.01); *A61B 5/4585* (2013.01); *A61B 5/4836* (2013.01); *A61B 5/4851* (2013.01); *A61B 5/6812* (2013.01); *A61B 5/6833* (2013.01); *A61B 5/6844* (2013.01); *A61B 5/686* (2013.01); *A61B 5/6878* (2013.01); *A61B 5/6882* (2013.01); *A61B 5/742* (2013.01); *A61B 5/746* (2013.01); *A61F 2/4657* (2013.01); *A61F 13/00051* (2013.01); *G16H 20/30* (2018.01); *H01Q 1/248* (2013.01); *H01Q 5/10* (2015.01); *H02J 50/20* (2016.02); *A61B 5/4566* (2013.01); *A61B 5/4571* (2013.01); *A61B 5/6817* (2013.01); *A61B 5/6832* (2013.01); *A61B 5/6839* (2013.01); *A61B 17/8695* (2013.01); *A61B 2505/05* (2013.01); *A61B 2505/09* (2013.01); *A61B 2560/0214* (2013.01); *A61B 2560/0219* (2013.01); *A61B 2560/0247* (2013.01); *A61B 2562/0219* (2013.01); *A61B 2562/0247* (2013.01); *A61B 2562/028* (2013.01); *A61B 2562/166* (2013.01); *A61F 2002/3067* (2013.01)

(58) Field of Classification Search
CPC .... A61B 2560/0219; A61B 2560/0247; A61B 2562/0219; A61B 2562/0247; A61B 2562/028; A61B 2562/166; A61B 5/00; A61B 5/0004; A61B 5/002; A61B 5/0022; A61B 5/0031; A61B 5/0077; A61B 5/01; A61B 5/02427; A61B 5/076; A61B 5/11; A61B 5/1114; A61B 5/112; A61B 5/1121; A61B 5/14539; A61B 5/224; A61B 5/4023; A61B 5/4533; A61B 5/4566; A61B 5/4571; A61B 5/4585; A61B 5/4836; A61B 5/4848; A61B 5/4851; A61B 5/6812; A61B 5/6817; A61B 5/6828; A61B 5/6831; A61B 5/6832; A61B 5/6833; A61B 5/6839; A61B 5/6844; A61B 5/686; A61B 5/6882; A61B 5/742; A61B 5/746; A61B 5/282; A61B 5/6878; A61F 13/00051; A61F 2/4657; A61F 2002/3067; G16H 20/30; H01Q 1/248; H01Q 1/27; H01Q 5/10; H01Q 11/12; H02J 7/00; H02J 17/00; H02J 50/20

See application file for complete search history.

(56) References Cited

U.S. PATENT DOCUMENTS

| | | | |
|---|---|---|---|
| 7,719,416 B2 | 5/2010 | Arms et al. | |
| 8,621,245 B2 | 12/2013 | Shearer et al. | |
| 8,849,223 B2 | 9/2014 | Pennisi | |
| 9,101,777 B2 | 8/2015 | John | |
| 9,232,475 B2 | 1/2016 | Heinzelman et al. | |
| 9,314,159 B2* | 4/2016 | Lyon | A61B 5/0205 |
| 9,318,921 B2 | 4/2016 | Abu-Qahouq | |
| 10,396,586 B1 | 8/2019 | Chen | |
| 11,038,262 B2 | 6/2021 | Yehezkely | |
| 11,123,014 B2 | 9/2021 | Apperson et al. | |
| 11,504,061 B2* | 11/2022 | Apperson | A61B 5/6833 |
| 11,689,053 B2* | 6/2023 | Yehezkely | G06K 19/07773 307/104 |
| 11,723,594 B2* | 8/2023 | Trabish | A61B 5/112 607/60 |
| 2005/0146220 A1 | 7/2005 | Hamel et al. | |
| 2009/0102296 A1 | 4/2009 | Greene et al. | |
| 2011/0213208 A1 | 9/2011 | McKenna et al. | |
| 2012/0013296 A1 | 1/2012 | Heydari et al. | |
| 2012/0106103 A1 | 5/2012 | Nohra | |
| 2014/0011543 A1 | 1/2014 | Li et al. | |
| 2014/0070935 A1 | 3/2014 | Wang et al. | |
| 2015/0201342 A1 | 7/2015 | Vannithamby | |
| 2016/0134150 A1 | 5/2016 | Chen et al. | |
| 2020/0405227 A1 | 12/2020 | Trabish et al. | |
| 2021/0288395 A1* | 9/2021 | Yehezkely | H04W 4/70 |
| 2022/0087598 A1 | 3/2022 | Pazicsnyek | |

* cited by examiner

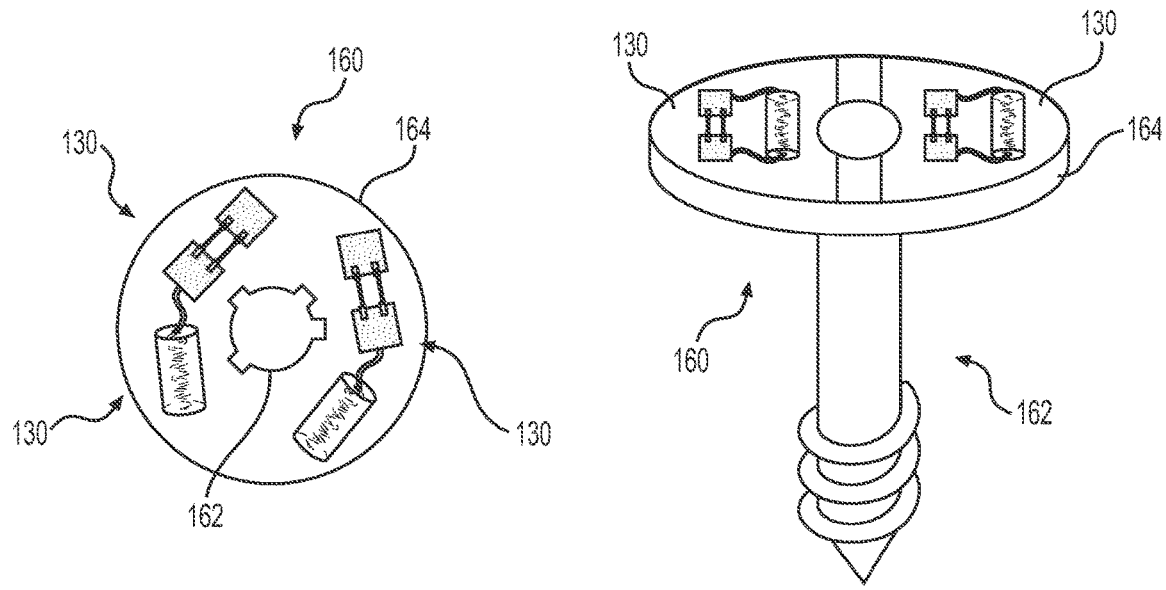
FIG. 4A  FIG. 4B
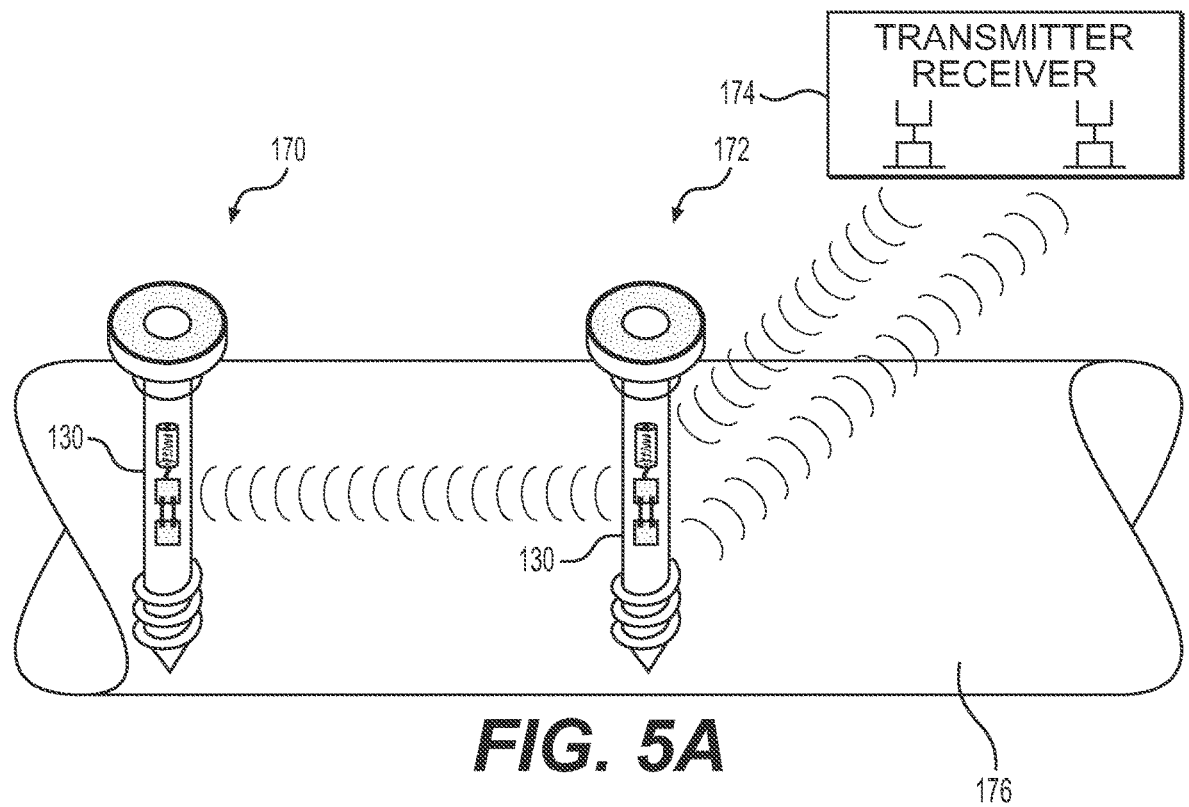
FIG. 5A

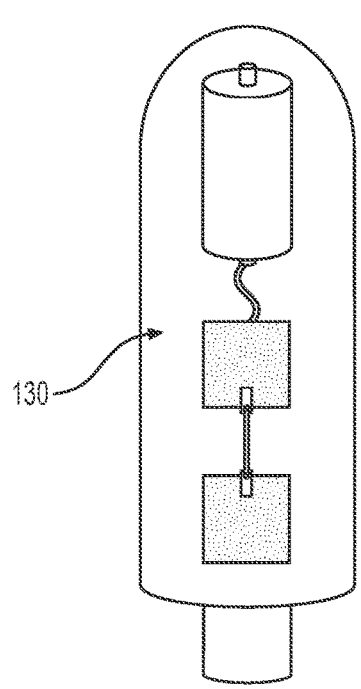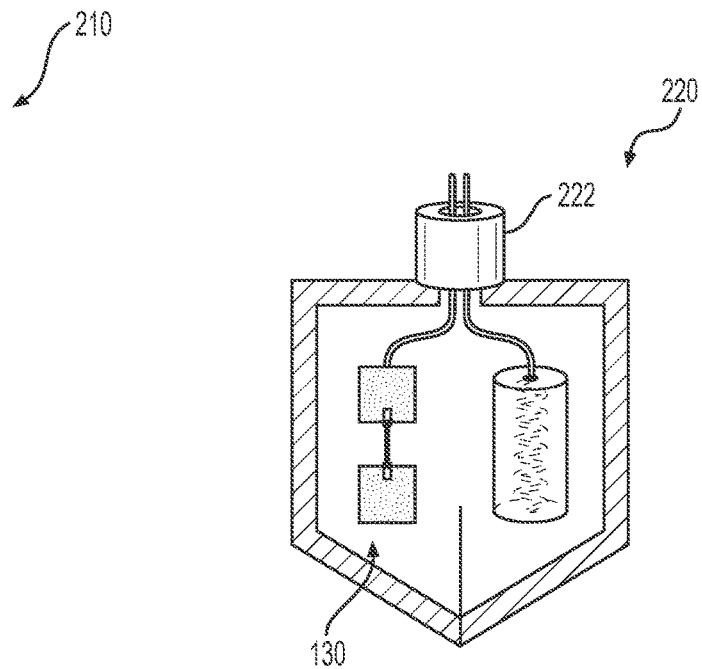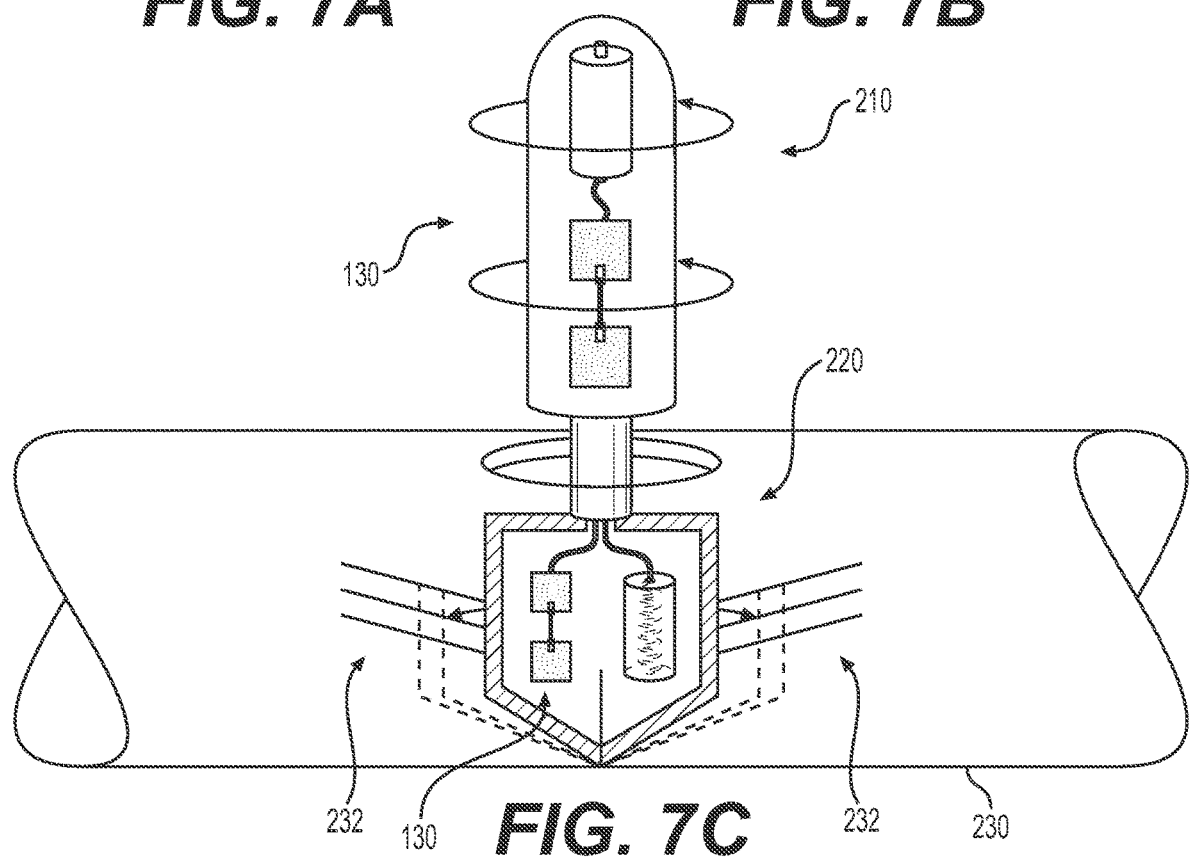

| Layer | Thickness (mil) |
|---|---|
| AIR | |
| PREPREG(DS-7402 1067) | 1.574 |
| PREPREG(BSH-MX-13MP) | 0.512 |
| CU PLATING | 0.472 |
| CU 1OZ(AR8515R) | 1.338 |
| POLYNIDE(AR7165R) | 1.968 |
| LF0111 BOND PLY | 5.906 |
| POLYNIDE(AR7165R) | 1.968 |
| CU 1OZ(AR8515R) | 1.338 |
| CU PLATING | 0.472 |
| PREPREG(BSH-MX-13MP) | 0.512 |
| PREPREG(DS-7402 1067) | 1.574 |
| AIR | |

THICKNESS 17.634mil

PICK GAIN: 2.0 dBi
AVERAGE GAIN -2dBi
EFFICIENCY: 56%

WIRELESS SYSTEM TO POWER A LOW CURRENT DEVICE

CROSS-REFERENCE TO RELATED APPLICATION(S)

This patent application is a continuation of and claims the benefit of priority to U.S. application Ser. No. 16/913,233, filed on Jun. 26, 2020, which claims the benefit to U.S. Provisional Application No. 62/868,621, filed Jun. 28, 2019, all of which are incorporated herein by reference in their entireties.

FIELD

The present invention pertains generally to medical devices, and particularly to, but not exclusively to, an orthopedic system for generating measurement data to assess a musculoskeletal system.

BACKGROUND

Wireless technology has advanced significantly in recent years. Different types of wireless technology are ubiquitous having industry standards that allow companies to use the communication technology seamlessly. Wireless standards such as WiFi, Bluetooth, WiMax, Zigbee, Wireless Mesh Networks, and Cell phone standards are available and integrated in many commonly used devices. People using wireless devices can be in areas of high signal traffic with different networks in communication with devices. For example, a home can have cell phone coverage, a wireless local network, a WiFi hot spot, Bluetooth connections, Zigbee connections, and others. Thus, the home can have access to many different radio frequency signals in different frequency bands for interconnection. It should be noted that many devices connect to a wireless device via a wired connection. Some of these devices require a current "low current" less than 15 milliamperes for operation. It would be of great benefit if these "low current" devices could be mad wireless at low cost.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIG. 4A is an illustration of a top view of a washer system in accordance with an example embodiment;

FIG. 4B is a lateral view of the washer system in accordance with an example embodiment;

FIG. 5A is an illustration of a plurality of smart screws configured to communicate to a computer in accordance with an example embodiment;

FIG. 7A is an illustration of a handle in accordance with an example embodiment;

FIG. 7B is an illustration of a percutaneous screw in accordance with an example embodiment;

FIG. 7C is an illustration of the handle coupled to the percutaneous screw in accordance with an example embodiment;

FIG. 20 is a list of specifications for the antennae of FIG. 19 in accordance with an example embodiment;

DETAILED DESCRIPTION

Figure 1A:
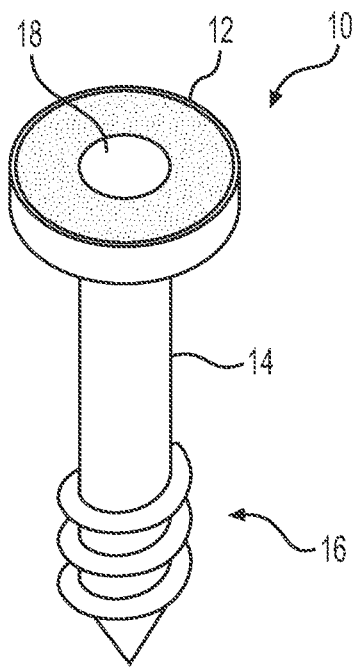
FIG. 1A is an illustration of a smart screw in accordance with an example embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the device are illustrative only and do not limit use for other parts of a body or for other applications. The device is used to measure at least parameter to generate quantitative measurement data. The devices disclosed herein below are configured to support health, healing, and generate quantitative measurement data related to the human body. In one embodiment, the device is configured to couple to a musculoskeletal system is used on the knee, hip, ankle, spine, shoulder, hand, wrist, foot, fingers, toes, bone, muscle, ligaments tendon and other areas of the musculoskeletal system. Although one or more examples may describe use on the musculoskeletal system the principles disclosed herein are meant to be adapted for use to all locations on or within the human body. The following description of embodiment(s) is merely illustrative in nature and is in no way intended to limit the invention, its application, or uses.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device. The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging, accelerometer, magnetometer, gyroscope, inclinometers, or MEMs devices) can be used within the scope of the embodiments described.

At least one embodiment is directed to a kinetic orthopedic measurement system that is configured to measure motion and position. The measurement system can be used in surgery to determine real time alignment, range of motion, loading, impingement, and contact point of orthopedic implants. Although the system is generic to any orthopedic assessment, pre-operative measurement, surgery, rehabilitation, or long-term monitoring (e.g., spinal, shoulder, knee, hip, ankle, wrist, finger, toe, bone, musculoskeletal, etc.) the following examples deal with the use in the orthopedic field as a non-limiting example of an embodiment of the invention.

The non-limiting embodiment described herein is related to quantitative measurement used for orthopedic assessment and referred to herein as the kinetic system. The kinetic system includes a sensor system that provides quantitative measurement data and feedback that can be provided visually, audibly, or haptically to a patient, doctor, medical staff, therapist, surgeon or surgical team. The kinetic system provides real-time dynamic data regarding sensor information and position information related to the musculoskeletal system.

In general, kinetics is the study of the effect of forces upon the motion of a body or system of bodies. Disclosed herein is a system for kinetic assessment of the musculoskeletal system. The kinetic system can be for monitoring and assessment of the musculoskeletal system or installed prosthetic components coupled to the musculoskeletal system. For example, installation of a prosthetic component can require one or more bone surfaces to be prepared to receive a device or component. The kinetic system is designed to take quantitative measurements related to movement of one or more bones of the musculoskeletal system, take measurements from one or more sensors to monitor health, or provide therapy to support healing. The sensors are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled. In one embodiment, one or more screws can be implanted in one or more bones to provide measurement data. Alternatively, one or more sensors can be coupled to the skin as a flexible patch. In one embodiment, the implanted screws can be in communication with the implanted screws as a system working together to in a specific application.

A prosthetic joint installation can benefit from quantitative measurement data in conjunction with subjective feedback of the prosthetic joint to the surgeon. Pre-operative measurement data can be collected to provide a pathology of a patient and set expectations and outcomes from a surgical or prosthetic component solution. The quantitative measurements can be used to determine adjustments to bone, prosthetic components, or tissue prior to final installation. Permanent sensors can also be housed in final prosthetic components to provide periodic data related to the status of the implant. Data collected intra-operatively and long term can be used to determine parameter ranges for surgical installation and to improve future prosthetic components. One or more sensors used post-operatively can be used to monitor motion of the musculoskeletal system to determine how the repair is performing and provide feedback based on quantitative measurement data. The physical parameter or parameters of interest can include, but are not limited to, measurement of alignment, load, force, pressure, position, displacement, density, viscosity, pH, spurious accelerations, color, movement, chemical composition, particulate matter, structural integrity, and localized temperature. Often, several measured parameters are used to make a quantitative assessment. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, equipment, or other physical system.

At least one embodiment is directed to a system for adjusting or monitoring position of the musculoskeletal system for stability, alignment, balance, and range of motion. Examples of monitoring can comprise: a prosthetic component configured to rotate after being coupled to a bone; a sensed prosthesis having an articular surface where the sensed prosthesis is configured to couple to a second prosthetic component, the sensed prosthesis has a plurality of load sensors coupled to the articular surface and a position measurement system configured to measure position, slope, rotation, or trajectory, a remote system configured to wirelessly receive quantitative measurement data from the sensed prosthesis where the remote system is configured to display the articular surface, where the remote system is configured to display position of applied load to the articular surface, and where the remote system is configured to report impingement as the musculoskeletal joint is moved through a range of motion (ROM).

Embodiments of the invention are broadly directed to measurement of physical parameters. Many physical parameters of interest within physical systems or bodies can be measured by evaluating changes in the characteristics of energy waves or pulses. As one example, changes in the transit time or shape of an energy wave or pulse propagating through a changing medium can be measured to determine the forces acting on the medium and causing the changes. The propagation velocity of the energy waves or pulses in the medium is affected by physical changes in of the medium. The physical parameter or parameters of interest can include, but are not limited to, measurement of load, force, pressure, displacement, density, viscosity, localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, appliance, vehicle, equipment, or other physical system.

In all of the examples illustrated and discussed herein, any specific materials, temperatures, times, energies etc. . . . for process steps or specific structure implementations should be interpreted to be illustrative only and non-limiting. Processes, techniques, apparatus, and materials as known by one of ordinary skill in the art may not be discussed in detail but are intended to be part of an enabling description where appropriate.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

In the present invention these parameters are measured with an integrated wireless sensing module or device comprising an i) encapsulating structure that supports sensors and contacting surfaces and ii) an electronic assemblage that integrates a power supply, sensing elements, ultrasound resonator or resonators or transducer or transducers, an accelerometer, antennas and electronic circuitry that processes measurement data as well as controls all operations of energy conversion, propagation, and detection and wireless communications. The wireless sensing module or device can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

One type of orthopedic screw is an ACL (Anterior Cruciate Ligament) screw. One or more ACL screws are placed during ACL reconstruction to stabilize the ligament in the femur and in the proximal tibia. The hardware can be a metal based interference screw such as titanium, plastic such as PEEK, or bio-absorbable. A screw is placed during surgery and typically is not removed even after healing unless a failure, soft tissue impingement, or reconstructive implants require removal of the screw. A smart screw is a screw that houses micro-electronics that performs one or more functions. In one embodiment, the smart screw is used during surgery to aid in screw placement and screw graft stabilization.

A smart screw intra-operative system can incorporate microelectronic integration into an arthroscopic system. There is a need for appropriate tunnel placement in the tibia and femur to support healing and post-operative function. Problems can occur if the graft is placed inappropriately causing impingement, pain limited range of motion, and graft failure. In one embodiment, the surgeon can place a small smart tack (fiducial) in the intra-articular non-loaded area of the femur and one in the tibia. The arthroscope utilizing optics, registers the fiducials relative to the femoral and tibial bone model of the patient. A pre-operative MRI can be utilized or an intra-operative ultra-scan to register femur and tibia to the optical system. In the example, the smart screw will have IMU (inertial measurement unit) electronics will be referenced from the fiducials and tracked along their insertion path, to define depth and angles of the smart screw placement. The smart screw or a device can include one or more MEMs (micro-electro-mechanical systems) devices, a camera, or video device. The device can be tool used in conjunction with the screw. The smart screw as it is being inserted will measure the torque required and confirm that the screw is securely stabilized. In the example, measurement data from the screw or device can be transmitted to a computer having a display to provide the measurement data in real-time.

Once the smart screws are placed in the tibia and femur, they are zeroed relative to gravity and each other. The knee is taken through a full ROM, full extension, and defined flexion is recorded by the system. Measurement data related to rotation and dynamic stresses related to translation are now recorded by the system. An anterior-posterior drawer is performed where the knee is flexed 90 degrees and a force applied to the tibia in the posterior and then in the anterior direction. The translation and displacement of the knee is recorded relative to the at least two smart screws. A Lachman Test can also be performed where the knee is flexed 20 degrees and the tibia is pulled forward to assess the amount of anterior motion of the tibia to define ACL stability. Similarly, medial-lateral forces can be applied at 20 degrees to define collateral ligament stability.

The smart screws are also used for post-operative monitoring. First, the smart screws can be used to identify if the patient post-operative therapy is progressing appropriately. In one embodiment, the patient is discharged with crutches and a brace. Physical Therapy is instituted within several days of surgery. Limited weight bearing is controlled to protect the ACL until interval healing has occurred and the patient's quadriceps function and knee stability has returned. The knee is monitored for infection and resolution of swelling and inflammation. Compliance to the prescribed post-op regimen can be monitored. An exercise regimen can be sent to the patient's phone and the smart screws activated to monitor that the patient is following protocol and remains in a "safe" healing zone. The knee brace can house the near field energy source to energize the electronics, and the knee function can then be interrogated.

Placement of the smart screws in the femur and tibia are used to describe knee function. For example, the smart screws can monitor and measure ROM (range of motion) relative to gravity and Femur to Tibia. The smart screws can be used to measure quadriceps strength and torque with a defined extension maneuver with applied resistance. Gait mechanics such as stride, cadence, activity, steps and other movement can be monitored by the smart screws. As previously mentioned, the Lachman test can be monitored by the smart screws by measuring anterior motion of the tibia in a predetermined movement of the tibia in relation to the femur. Another test that generates quantitative measurement data from the smart screws is an anterior-posterior drawer. The knee is flexed 90 degrees and a force is applied to the tibia in the posterior. The anterior direction translation and displacement of the knee is measured and recorded relative to the smart screws. All of the above quantitative measurement data is used to support assessment of the patient post-operatively. The measurement data can indicate if adjustments to the therapy are required and the status of the implanted prosthetic components.

In the example of a knee joint, the quantitative measurement data from the smart screws can indicate stable knee function. The patient can then be released from using crutches and later bracing can be considered to support the knee joint for optimal operation. The effects of the therapy program using the smart screws can be linked to knee function and a patient can be educated on their recovery relative to a plan and other patients. In one embodiment, when the smart screw is activated, the data will be transmitted (RF/Bluetooth) to a patient recovery application. In one embodiment, the application can be on a computer or a device such as a smart phone. The quantitative measurement data from the smart screws will be uploaded into a cloud based VPN (virtual private network) that is HIPPA Compliant. The quantitative measurement data can be assessed by one or more computer programs and updates, work flows, and the measurement data can be sent to the treating physician and health care team. The smart screws can be used to support post-op exercises, treatment, or pharmaceuticals that can accelerate the healing phase. Furthermore, different ACL reconstruction techniques can be compared with real-time data. Evaluations of the effects of ACL reconstruction when combined with multi ligamentous injuries can also be analyzed. Healing phase monitoring related to graft adherence to the host tunnels (bone to bone, tendon to bone, composite to bone) can provide quantitative measurement data related thereto. Other important parameters can also be generated such as improving ROM and terminal extension, achieving improved muscle strength, improved proprioception, improved stability, and improved gait mechanics.

The smart screws can also be used to determine when the "patient" is healed. For example, quantitative measurement data from the smart screws can be used to determine if an ACL is healed so that the patient can return to high intensity activities. Presently, a patient exam is often used after a predetermined time after surgery to release a patient to sports. The patient exam is a subjective examination that can vary from significantly between surgeons and doctors. There is very little objective data that is utilized to define when functional healing has occurred. A quantitative functional knee exam can be performed with the activated smart screws relaying the information in real-time. Further evaluation, can be assessed while the patient is placed in a walking regimen, then a running regimen, followed to sports related acceleration—deceleration activities where data is being generated by the smart screws. In one embodiment, the smart screws will send data related to the knee function to a data base for evaluation by one or more programs that use the quantitative measurement data to provide a functional knee determination based on measurement data of a healed functional knee that can be used with a subjective examination.

The smart screws can also be used to evaluate post-operative exercises, post-operative treatment, or pharmaceuticals where measurement data provides evidence of the efficacy of the different treatments. Different techniques to reconstruct the musculoskeletal system can also be evaluated. For example, different ACL reconstruction techniques can be compared with real-time data to evaluate the effects of ACL reconstruction when combined with multi ligamentous injuries. In one embodiment, the healing phase monitoring is related to the graft adherence to the host tunnels such as bone to bone, tendon to bone, or composite to bone. Other important parameters can also be monitored to see the efficacy of the treatments to improve range of motion, terminal extension, muscle strength, improved proprioception, improved stability, or improved gait mechanics.

The smart screws can also be used for long term monitoring. An extreme example is an athlete returning back to a sport. For example, a knee joint can be monitored for skeletal knee stability related to strength. The torque and range of motion can be monitored during specific training or activities that are deemed essential. The measurement data can be analyzed from the smart screws that lead to specific interventions that can be utilized if knee stability is decompensating. Furthermore if the athlete fells that a sprain or injury occurred and wants to continue playing, the screw can be activated and the knee mechanics and kinetics of the leg and joint can be evaluated. Although the example is a knee joint it should be noted that the use of smart screws can be used for any joint or part of the musculoskeletal system.

As previously mentioned, there are many different types of sensors that can be utilized within a smart screw. In one embodiment, the smart screws can be used for the treatment of disease or apply a treatment or drug. For example, the smart screw can include an ultrasonic sensor that can be utilized to generate frequencies to aid in healing through blood flow modulation, and osteoplastic induction. The smart screw has the ability for in vivo monitoring of multiple parameters with multiple sensors. The stability of the screw smart implantation can be monitored to measure local bone softening due to blood flow and final healing of graft. The stability of a joint related to motion, rotation, translation, and range of motion. From a macro perspective, the smart screws can be used to monitor the musculoskeletal system to provide measurement data related to joint mechanics as muscle strength changes, gait mechanics, compliance to rehabilitation program (frequency, effort, protection), general activity, patient directed interrogation of the musculoskeletal system, and physician interrogation of the musculoskeletal system related to a joint, rehabilitation, and sports.

As shown herein above, smart screws can be placed in the femur and tibia to provide quantitative measurement data that can be used in a variety of ways to assess the musculoskeletal system and more specifically a knee joint replacement and subsequent rehabilitation of the leg. In general, smart screws will be used in the sports medicine to assess the musculoskeletal system, repair, and rehabilitate using quantitative measurement data. The measurement data on the knee, hip, and rotator cuff, shoulder, and other musculoskeletal repairs can be used to ensure that the subject is prepared and ready for sustained physical activity.

Smart screws can be used in trauma applications such as hip-pelvis, spine, and extremity fractures. Hip fractures can be stabilized with a screw attached to a rod or plate. The smart screw can aid in providing measurement data related to the internal stability of the bone when placing the screw. Post-operatively, the smart screw can be used to monitor healing of the fracture. The smart screw will house microelectronics, sensors, communication circuitry, and logic to control a measurement process. In one embodiment, the smart screw will include micro-motion related sensors. Signals can be sent through the fracture side to be detected by micro-motion sensors to determine the effects of weight bearing on the fracture. Surgeons can refine the patient's post-operative activities and gait mechanics during the healing process. Moreover, the surgeon or doctor can assure the patient with quantitative measurement data related to their progress and send activity strengthening exercises related to gait or strength to meet the need of the patient.

The smart screws can be used to detect motion at an implant to bone interface or bone to bone interface. For example, smart screws can be used to detect motion in the spine between an implant and vertebra interface. In spinal surgery, implants such as inter-body fusion cages and disc replacement prostheses are often used. In most fusion or corrective spinal procedures, pedicle screws are used. Spinal pain following fusions, disc replacements, and other procedures can stem from persistent motion at what should be a stable interface. In certain instances a surgeon wants the ability to detect motion at an implant or bone interface. An example of movement is when a spinal segment is fused; the forces are then transferred to the surrounding soft tissue and vertebral levels above and below. Proximal Junctional Kyphosis, is where the spinal segment above and/or below the fused segment becomes unstable can occur asymptomatically. Further surgery may be required when symptoms occur, to stabilize the segment. This can occur continuously throughout the patient's life. Currently, it is difficult to identify the cause of significant post-operative spinal pain. Abnormal motion is currently evaluated by standard and dynamic motion X-rays, and nuclear imaging. Presently there is no accurate way to confirm abnormal motion at these interfaces with a high sensitivity and specificity. Moreover, a surgeon desires the ability to avoid surgical exploration of the fusion or disc implant site to confirm abnormal motion.

The smart screw is an implantable sensor system that is applied at the bone-implant surface. Since a spinal fusion requires integration of the "cage" or spinal instrumentation into the fusion mass, a sensor that is incorporated into the "cage" or instrumented elements can detect motion. In non-instrumented fusions, the sensors can be implanted into the bony elements at specific locations to detect abnormal motion post-operatively. In one embodiment, a spinal implant such as the smart screw is inserted into the pedicle of a spinal bone. The smart screw will house the microelectronics. The smart screw is activated with one or more sensors that measures position in 3D space and trajectory such that the smart screw can be guided into appropriate angles and depth within bone. The smart screw will be placed then tested for stability and torque to confirm the smart screw is fully seated. Each spinal segment will house at least 2 smart screws and one smart screw can be placed into the spinal segment above and below the surgical segments. Post-operatively, the sensors in each smart screw can be activated or powered by an external mechanism. For example power can be provided inductively or by radio frequency signals to provide power that enables the smart screws for providing quantitative measurement data. A capacitor or energy storage device can store the energy for use at a later time period or when activated. Power management circuitry can be used to reduce energy consumption. Alternatively, the smart screw could house an energy source such as a battery. Once the smart screws are activated, the patient would flex, extend, rotate and load the sensors in the smart screws at variable positions. In one embodiment, the sensor information would be transmitted from the smart screws and received by an external computer with a display. The computer can include software to analyze the quantitative measurement data, display the measurement data, or the measurement data can be translated in a graphic form to support rapid assimilation of the information. The surgeon can now document the amount of motion and load at a fusion site or disc implant interface. The parameters of micro-motion would then be evaluated. In one embodiment, the computer can produce a work flow to correct the issue based on the measurement data. In general, the relative motion and the angular changes between the smart screws would be monitored. The patient activities can be modified or the segment stabilized with micro invasive approaches that are minimally invasive if abnormal motion at the surrounding segments is detected. The same technology can be used in a cage or an artificial disc motion implant.

FIG. 1A is an illustration of a smart screw 10 in accordance with an example embodiment. Smart screw 10 is configured to house electronic circuitry and sensors having a form factor that can be used within the musculoskeletal system. The electronic circuitry is configured to transmit measurement data and control a measurement process of the sensors. Smart screw 10 comprises a screw head 12, a shaft 14, and threads 16. In one embodiment, electronic circuitry and sensors can be placed within the screw head 12. A region 18 of smart screw 10 is designed to engage with a bit of a screw gun for screwing smart screw 10 into the musculoskeletal system. The region 18 can be patterned similar to conventional screws having a slot, cross slots, hex key, or other systems to engage a screw gun for securing smart screw 10 to the musculoskeletal system. Threads 16 are used to securely fasten smart screw 10 to the musculoskeletal system such that smart screw 10 will not loosen under normal use of the musculoskeletal system. In one embodiment, threads 16 will securely fasten to bone if the bone integrity is not compromised. The screw gun or smart screw 10 can have one or more sensors that determine stability of smart screw 10 when fastened to the musculoskeletal system.

Figure 1B:
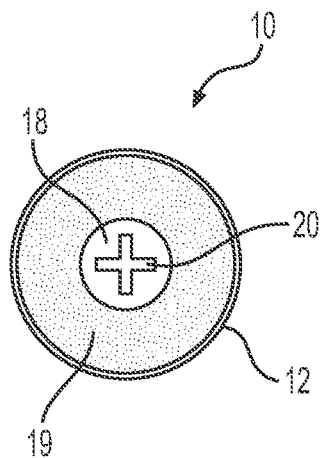
FIG. 1B is a top view of the smart screw in accordance with an example embodiment.

FIG. 1B is a top view of smart screw 10 in accordance with an example embodiment. Region 18 illustrates cross slots or a Phillips type coupling. In one embodiment, screw head 12 has a cavity for housing electronic circuitry and one or more sensors. In one embodiment, cap 19 is removable to support installation of the electronic circuitry and one or more sensors. Cap 19 is then fastened to form screw head 12 such that the electronic circuitry and one or more sensors are hermetically sealed within screw head 12. Alternatively, region 18 can be removed thereby exposing the underlying cavity for housing electronic circuitry and one or more sensors. Region 18 can couple to and seal to cap 19 to enclose smart screw 10. In one embodiment, the electronic circuitry and sensors can be potted within the cavity with screw head 12 and cap 19 is mechanically engaged and sealed. In one embodiment, a glue, adhesive, or sealing material can be used in conjunction with cap 19 to form the hermetic seal.

Figure 1C:
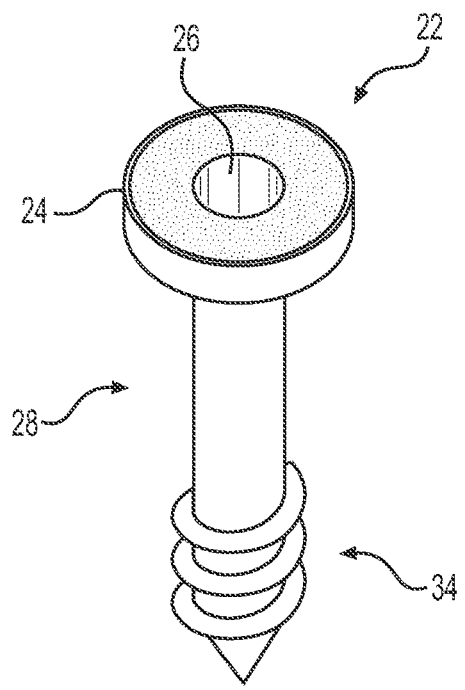
FIG. 1C is an illustration of a smart screw in accordance with an example embodiment.

FIG. 1C is an illustration of a smart screw 22 in accordance with an example embodiment. Smart screw 22 comprises a screw head 24, a shaft 28, and threads 34. A region 26 in screw head 24 is designed to engage with a bit of a screw gun for screwing smart screw 22 into the musculoskeletal system. Shaft 28 is cannulated shaft. In one embodiment, electronic circuitry and one or more sensors can be placed in the cannulated shaft 28 of smart screw 22. The electronic circuitry in the cannulated shaft 28 of smart screw 22 controls a measurement process and transmits measurement data to a computer in proximity to smart screw 22. In one embodiment, the length of shaft 28 is within a range of 2-100 millimeters. In one embodiment, shaft 28 has a diameter from 2-10 millimeters.

Figure 1D:
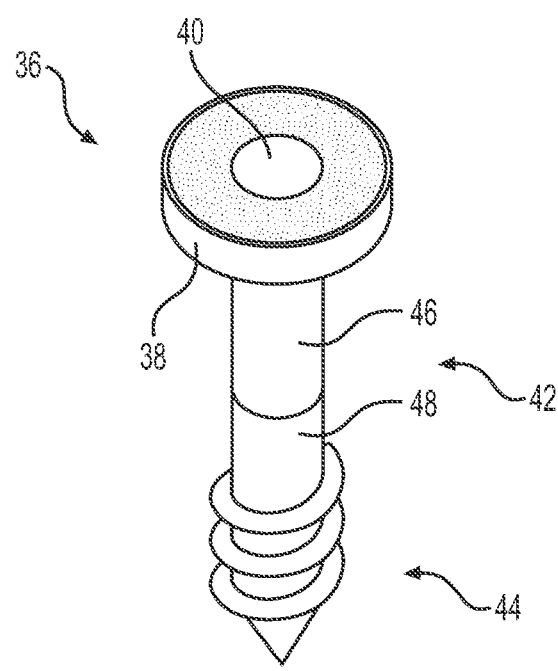
FIG. 1D is an illustration of a smart screw in accordance with an example embodiment.

FIG. 1D is an illustration of a smart screw 36 in accordance with an example embodiment. Smart screw 36 comprises a screw head 38, a shaft 42, and threads 44. A region 40 in screw head 38 is designed to engage with a bit of a screw gun for screwing smart screw 36 into the musculoskeletal system. Shaft 42 is divided into two sections. A section 46 is a solid section of shaft 42. A section 48 is a cannulated section of shaft 42. In one embodiment, electronic circuitry and one or more sensors can be placed in section 48 of shaft 40. The electronic circuitry in the cannulated shaft 42 of smart screw 36 controls a measurement process and transmits measurement data to a computer in proximity to smart screw 36. In one embodiment, the length of shaft 42 is within a range of 2-100 millimeters. In one embodiment, shaft 42 has a diameter from 2-10 millimeters. The size of the smart screws as disclosed applies to all screws shown herein below.

Figure 1E:
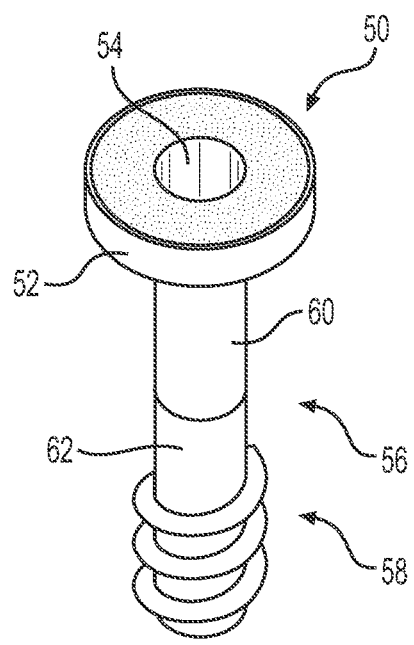
FIG. 1E is an illustration of a smart screw in accordance with an example embodiment.

FIG. 1E is an illustration of a smart screw 50 in accordance with an example embodiment. Smart screw 50 comprises a screw head 52, a shaft 56, and threads 58. A region 54 is designed to engage with a bit of a screw gun for screwing smart screw 50 into the musculoskeletal system. Shaft 56 is divided into two sections. A section 60 is a solid section of shaft 56. A section 62 is a cannulated section of shaft 56. In one embodiment, electronic circuitry and sensors can be placed in section 62 of shaft 56. The electronic circuitry in the cannulated shaft 56 of smart screw 50 controls a measurement process and transmits measurement data to a computer in proximity to smart screw 50. In one embodiment, the length of shaft 56 is within a range of 2-100 millimeters. In one embodiment, shaft 56 has a diameter from 2-10 millimeters.

Figure 1F:
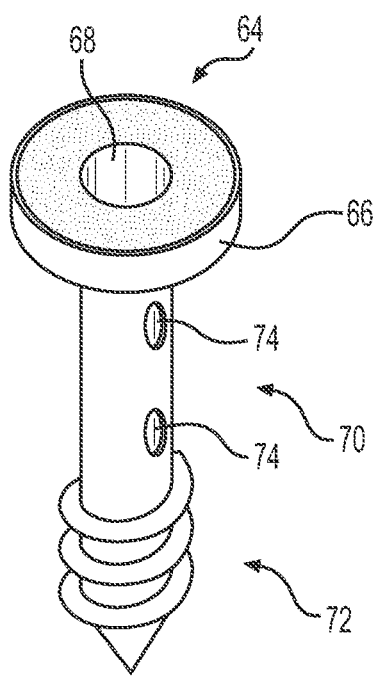
FIG. 1F is an illustration of a smart screw in accordance with an example embodiment.

FIG. 1F is an illustration of a smart screw 64 in accordance with an example embodiment. Smart screw 64 comprises a screw head 66, a shaft 70, and threads 72. A region 68 is designed to engage with a bit of a screw gun for screwing smart screw 64 into the musculoskeletal system. In one embodiment, shaft 70 of smart screw 64 is cannulated. In one embodiment, electronic circuitry and sensors can be placed in the cannulated shaft 70, screw head 66, or both. The electronic circuitry in the cannulated shaft 70 of smart screw 64 controls a measurement process and transmits measurement data to a computer in proximity to smart screw 64. In one embodiment, smart screw 64 can have a plurality of openings 74. In one embodiment, openings 74 couple to the cannulated shaft 70 of smart screw 64. Opening 74 provide access to an external environment outside of smart screw 64 or supports placement of an object outside of smart screw 64. In one embodiment, openings 74 can be formed in threads 72 of shaft 70. Sensors can be used to measure one or more parameters through openings 74.

Figure 1G:
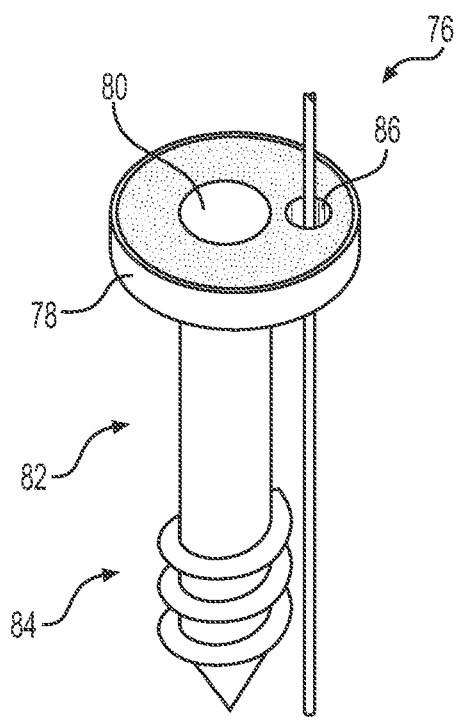
FIG. 1G is an illustration of a smart screw having a dual channel in accordance with an example embodiment.

FIG. 1G is an illustration of a smart screw 76 having a dual channel in accordance with an example embodiment. Smart screw 76 comprises a screw head 78, a shaft 82, and threads 84. A region 80 is designed to engage with a bit of a screw gun for screwing smart screw 76 into the musculoskeletal system. In one embodiment, shaft 82 of smart screw 76 is cannulated. The cannulated shaft 82 is a first channel of smart screw 76. In one embodiment, electronic circuitry and sensors can be placed in the cannulated shaft 82, screw head 78, or both. The electronic circuitry in the cannulated shaft 82 of smart screw 76 controls a measurement process and transmits measurement data to a computer in proximity to smart screw 76. A second channel corresponds to opening 86 through screw head 78. In one embodiment, the second channel can be used for a guide wire. Guide wires are used for drilling pilot holes in bones to test the bone before placing screws.

Figure 1H:
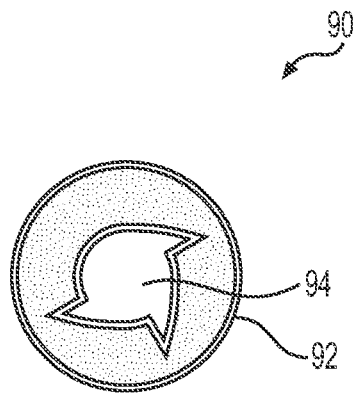
FIG. 1H is an illustration of a smart screw and a washer in accordance with an example embodiment.

FIG. 1H is an illustration of a smart screw 90 and a washer 92 in accordance with an example embodiment. In one embodiment, washer 92 couples to smart screw 90 at a head of screw 90. In one embodiment, washer 92 is fastened to smart screw 90 such that rotating smart screw 90 also rotates washer 92. Alternatively, washer 92 can freely rotate around the shaft of smart screw 90.

Figure 1I:
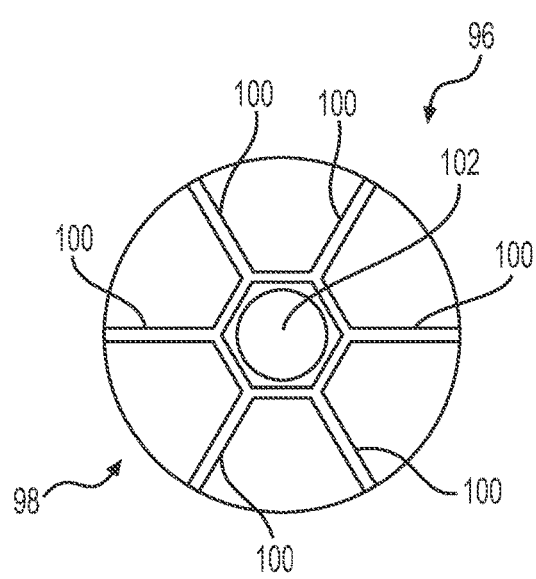
FIG. 1I is an illustration of a washer in accordance with an example embodiment.

FIG. 1I is an illustration of a washer 98 in accordance with an example embodiment. A head 102 of a smart screw 96 is located centrally to washer 98. Washer 98 includes a plurality of electric channels 100. In one embodiment, washer 98 can include one or more electronic channels 100. In one embodiment, the one or more electronic channels 100 can comprise one or more interconnects for coupling to electronic circuitry of smart screw 96 or washer 98. One or more electronic channels 100 can form part of an antenna system for transmitting or receiving data or information. In one embodiment, the one or more electronic channels can include electronic circuitry and one or more sensors.

Figure 1J:
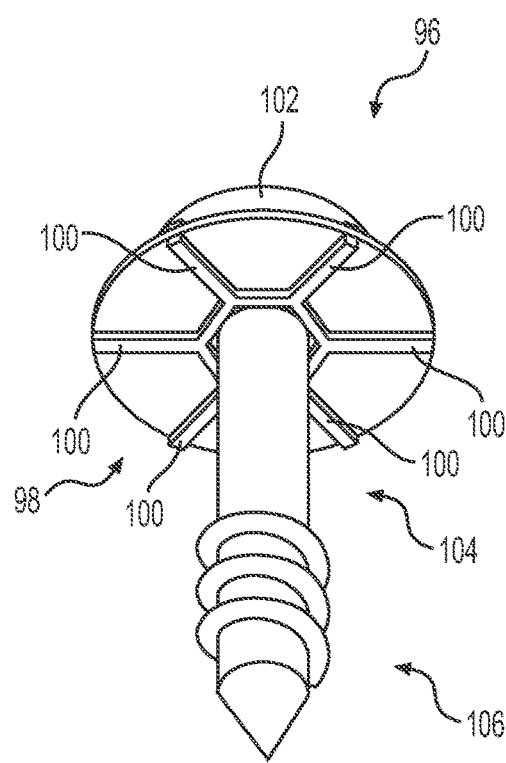
FIG. 1J is an illustration of the washer and the smart screw in accordance with an example embodiment.

FIG. 1J is an illustration of washer 98 and smart screw 96 in accordance with an example embodiment. The illustration shows one or more electronic channels 100 on an underside of washer 98. Smart screw 96 comprises head 102, shaft 104, and threads 106. Shaft 104 of smart screw 96 couples through an opening of washer 98. Washer 98 couples to head 102 of smart screw 96. As previously stated smart screw 96 and washer 98 can house electronic circuitry and one or more sensors for generating quantitative measurement data, monitoring the musculoskeletal system, or providing therapy to the musculoskeletal system.

Figure 2:
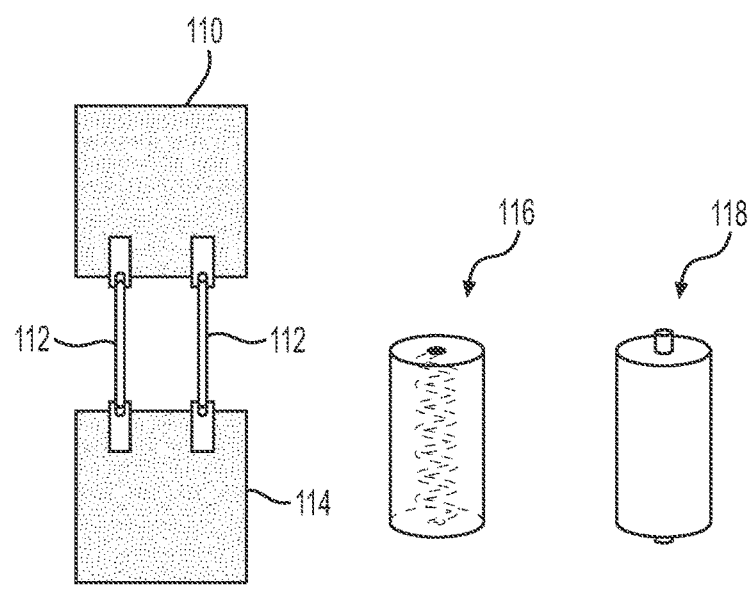
FIG. 2 is an illustration of components used in a smart screw system in accordance with an example embodiment.

FIG. 2 is an illustration of components used in a smart screw system in accordance with an example embodiment. In general, the components used in the smart screw system have a small form factor configured to fit within a cannulated shaft or head of an orthopedic screw. A flexible interconnect 110 can couple to a flexible interconnect 114 by an interconnect 112. In one embodiment, flexible interconnect 110, interconnect 112, and flexible interconnect 114 can be folded or rolled to fit within the washer or screw. Flexible interconnect 110 and flexible interconnect 114 provide area to mount and interconnect electronic circuitry and a plurality of sensors to form a circuit. Flexible interconnect 110, interconnect 112, and interconnect 114 can have one or more layers to reduce a form factor. The electronic circuitry can include digital circuitry, processors, digital logic, analog circuitry, interface circuitry, power management circuitry, and transmit and receive circuitry. In one embodiment, the total area of flexible interconnect 110, interconnect 112, and flexible interconnect 114 is approximately 1-2 millimeters square. An integrated device 116 is an energy harvesting system that is designed to generate energy to power the screw. Device 118 is a power source or power storage device for providing power to the electronic circuitry and sensors. The power source or power storage can be a battery, capacitor, inductor, or other energy device. In one embodiment, the integrated device 116 provides power to device 118 to recharge or refresh device 118 to provide power when the electronic circuitry and sensors are enabled. Alternatively, power could be transmitted via radio frequency or coupled inductively to provide power to device 118. Sensors coupled to the electronic circuitry can comprise Piezosensors, MEMs sensors, Bio sensors, Optical Sensors, acoustical sensors, physical sensors, and environmental sensors to name but a few.

Figure 3A:
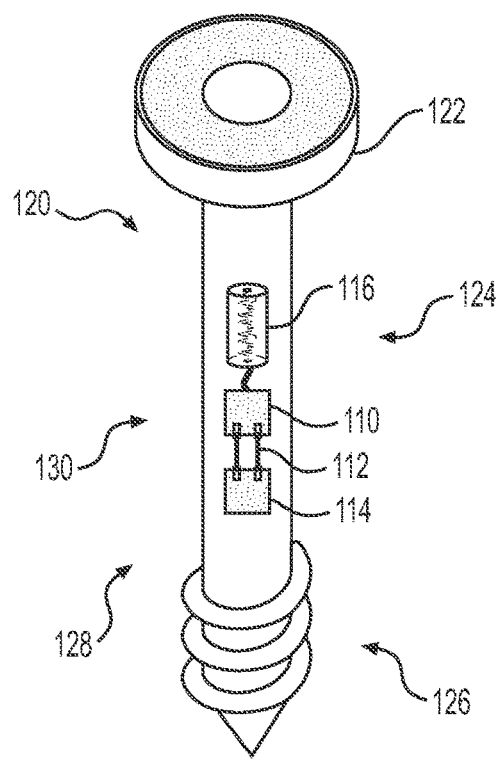
FIG. 3A is an illustration of a smart screw system in accordance with an example embodiment.

FIG. 3A is an illustration of a smart screw system 120 in accordance with an example embodiment. Smart screw system 120 comprises a smart screw 128, a measurement system 130, and a computer configured to receive measurement data. Smart screw 128 comprises a head 122, a cannulated shaft 124, and threads 126. Measurement system 130 comprises integrated device 116, interconnect 110, interconnect 112, and interconnect 114. Electronic circuitry and sensors can be mounted on and coupled together to form measurement system 130 by interconnect 110, interconnect 112, and interconnect 114. In the example, the walls of cannulated shaft 124 are transparent to show measurement system 130 housed within cannulated shaft 124. Alternatively, interconnect, 110, interconnect 112, interconnect 114, and the electronic circuitry can be rolled up into a cylinder to fit within cannulated shaft 124.

Integrated device 116 is an energy harvesting device that generates energy to power smart screw system 120. Alternatively, device 118 of FIG. 2 could be placed within smart screw 128 in place of integrated device 116 to power the electronic circuitry. In one embodiment, integrated device 116 receives a radio frequency signal from an external environment that is converted to power smart screw system 120. The radio frequency signal can also contain information, data, or control signals that is received by smart screw system 120. Alternatively, integrated device 116 can harvest energy through movement or receive energy inductively. Electronic circuitry and sensors on interconnect 110, interconnect 112, and interconnect 114 controls a measurement process and transmit measurement data. The measurement process can comprise generating quantitative measurement data or providing therapy in proximity to smart screw system 120.

Figure 3B:
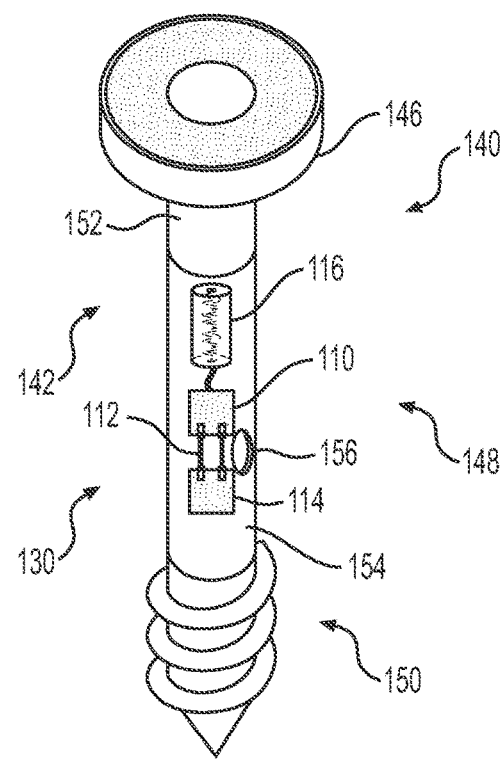
FIG. 3B is an illustration of a smart screw system in accordance with an example embodiment.

FIG. 3B is an illustration of a smart screw system 140 in accordance with an example embodiment. Smart screw system 140 comprises a smart screw 142, measurement system 130, and a computer configured to receive measurement data. Smart screw 142 comprises a head 146, a shaft 148, and threads 150. Shaft 148 comprises a solid section 152 of shaft 148 and a cannulated section 154 of shaft 148. Measurement system 130 is placed in cannulated section 154 of shaft 148.

Measurement system 130 comprises integrated device 116, interconnect 110, interconnect 112, and interconnect 114. Integrated device 116 powers the electronic circuitry. Alternatively, device 118 of FIG. 2 can power measurement system 130. Electronic circuitry and sensors can be mounted on and coupled together to form measurement system 130 by interconnect 110, interconnect 112, and interconnect 114. In the example, the walls of cannulated shaft 148 are transparent to show measurement system 130 housed within cannulated section 154 of shaft 148. In one embodiment, interconnect 110, interconnect 112, and interconnect 114 can be wrapped into a cylinder and placed in cannulated shaft 114. Cannulated section 154 of shaft 148 has one or more openings 156. The measurement system 144 is exposed to an external environment by the one or more openings 156. In one embodiment, one or more openings 156 expose one or more sensors of measurement system 144 to the external environment.

FIG. 4A is an illustration of a top view of a washer system 160 in accordance with an example embodiment. As shown, a smart screw 162 couples to washer system 160. Alternatively, a screw could also be coupled to washer system 160. Washer system 160 comprises a washer 164 and one or more measurement systems 130. As shown, washer system 160 comprises two measurement systems 130. Surfaces are made transparent to show measurement systems 130. In the example, washer 164 is cylindrical in shape having a cavity therein to place measurement systems 130. Measurement systems 130 comprise electronic circuitry and sensors as disclosed herein. In general, each measurement system 130 can have different sensors to measure different parameters, monitor activity, or provide different therapies to the musculoskeletal system. Placing measurement system 130 in washer 164 supports a different location when coupled to the musculoskeletal system for measurement when compared to placement of measurement system 130 within a shaft of smart screw 162. Alternatively, measurement system 130 could also be placed within a screw head or a body of smart screw 162. In one embodiment, measurement systems 130 are in communication with a computer or other electronic device configured to support washer system 160 or smart screw 162. The computer can analyze information provided by measurement systems 130 to assess a status of the musculoskeletal system, identifies issues with the musculoskeletal system, and provide a workflow that supports improvement of the musculoskeletal system.

FIG. 4B is a lateral view of washer system 160 in accordance with an example embodiment. In the example, washer system 160 couples to a head of smart screw 162. As shown, washer 164 includes one or more measurement systems 130. Surfaces are made transparent to show measurement systems 130. In one embodiment, washer 164 couples to a surface of the musculoskeletal system when smart screw 162 is screwed into the musculoskeletal system. In one embodiment, washer 164 prevents or stops smart screw 162 from further penetration into the musculoskeletal system.

FIG. 5A is an illustration of a plurality of smart screws configured to communicate to a computer in accordance with an example embodiment. A smart screw 170 and a smart screw 172 are coupled to a bone 176. In the example, smart screws 170 and 172 are cannulated and each has a measurement system 130 therein. The shafts of smart screws 170 and 172 are made transparent to show measurement systems 130. In one embodiment, measurement system 130 of smart screw 170 and measurement system 130 of smart screw 172 is located within bone 176. Smart screws 170 and 172 are in communication with a computer 174. Smart screws 170 and 172 can communicate through an energy wave or pulse such as radio frequency signals, ultra sonic signals, or electromagnetic radiation. In the example, smart screw 170 is located farther from computer 174 than smart screw 172. In one embodiment, smart screw 170 communicates with smart screw 172. Smart screw 172 can store information from smart screw 170 or immediately transmit the information from smart screw 172 to computer 174. Smart screw 172 is in continuous, periodic, or random communication with computer 174. In one embodiment, smart screw 172 transmits and receives information with computer 174. The information that smart screw 172 transmits to computer 174 can include information or measurement data from smart screw 170. Similarly, some information transmitted from computer 174 to screw 172 can be transmitted to smart screw 170. Computer 174 can display measurement data from smart screws 170 and 172, use the measurement data to determine a status of the musculoskeletal system, and provide a workflow to support improvement of the musculoskeletal system. Smart screws 170 and 172 can be configured to provide therapy to bone 176 such as healing a fracture with an ultrasonic signal.

Figure 5B:
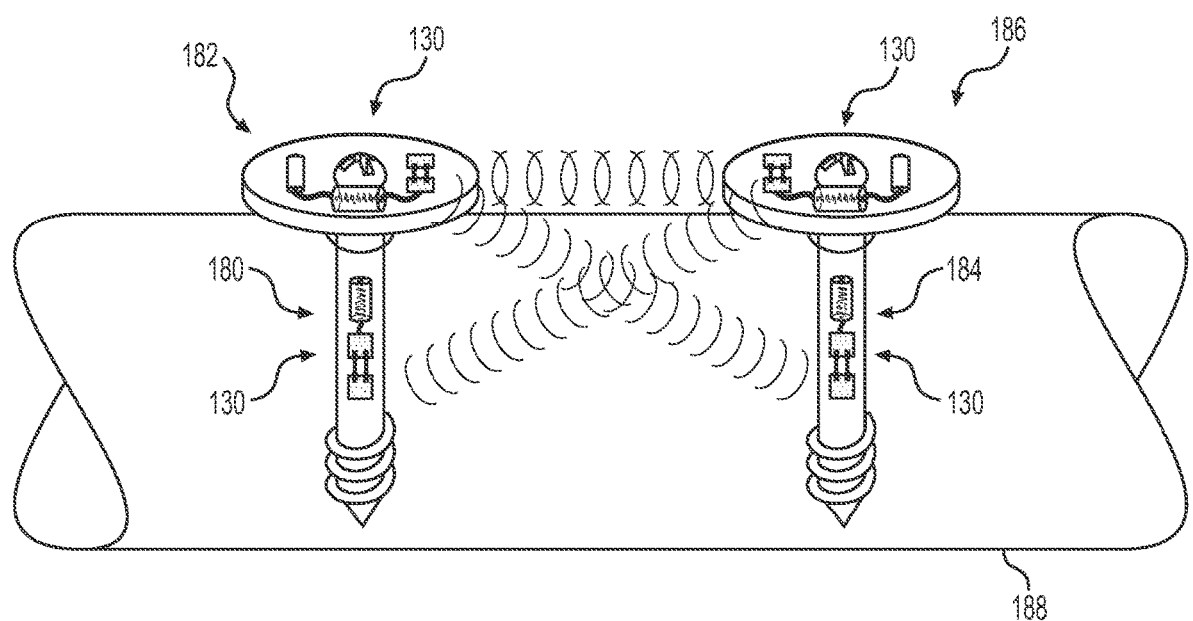
FIG. 5B is an illustration of a plurality of smart screws with a plurality of smart washers in communication with one another in accordance an example embodiment.

FIG. 5B is an illustration of a plurality of smart screws with a plurality of smart washers in communication with one another in accordance an example embodiment. A smart screw 180 having a smart washer 182 is located in bone 188 at a first location. Smart screw 180 and smart washer 182 each have a measurement system 130.

Surfaces are made transparent to show measurement systems 130. Each measurement system 130 of smart screw 180 and smart washer 182 can perform different functions. Measurement system 130 of smart screw 180 is screwed into bone 188. Measurement system 130 of washer 182 couples to a surface of bone 188 such that measurement system 130 of washer 182 can interface with bone 188 or an external environment in proximity to bone 188.

A smart screw 184 having a smart washer 186 is located in bone 188 at a second location. Smart screw 184 and smart washer 186 each have a measurement system 130. Surfaces are made transparent to show measurement systems 130. Each measurement system 130 of smart screw 184 and smart washer 186 can perform different functions. Measurement system 130 of smart screw 184 is screwed into bone 188. Measurement system 130 of washer 186 couples to a surface of bone 188 such that measurement system 130 of washer 186 can interface with bone 188 or an external environment in proximity to bone 188.

In general, each measurement system 130 can be in communication with another measurement system 130. The communication can be two-way or one-way. In one embodiment, communication can occur through ultrasonic, radio frequency, magnetic, optical, or other signal types. Signals output by each measurement system 130 can also be used to measure a parameter or to provide some form of therapy. In the example, smart washer 182 is communicating with smart screw 184 in bone 188. Smart washer 186 is communicating with smart screw 180. Smart washer 182 and 184 are in also in communication with one another. The communication could be to initiate a measurement, receive measurement data, provide information, or provide therapy that affects bone 188. Although not shown, a computer could also be receiving and analyzing measurement data or information from smart screw 180, smart screw 184, smart washer 182, and smart washer 186 to analyze or provide it to a patient or doctor for providing feedback on the injury or repair.

Figure 6A:
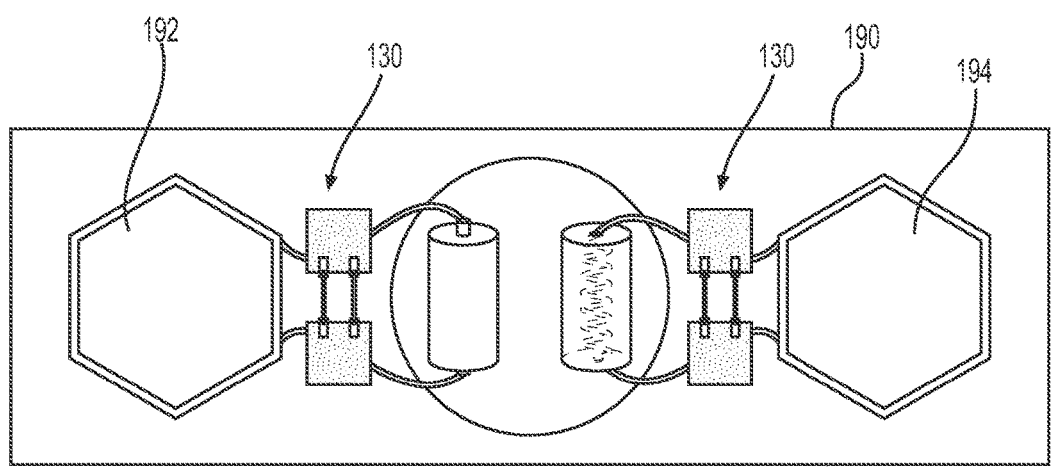
FIG. 6A is an illustration of a smart plate in accordance with an example embodiment.

FIG. 6A is an illustration of a smart plate 190 in accordance with an example embodiment. A smart plate 190 has one or more measurement systems 130. Smart plate 190 also has two or more openings. Each opening in smart plate 190 is configured to receive a smart screw. As shown, a smart screw 192 and a smart screw 194 couples through openings in smart plate 190 to fasten plate 190 to the musculoskeletal system. In one embodiment, plate 190 distributes loading by smart screw 192 and smart screw 194 across a surface of plate 190 thereby decreasing the loading per unit area on the musculoskeletal system. Plate 190 also provides one or more locations for housing measurement systems 130. In one embodiment, plate 190 can have one or more cavities in which measurement systems 130 are placed. Alternatively, measurements systems can be coupled to a surface of plate 190. Measurement systems 130 of plate 190 can be in communication with smart screws 192 and 194, a computer, or each other.

Figure 6B:
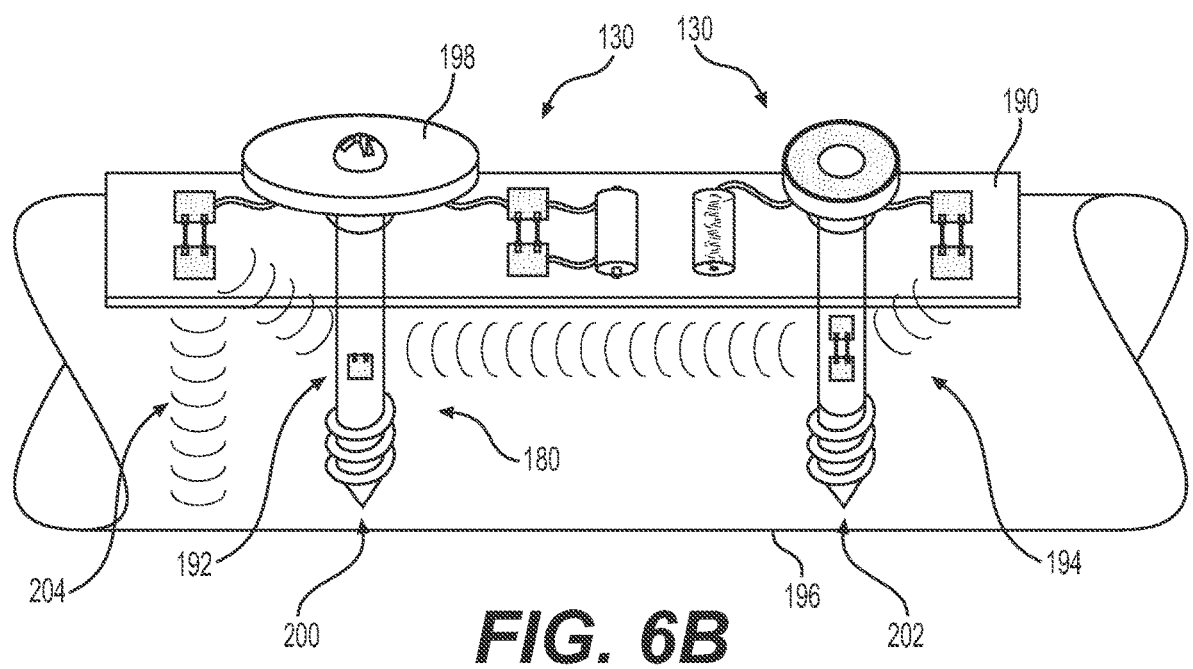
FIG. 6B is an illustration of the plate coupled to a bone in accordance with an example embodiment.

FIG. 6B is an illustration of plate 190 coupled to bone 196 in accordance with an example embodiment. Plate 190 couples to a bone 196 held in place by smart screw 192 at location 200 in bone 196. In one embodiment, a washer 198 can be used in conjunction with smart screw 192 to hold plate 190. Similarly, plate 190 is held in place by smart screw 192 at location 202 in bone 196. Plate 190 distributes loading to bone 196 over the area of plate 190 in contact with bone 196 versus the area of washer 198 or the head of screw 194. Note the area of plate 190 is significantly larger than washer 198 and the head of smart screw 194 combined. Measurement systems 130 on plate 190 can be in communication with smart screws 192 and 194. Similarly, measurements systems 130 on plate 190 can be in communication with one another. A computer (not shown) can also communicate with measurement systems 130 of plate 190 or smart screws 192 and 194. In one embodiment, measurement system 130 of plate 190 can be providing a therapy for healing a bone as indicated by energy wave 204.

FIG. 7A is an illustration of a handle 210 in accordance with an example embodiment. Handle 210 is used to rotate and torque a percutaneous screw into the musculoskeletal system. Handle 210 includes a measurement system 130 configured to support a placement of a percutaneous screw. The walls of handle 210 are made transparent to show that measurement system 130 is within a cavity of handle 210. In one embodiment, a plurality of percutaneous screws can be placed in vertebra of the spine to hold a metal rod configured to shape and stabilize the spine. The percutaneous screws must be coupled to a strong dense portion of the vertebra to hold the metal rod that forcibly changes the spine shape. The percutaneous screws could loosen or pull out if not fastened correctly into an area of strong bone mass. In one embodiment, handle 210 is 4-10 centimeters long. In one embodiment, measurement system 130 can measure the torque applied to the smart screw being installed as well as measure other parameter related to the installation.

FIG. 7B is an illustration of a percutaneous screw 220 in accordance with an example embodiment. Percutaneous screw 220 includes a measurement system 130. A connector 222 is configured to couple to handle 210 of FIG. 7A. Connector 222 can include leads from measurement system 130 of percutaneous screw 220 that couple to measurement system 130 of handle 210 of FIG. 7A or other electronic circuitry within handle 210 of FIG. 7A. Alternatively, leads from measurement system 130 of percutaneous screw 220 do not have to couple to handle 210. For example, leads extending into connector 222 can be antenna leads for communication. A shaft of percutaneous screw 210 is cannulated to house measurement system 130. The walls of the shaft are made transparent to show measurement system 130.

FIG. 7C is an illustration of handle 210 coupled to percutaneous screw 220 in accordance with an example embodiment. Handle 210 is rotated such that threads of percutaneous screw 220 drill into bone 230. Upon reaching a predetermined distance within bone 230 the drilling is stopped. In one embodiment, the predetermined distance can be measured by one of measurement system 130 of handle 210 or measurement system 130 of percutaneous screw 220. In one embodiment, prongs can be extended from percutaneous screw 220 to further stabilize percutaneous screw 220 within bone 230.

Figure 7D:
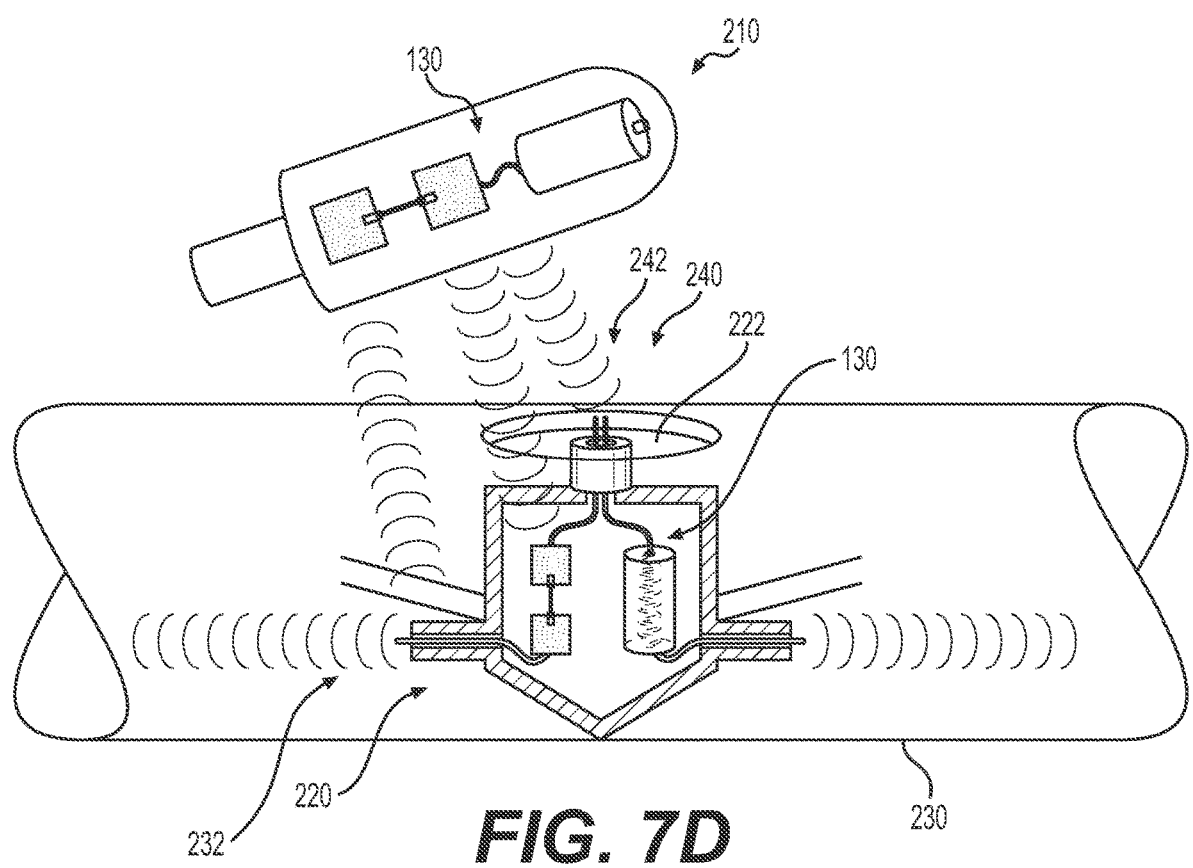
FIG. 7D is an illustration of the handle removed from the percutaneous screw after being screwed into the bone in accordance with an example embodiment.

FIG. 7D is an illustration of handle 210 removed from percutaneous screw 220 after being screwed into bone 230 in accordance with an example embodiment. Percutaneous screw 220 is screwed into bone 230 such that measurement system 130 within percutaneous screw 220 is embedded within bone 230. An opening 240 in bone 230 from drilling percutaneous screw 220 into bone 230 exposes connector 222 within bone 230. In one embodiment, an antenna 242 resides within connector 222 that supports communication to one or more devices. In the example, handle 210 is in communication with percutaneous screw 220. Measurement system 130 of percutaneous screw 220 can output one or more signals for measurement or therapy within bone 230 for measuring a parameter that can be received by handle 210. Similarly, measurement system 130 in handle 210 can output one or more signals that are configured to measure a parameter or provide therapy to bone 230 or percutaneous screw 220.

Figure 8:
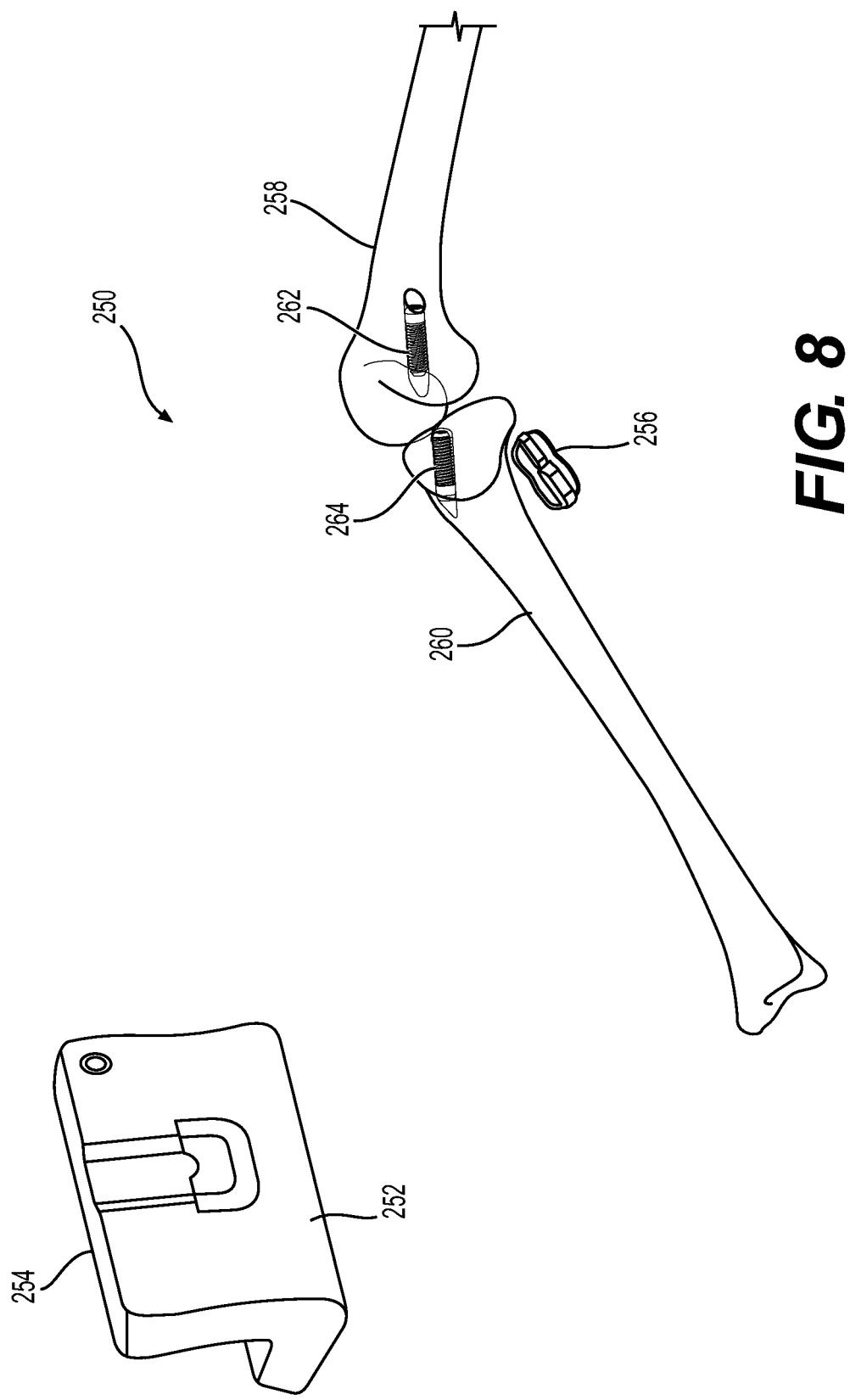
FIG. 8 is an illustration of an orthopedic measurement system in accordance with an example embodiment.

FIG. 8 is an illustration of an orthopedic measurement system 250 in accordance with an example embodiment. Orthopedic measurement system 250 comprises a computer 252, a patch device 256, subcutaneous screw 262, and subcutaneous screw 264. Orthopedic measurement system 250 has two way communication between computer 252, patch device 256, and one or more batteryless devices that are implanted in the musculoskeletal system. The patch device 256 is configured to be placed in proximity to subcutaneous screws 262 and 264. Patch device 256 can provide energy to power subcutaneous screws 262 and 264 to measure one or more parameters. In general, subcutaneous screws 262 and 264 have one or more sensors configured to measure one or more parameters. Subcutaneous screws 262 and 264 can be configured to provide therapy or support improved health locally or throughout the body. Subcutaneous screws 262 and 264 can transmit measurement data to patch device 256 or computer 252. Display 254 of computer 252 can display the measurement data. Computer 252 can include one or more computer programs that can analyze the measurement data, utilize the measurement data in a process, procedure, workflow, or review, and further transmit the measurement data or results to a patient, doctor, surgeon, or other medical staff to support patient health.

In the example, a subcutaneous screw 262 and a subcutaneous screw 264 are coupled to the musculoskeletal system. Subcutaneous screw 262 is placed within femur 258 and subcutaneous screw 264 is placed within tibia 260. In one embodiment, femur 258 is drilled and tapped such that subcutaneous screw 262 is placed in a first predetermined location in femur 258. Similarly, tibia 260 is drilled and tapped such that subcutaneous screw 264 is placed in a second predetermined location in tibia 260. Subcutaneous screws 262 and 264 are screwed into their corresponding openings in femur 258 and tibia 260 and can be placed temporarily or permanently.

As mentioned previously patch device 256 is placed in proximity to subcutaneous screws 262 and 264. In the example, patch device 256 can have a medical grade adhesive that couples patch device 256 to a skin of the patient. The medical grade adhesive will make patch device 256 adhere to the skin under active conditions but can be removed. Ideally, the placement of patch device 256 is the shortest distance between screws 262 and 264 that maximizes energy transfer and communication. In one embodiment, subcutaneous screws 262 and 264 do not have a power source. Energy is provided by patch device 256 and stored on subcutaneous screws 262 until a predetermined energy threshold is met that supports operation of subcutaneous screw 262 or 264 for a predetermined time period. In one embodiment, the predetermined time period corresponds to having sufficient energy to take measurements using the one or more sensors and to transmit the measurement data to patch device 256.

In one embodiment, patch device 256, subcutaneous screw 262, and subcutaneous screw 264 include a position measurement system or tracking system. In the example, the position measurement system or tracking system is an IMU (inertial measurement unit). The position measurement system can also be a GPS chip, an acoustical ranging device, optical devices, inertial devices, magnetometers, inclinometers, or MEMs devices. In general, subcutaneous screws 262 and 264 couple to predetermined locations of the musculoskeletal system. In one embodiment, screws 262 and 264 couple to bones of the musculoskeletal system that move relative to one another such that screws 262 and 264 track movement or position. In the example, subcutaneous screws 262 and 264 are respectively implanted in femur 258 and tibia 260 during a total knee arthroplasty in predetermined locations. The IMU within each screw can be used to measure movement and rotation of femur 258 and tibia 260. The measurement data from the IMU of each screw can be used to determine range of motion, joint alignment, and gait mechanics with the prosthetic knee joint installed. The measurement data can further be used to determine a regimen that optimizes user performance of the prosthetic knee joint to reduce rehabilitation time or allow increased activity or mobility. Examples of other applications for subcutaneous screws 262 and 264 are the use of cameras, optical sensors, or light emitting diodes to monitor regions near the device placement. Similarly, the sensors can view synovial fluid near a joint of the musculoskeletal system to monitor infection via color or turbidity. Sensors to monitor pH or temperature can also be used to indicate unwanted activity in or near the joint. Sensors to detect micromotion of a prosthetic component to femur 258 or tibia 260 can indicate stability of the adhesive holding a prosthetic component to bone. Subcutaneous screws 262 or 264 can be used to provide therapy for improving the musculoskeletal system, healing a fracture, or measuring bone density. Thus, the use of orthopedic measurement system 250 can provide substantial benefits by generating quantitative measurement data related to the musculoskeletal system.

Figure 9:
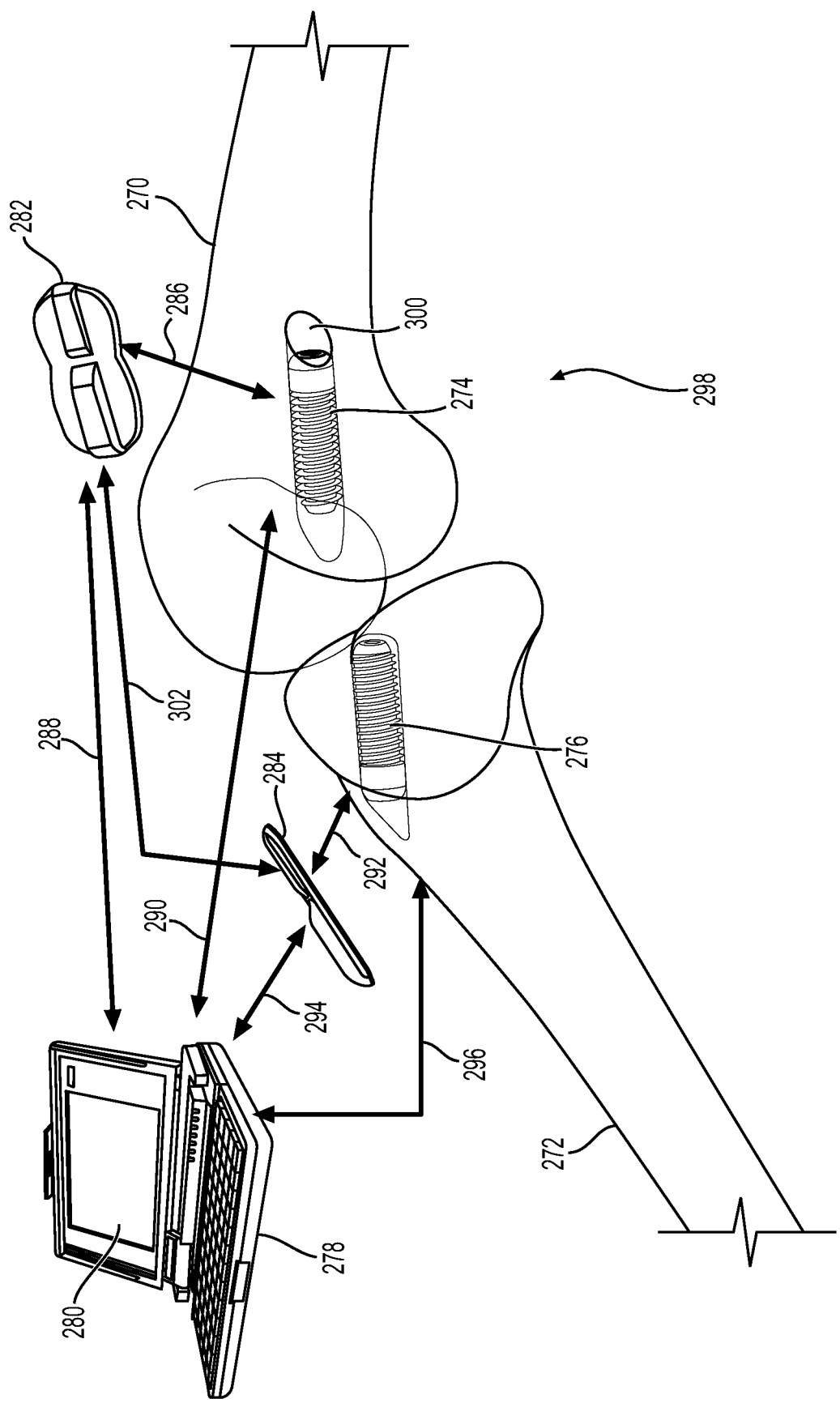
FIG. 9 is an illustration of communication paths of an orthopedic measurement system in accordance with an example embodiment.

FIG. 9 is an illustration of communication paths of an orthopedic measurement system 298 in accordance with an example embodiment. In general, measurement system 298 is coupled to the musculoskeletal system. Measurement system 298 can be used on the knee joint, shoulder joint, hip, spine, ankle, wrist, fingers, toes, elbow joint, skull, and generally bone. In one embodiment, measurement system 298 is used to assess position and movement of the musculoskeletal system. In one embodiment, measurement system 298 can include one or more sensors to provide measurement data or provide therapeutic benefit. The physical parameter or parameters of interest that can be incorporated into measurement system 298 are temperature, blood oxygenation, pressure, sound, pH, SaO2, humidity, barometric pressure, height, length, width, tilt/slope, position, orientation, load magnitude, force, pressure, displacement, density, viscosity, light, color, sound, optical, vascular flow, visual recognition, alignment, rotation, inertial sensing, turbidity, strain, angular deformity, vibration, torque, elasticity, motion, acceleration, infection detection, pain inhibition, magnetic, gyroscopic, infrared, chemical sensing, biological sensing, and energy harvesting to name but a few. Often, two or more measured parameters are used in conjunction with another to perform a clinical assessment. Data collection of measurement data from measurement system 298 can be used by computer 278 or provided to a database for further analysis. A graphical user interface can support assimilation of measurement data. The measurement data can be periodically measured and transmitted to a computer for further processing.

Orthopedic measurement system 298 comprises a computer 278, device 282, device 284, screw 274, and screw 276. Although the example shows two screws 274 and 276, measurement system 298 can comprise more than two screws and more than two devices. In one embodiment, device 282, device 284, screw 274, and screw 276 have similar or identical electronic circuitry. In one embodiment, device 282 and device 284 are configured to provide power to respectively to screw 274 and screw 276. In one embodiment, a single device can provide power to multiple screws. Alternatively, multiple devices can be placed in a manner to provide power to a single screw. In general, an energy wave received by screw 274 or screw 276 is converted to a DC voltage to power the electronic circuitry therein. Using multiple devices increases the speed of charging and supports charging even as the orientation of the musculoskeletal system changes. For example, positioning of a device can change as the musculoskeletal system is moved through a range of motion. In one embodiment, the energy transmitted from device 282 or device 284 is a radio frequency signal of a predetermined frequency or frequencies. Any radio frequency signal within the predetermined frequency or frequencies received by screw 274 or screw 276 is converted from an alternating voltage to a DC voltage to power internal circuitry within screw 274 or screw 276. The transmitted radio frequency signal can also provide information that is removed from the radio frequency signal prior to the energy being harvested. The screw includes at least one antenna configured to receive the radio frequency signal and start the harvesting process.

In one embodiment, devices 282 and 284 can be used pre-operatively and post-operatively. In one embodiment, measurement system 298 does not require a screw such as screws 274 and 276. Devices 282 and 284 can be coupled directly to the skin or held in place by a brace or wrap. In general, devices 282 and 284 include a position tracking device to monitor movement, position, and trajectory of each device. Coupling devices 282 and 284 to a first bone and a second bone of a musculoskeletal system supports tracking movement of the first bone relative to the second bone. In one embodiment, devices 282 each include an IMU (inertial measurement unit). Devices 282 and 284 can also include one or more sensors configured to measure one or more parameters. The sensors can also include devices that provide therapy, healing, support rehabilitation, or pain mitigation. Devices 282 and 284 include electronic circuitry 310, an enclosure, and a power source disclosed herein below. For example, a knee brace or wrap can include devices 282 and 284. The knee brace or wrap is configured to hold devices 282 and 284 in predetermined locations. In one embodiment, the knee brace is configured to couple device 282 to femur 270 and the knee brace is configured to couple device 284 to tibia 272. Devices 282 and 284 are configured to communicate with computer 278. Devices 282 and 284 can communicate directly or indirectly through a router, network, or mesh network. Devices 282 and 284 can harvest energy from radio frequency signals they receive. In one embodiment, devices 282 and 284 use the harvested energy to charge a power source or battery within devices 282 and 284 thereby allowing them to operate continuously generating measurement data. Devices 282 and 284 are configured to provide measurement data or information to computer 278. Computer 278 can include software that analyzes the measurement data from devices 282 and 284 to measure gait mechanics that include stride, cadence, activity, and steps. Computer 278 can further include a program that uses the measurement data for a kinetic assessment that includes balance, stability, rotation, graft adherence, graft failure proprioception, range of motion, or muscle strength. Wearing the knee brace prior to an operation can provide patient data that provides information related to pain, activity level, range of motion, and other factors that provides knowledge on the issues the patient is having and how to address a prosthetic component installation that supports a satisfactory patient outcome. A knee brace having devices 282 and 284 also supports rehabilitation and determination when the knee joint is healed after surgery. Devices 282 and 284 can include sensors, camera, or optical devices to monitor a surgical wound after a prosthetic knee joint is implanted. Devices 282 and 284 can also support pain mitigation to facilitate exercise and use of the knee joint. In one embodiment, computer 278 can be a cell phone, tablet, or small device that includes an app. Devices 282 and 284 provide measurement data to the app in the cell phone, tablet, or small device that monitors movement, exercise, or other sensor information. The information related to rehabilitation can be provided to a doctor or staff for review. Data analytics using the measurement data from devices 282 and 284 can be used to modify a therapy to improve results or indicate that the knee joint is fully healed and normal activity can be resumed. Recorded movement or motion can be displayed on a display or compared with prior measurement data to indicate progress. Milestones or issues can be detected using the measurement data and sent to the patient or to a doctor and staff. The doctor or staff can contact the patient if an issue requires a change in a workflow. Measurement data from devices 282 and 284 can be used to determine when an office visit occurs. Although a knee joint was used as an example, devices 282 and 284 can be coupled to monitor movement of any two bones of the musculoskeletal systems such as spine, hip, shoulder, elbow, ankle, wrist, hand, toes. The measurement data from devices 282 and 284 can be of an individual bone or two bones in relation to one another.

In one embodiment, screws 274 and 276 can be implanted during a knee arthroplasty or during a separate surgery. The prosthetic components of the prosthetic knee joint are not shown but femur 270 and tibia 272 are exposed during the installation so it is a simple task to install screws 274 and 276 at this time. A cavity 300 is drilled into femur 270 of the musculoskeletal system. Cavity 300 is tapped having threading similar to screw 274. Screw 274 is then screwed within cavity 300. Different methodologies can be deployed to ensure that screw 274 does not loosen. The threading can be an interference fit that tightens as screw 274 is screwed within the cavity. Alternatively, an adhesive could be applied to the threading of screw 274 that bonds the threads of screw 274 to femur 270. The strength of the bond can be such that screw 274 can be removed when required. A similar process is also performed for screw 276 in tibia 272. The predetermined locations of screws 274 and 276 respectively in femur 270 and tibia 272 are provided to and stored in computer 278. In one embodiment, the precise depth and location of screws 274 and 276 are used in accurately monitoring range of motion, alignment, rotation, anterior-posterior movement, and other positional information to assess knee mechanics.

Devices 282 and 284 are respectively placed near screws 274 and 276. They can be held in place by adhesive on devices 282 and 285 as previously disclosed or by being placed in a wrap that couples to the musculoskeletal system in a manner that supports placement near screws 274 and 276. Devices 282 and 285 can each have one or more sensors or one or more devices for generating measurement data or providing a therapeutic benefit. In the example, due to proximity, screw 274 is primarily receiving energy from device 282. Similarly, due to proximity, screw 276 is primarily receiving energy from device 284. Once energized, screws 274 and 276 can provide measurement data continuously as long as devices 282 and 284 are transmitting a radio frequency signal that energizes screws 274 and 276. In the example, the radio frequency signal transmitted from devices 282 and 284 is typically less than 1 gigahertz. Operating below 1 gigahertz allows sufficient penetration through skin and fluids of the musculoskeletal system to be received in an efficient manner to energize a screw. As previously mentioned, several devices can be used in parallel to transmit to a single screw if the location of the screw is such that the energy is not received at levels that energizes the device to maintain operation. For example, several devices can be placed in a wrap to focus the radio frequency transmission to a single screw. The combined radio frequency transmission can increase the energy received by the antenna of the screw for harvesting.

In one embodiment, the electronic circuitry in a screw such as screws 274 and 276 are identical or substantially equal to the electronic circuitry in devices 282 and 284. This supports reducing cost of the screws or devices by minimizing differences that support repurposing the concept for different applications in the medical space, industrial space, or consumer space that supports increased volume. Thus, devices 282 and 284 have one or more sensors coupled to the electronic circuitry. Devices 282 and 284 can also be configured to generate measurement data and transmit the measurement data to computer 278. Devices 282 and 284 include a battery for energy storage. In one embodiment, the battery of the device is a flexible planar structure that supports two way communication, quantitative measurement, and provides energy to a screw to perform a measurement process. The flexible planar structure of the battery supports a form factor as a patch that can couple to a non-planar surface. The battery can be a rechargeable device. For example, devices 282 and 284 can receive energy from a radio frequency transmission from computer 278 because devices 282 and 284 have the same electronic circuitry as screws 274 and 276. The harvested energy by devices 282 and 284 can be used to recharge the battery or to supplement the power expended during operation of screw 274 and 276.

Each component of orthopedic measurement system 298 has two way communication electronic circuitry. In one embodiment, communication can occur over a single frequency band. Alternatively, two way communication can occur over two or more different frequencies. In one embodiment, a handshake can occur between two devices or two or more devices of orthopedic measurement system 298 before communication are established. In one embodiment, a screw such as screw 274 or screw 276 will receive a radio frequency signal for a predetermined time before beginning a handshake with another device such as computer 278, device 282, or device 284. Energy harvesting occurs during the predetermined time that allows operation of the screw for the handshake, sensor measurement, and transmission of measurement data from the screw.

In the example, device 282 is in two way communication with screw 274 as indicated by double headed arrow 286. Device 282 is coupled to the skin overlying femur 270 in proximity to screw 274. In one embodiment, device 282 can have an antenna focused towards screw 274. Alternatively, device 282 can have an antenna that is omni-directional to support communication in all directions. Screw 274 is configured to take measurement data and transmit the measurement data to device 282. Device 282 can also be configured to generate measurement data from sensors on device 282. The measurement data from screw 274 or device 282 can be stored in memory on device 282 or transmitted to another device. In one embodiment, device 282 transmits the measurement data to computer 278 for review and analysis in real-time as indicated by double headed arrow 288. In one embodiment, screw 274 can have two way communication directly to computer 278 as indicated by double headed arrow 290. Similarly, device 282 can also be in two way communication directly to computer 278 at the same time as screw 274.

In the example, device 284 is in two way communication with screw 276 as indicated by double headed arrow 292. Device 284 is coupled to the skin overlying tibia 272 in proximity to screw 276. In one embodiment, device 284 can have an antenna focused towards screw 276. Alternatively, device 284 can have an antenna that is omni-directional to support communication in all directions. Screw 276 is configured to take measurement data and transmit the measurement data to device 284. Device 284 can also be configured to generate measurement data from sensors on device 284. The measurement data from screw 276 or device 284 can be stored in memory on device 284 or transmitted to another device. In one embodiment, device 284 transmits the measurement data to computer 278 for review and analysis in real-time as indicated by double headed arrow 294. In one embodiment, screw 276 can have two way communication directly to computer 278 as indicated by double headed arrow 296. Similarly, device 284 can also be in two way communication directly to computer 278 at the same time as screw 276. Thus, there are a substantial number of communication paths that can be set up in orthopedic measurement system 298 because each device of the system has two way communication capability. In one embodiment, orthopedic measurement system 298 can be daisy chained to simplify the movement of measurement data. For example, device 282 receives or stores measurement data from screw 274 and device 282 as previously stated. Device 282 transmits the measurement data to device 284 as indicated by arrow 302. Device 284 also receives or stores measurement data from screw 276 and device 284. Device 284 than transmits measurement data related to device 282, device 284, screw 274, and screw 276 to computer 278 for displaying and analyzing the measurement data.

Figure 10:
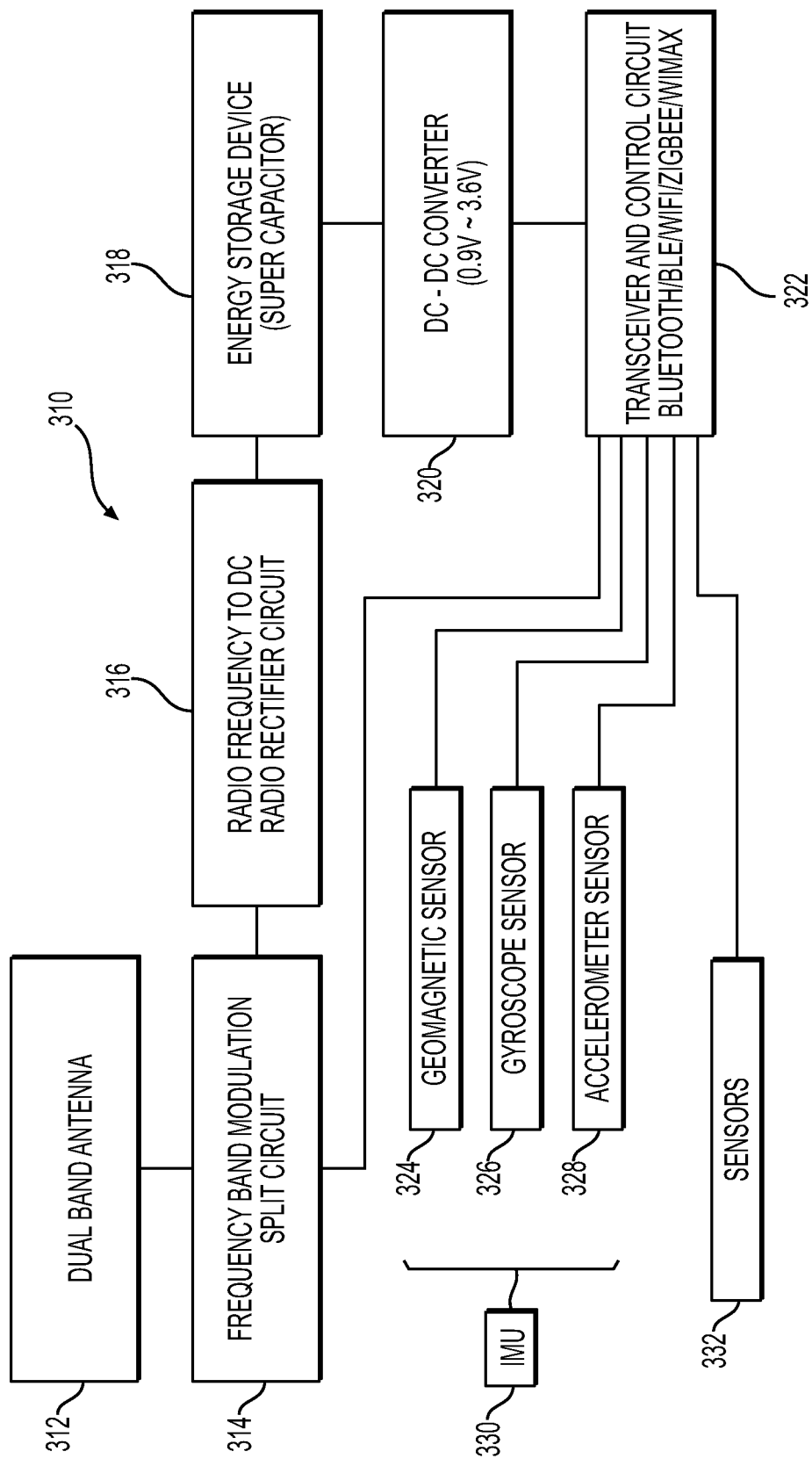
FIG. 10 is an illustration of electronic circuitry for two way communication configured to receive energy to support internal powering, or configured to transmit energy to power another device in accordance with an example embodiment.

FIG. 10 is an illustration of electronic circuitry 310 for two way communication configured to receive energy to support internal powering, or configured to transmit energy to power another device in accordance with an example embodiment. In general, a system can be formed with as little as two devices having electronic circuitry 310 that can communicate with each other. Electron circuitry 310 can be placed in the screws or devices of FIGS. 1-9. A battery or power source can be coupled to electronic circuitry 310 to provide power to electronic circuitry. Alternatively, electronic circuitry can be operated without a battery or power source. The screw or device without a power source can be powered by a signal. In one embodiment, the signal is then harvested by circuitry within electronic circuitry 310 to power the screw or device. The screw or device with or without a battery or power source can include one or more sensors or therapeutic circuitry that operates in real-time while transmitting and receiving information. Electronic circuitry 310 can be used in patch device 256, subcutaneous screw 262, and subcutaneous screw 264 of FIG. 8. Similarly, electronic circuitry 310 can be used in device 282, device 284, screw 274, and screw 276 of FIG. 9. In both examples, systems 250 and 298 respectively of FIG. 8 and FIG. 9 are used to generate measurement data directly within the body and more specifically related to the musculoskeletal system. Systems using electronic circuitry 310 are not limited to medical devices as will be disclosed herein below.

Electronic circuitry 310 comprises a dual band antenna 312, a frequency band modulation split circuit 314, a radio frequency to DC radio rectifier circuit 316, an energy storage device 318, a DC-DC converter 320, a transceiver 322, and an IMU 330. Electronic circuitry 310 can include control logic, memory, and software programming to support a process or function that a device or screw performs. In one embodiment, transceiver and control circuit 322 can comprise one or more of Bluetooth, Bluetooth Low Energy (BLE), Zigbee, Wimax, Wifi, or other communication circuitry. Electronic circuitry 310 can further include sensors 332 to monitor or provide measurement data. Sensors 332 can include one or more devices configured to provide a therapy or improve health. A dual band antenna 312 can comprise two separate antennas each optimized for a specific frequency. In general, electronic circuitry 310 can operate at two or more frequencies. In the example, electronic circuitry 310 operates at two frequencies. One of the frequencies is below 1 gigahertz to support efficient transfer of energy via radio frequency below the skin. In the example, one antenna can be tuned to a frequency below 1 gigahertz in the ISM band. The second antenna can be tuned to a frequency depending on the application. Although the lower frequency (1 gigahertz) will be more efficient in energy transfer both frequencies can be used to harvest energy. In one embodiment, the second antenna operates at a frequency associated with an I.E.E.E. standard that has wide acceptance and supports wireless communication such as Zigbee, WiFi, Bluetooth, Bluetooth Low Energy (BLE), or WiMax but is not limited to such. These standards support communication and the transmission of data. Some of these standards support low power and medium to short range transmission. In one embodiment, a batteryless device using electronic circuitry 310 will use a Bluetooth Low Energy (BLE) transceiver. A BLE transceiver is configured to communicate with any Bluetooth device. The BLE transceiver operates at reduced power that reduces the requirements of energy storage device 318 thereby reducing energy storage requirements to operate electronic circuitry 310 and supports a smaller form factor. In one embodiment, a device having a secondary power source such as a battery can use a standard Bluetooth transceiver. Bluetooth operates at 2.4 gigahertz and supports high speed data transfer within a 10M radius.

Dual band antenna 312 receives a radio frequency signal. Frequency band modulation split circuit 314 couples to dual band antenna 312 and removes information that is carried on the radio frequency signal. In one embodiment, the received radio frequency signal is in the ISM band at 915 megahertz. The information is provided to transceiver and control circuit 322. Transceiver and control circuit 322 is configured to use information from the radio frequency signal, control a measurement process, and transmit measurement data. The radio frequency signal (with information removed) is provided by frequency band modulation split circuit 314 to radio frequency to DC radio rectifier circuit 316. In general, the radio frequency signal is a low power signal. In one embodiment of radio frequency to DC radio rectifier circuit 316, an input matching circuit couples to dual band antenna 312 to efficiently convert an electromagnetic signal to an electrical signal. The electrical signal is then coupled to a rectifier circuit that produces a DC voltage.

Radio frequency to DC radio rectifier circuit 316 couples to energy storage device 318. As it name implies, energy storage device 318 stores energy that will be used to enable electronic circuitry 310. There are many types of energy storage devices that can be used such as an inductor, a battery, a capacitor, magnetic storage, electrochemical storage, or chemical storage to name but a few. In the example, energy from radio frequency to DC radio rectifier circuit 316 is stored on a super capacitor. Energy storage device 318 is configured to store sufficient energy to operate electronic circuitry 310 for a predetermined time period after the radio frequency signal is no longer received. In one embodiment, energy storage device 318 charges for approximately 10 seconds before electronic circuitry 310 is enabled. In one embodiment, the charge in energy storage device 318 is sufficient to generate measurement data and transmit the measurement data to another device.

Energy storage device 318 couples to DC-DC converter 320. DC-DC converter 320 is configured to generate one or more voltages to power electronic circuitry 310. Typically, the voltage on energy storage device 318 is lower than needed. DC-DC converter 320 multiplies the voltage to a usable value for electronic circuitry 310. In one embodiment, DC-DC converter generates one or more voltages from 0.9 volts to 3.6 volts. DC-DC converter 320 couples to transceiver and control circuit 322 to power a measurement process. In one embodiment, transceiver and control circuit 322 is not enabled until energy storage device 318 stores a predetermined amount of energy. Once enabled, transceiver and control circuit 322 controls a measurement process and is configured to transmit measurement data. Transceiver and control circuit 322 can include memory. The memory can be used to store software, calibration data, measurement data, programs, workflows, or other information. IMU 330 and sensors 332 couple to transceiver and control circuit 322. In one embodiment, each device having electronic circuitry 310 will include IMU 330 as a position measurement or tracking device thereby monitoring position and relational positioning between devices. In one embodiment, IMU 330 comprises a geomagnetic sensor 324, a gyroscope sensor 326, and an accelerometer sensor 328. IMU 330 is configured to measure 6 degrees of freedom comprising translation movement along the X, Y, and Z axis as well as rotational movement such as yaw, roll, and pitch around each axis. Sensors 332 can be added to measure one or more parameters of interest and may differ depending on the application of the device.

Figure 11:
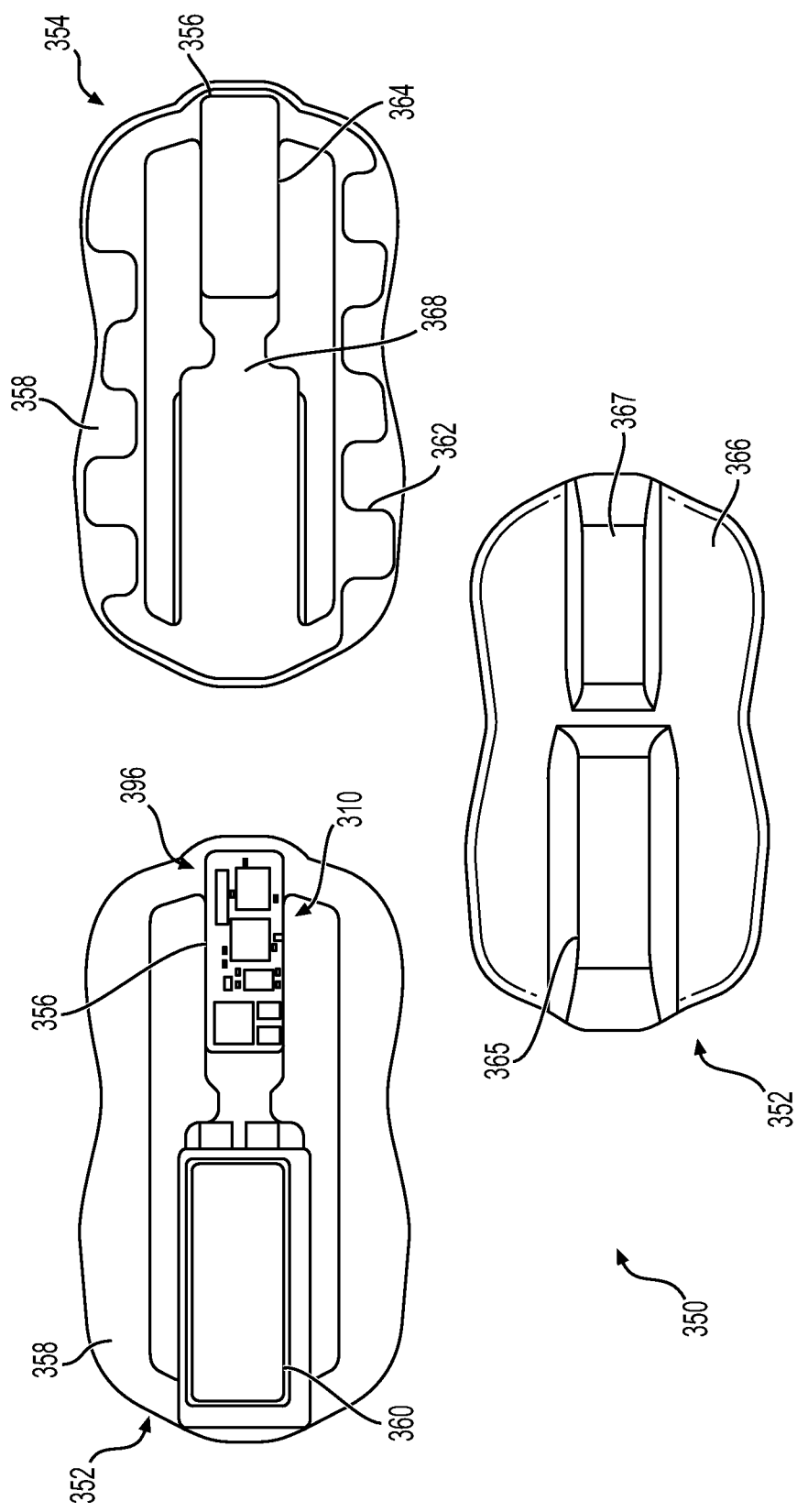
FIG. 11 is an illustration of a device in accordance with an example embodiment.

FIG. 11 is an illustration of multiple views of a device 350 in accordance with an example embodiment. Device 350 is configured to power a batteryless device that can provide therapeutic benefit or generate measurement data. Device 350 includes two way communication circuitry for sending and receiving information. A first side 352 and a second side of 354 of the internal structure of device 350 are illustrated in FIG. 11. First side 352 is shown with an enclosure removed to illustrate the components therein and with the enclosure. Electronic circuitry 310 of FIG. 10 can be viewed on first side 352 with without the enclosure. Electronic circuitry 310 is mounted to and interconnected on a printed circuit board 356 to form an electronic system. In one embodiment, printed circuit board 356 is a multi-layer printed circuit board configured to support a small form factor of device 350. Electronic circuitry 310 and printed circuit board 356 forms a module 396 that can be used for powered and batteryless devices in many different applications. The small form factor, two way communication, and radio frequency powering supports applications for medical devices, industrial applications, and the internet of things where small size and low power are critical. Printed circuit board 356 couples to a flexible printed circuit board 358. A battery 360 can couple to flexible printed circuit board 358 to provide power to electronic circuitry 310. A non-powered device would be identical but without battery 360. In one embodiment, battery 360 is a planar structure that can flex to conform to a non-planar surface. In one embodiment, battery 360 is a rechargeable battery. Battery 360 couples to electronic circuitry 310 through flexible printed circuit board 358.

Referring to second side 354 of device 350, it can be seen that flexible printed circuit board 358 comprises an approximately oval shape. A stripe 368 of flexible printed circuit board 358 couples through the oval shape. In one embodiment, the majority of printed circuit board 356 and battery 360 is mounted on stripe 368 internal to the oval shape of flexible printed circuit board 358. In one embodiment, printed circuit board 356 is configured to bridge from flexible printed circuit board 358 to stripe 368 of flexible printed circuit board 358. A first antenna 362 is formed on the oval shape portion of flexible printed circuit board 358. In one embodiment, first antenna 362 is an antenna for transmitting a frequency less than 1 gigahertz. A second antenna 364 is formed on printed circuit board 356. In the example, second antenna 364 is for a 2.4 gigahertz Bluetooth signal. First side 352 is shown over molded with a flexible substance that forms the enclosure that hermetically seals electronic circuitry 310, printed circuit board 356, battery 360, and flexible printed circuit board 358. For example, the flexible substance for forming the enclosure can be a polymer or a silicone.

A package 366 also called the enclosure is formed over electronic circuitry 310, printed circuit board 356, flexible printed circuit board 358, and battery 360 on first side 352 and second side 354. First side of package 366 illustrates battery 360 and electronic circuitry 310 being covered respectively by area 365 and area 367 of package 366. In one embodiment, package 366 hermetically seals the electronic circuitry the battery from an external environment. In one embodiment, package 366 is formed by over-molding a flexible material on the components. In one embodiment, the flexible material is a silicone that remains flexible so device 350 will conform to a non-planar surface. Not shown, is second side 354 that is also over-molded with the flexible material such that all components of device 350 are sealed from the external environment by package 366.

Device 350 is a wearable device having two way communication, operable at two or more different frequencies, has the capability of providing radio frequency energy to a batteryless device, can receive radio frequency energy to charge battery 360, and is conformable to be placed on a non-planar surface. In the example, device 350 is a medical device configured to couple to the musculoskeletal system to monitor position, relative position, measure one or more parameters with one or more sensors, or to support healing, therapy, or rehabilitation. In one embodiment, device 350 can provide approximately 10 milliamps of current to charge a device or screw. The size of device 350 is about the size of a band aid. For example, it can be attached to the skin. In one embodiment, device 350 has an adhesive system. The adhesive system is applied to second side 354 of device 350. The adhesive system has a cover that is removed prior to using device 350. Removing the cover exposes an adhesive layer of a medical grade adhesive. In one embodiment, the adhesive layer couples device 350 to the skin of a patient. Device 350 can flex and change shape as the skin is changes contour under normal use. The adhesive layer supports holding device 350 to the skin but also allows removal of device 350 similar to a bandage. In one embodiment, an area of device 350 is less than 25 millimeters by 47.5 millimeters. Device 350 has a thickness of less than 4 millimeters. Device 350 is hermetically sealed so it can operate in a wet environment and can be removed at any time. Alternatively, device 350 or multiples of device 350 can be placed in a band that can be coupled to an object. For example, the band can be a wrap having several of devices 350 within the band that is placed around the knee region to locate the devices on a surface of the leg at predetermined locations.

Figure 12:
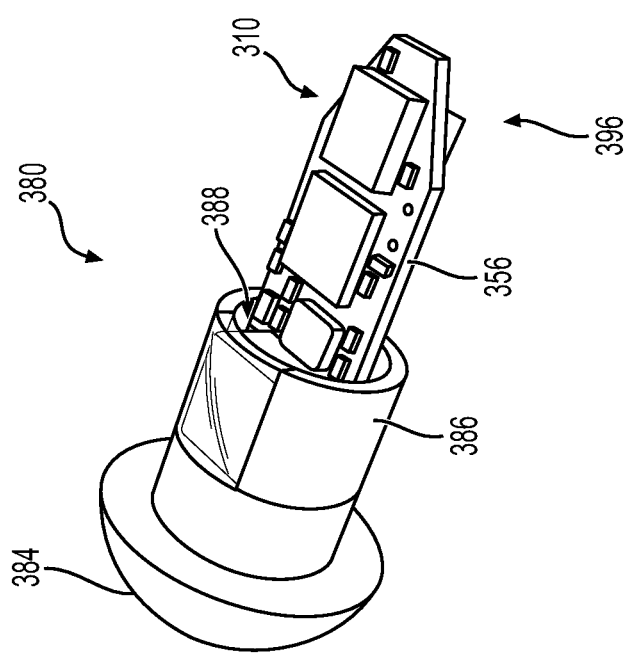
FIG. 12 is an illustration a partial view of a subcutaneous screw in accordance with an example embodiment.

FIG. 12 is an illustration a partial view of a subcutaneous screw 380 in accordance with an example embodiment. Subcutaneous screw 380 is a device having no internal power source such as a battery and requires power from another source prior to being enabled. A threaded section of subcutaneous screw 380 is removed to illustrate electronic circuitry 310 therein. Subcutaneous screw 380 comprises a screw head 384, a screw body 386, module 396, a first antenna, and a second antenna. Module 396 is disclosed in FIG. 11 and comprises printed circuit board 356 and electronic circuitry 310 shown in FIG. 10. The electronic circuitry 310 is interconnected on a printed circuit board 356 to allow subcutaneous 380 to receive one or more radio frequency signals that is converted to a DC voltage that powers subcutaneous screw 380. In one embodiment, the first and second antennas are formed on printed circuit board 356. In one embodiment, modules 356 in FIG. 10 and FIG. 11 can have different sensors configured to measure different parameters. Subcutaneous screw 380 tracks position and movement, can measure one or more parameters using one or more sensors, and can perform two way communication with another device. In one embodiment, subcutaneous screw 380 receives power from a device such as device 350 of FIG. 11 that can be placed in proximity to subcutaneous screw 80.

In one embodiment, screw head 384 comprises metal while screw body 386 comprises a polymer material. Screw body 386 has a cavity 388 in which electronic circuitry 310 and printed circuit board 356 is retained. In one embodiment, a potting material placed in cavity 388 can retain and hold the printed circuit board 356 in place to prevent movement. Screw body 386 is transmissive to radio frequency signals thereby allowing two way communication. Conversely, the metal of screw head 384 is an electrically conductive material. In one embodiment, screw head 384 is coupled to the ground of electronic circuitry 310, a terminal of the first antenna and a terminal of the second antenna. Screw head 384 can couple to screw body by many different methods. For example, screw head 384 can be held by adhesive to screw body 386. Alternatively, screw head 384 can be mechanically fastened to screw body 386 by threads or fastening structure.

Referring briefly to FIGS. 1-7, different types of devices are shown that include two way communication, one or more sensors, or one or more devices to provide therapy, improve health, or support rehabilitation. The devices of FIGS. 1-7 can include electronic circuitry 310, printed circuit board 382, the first antenna, and the second antenna as shown in FIG. 12. In the example, the first and second antennas are formed on printed circuit board 356. In particular, different types of screws for the musculoskeletal system are proposed for generating measurement data and two way communication. Some of the screws have cavities in the body of the screw in which module 356, the first antenna, and the second antenna can be placed. Alternatively, some embodiments show module 396, the first antenna, and the second antenna being placed in a washer or the head of the screw. It should be noted that the first antenna and the second antenna need to be housed in a material transmissive to radio frequency signals. A portion of the screws or devices of FIGS. 1-7 comprise a conductive material to be a ground for electronic circuitry 310, a terminal of the first antenna, and a terminal of the second antenna.

Figure 13:
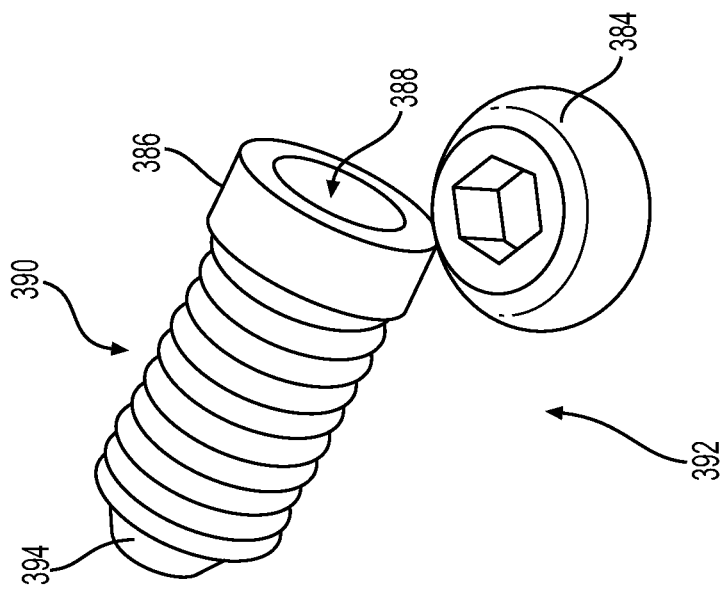
FIG. 13 is an illustration of a screw housing in accordance with an example embodiment.

FIG. 13 is an illustration of a screw housing 392 in accordance with an example embodiment. Screw housing 392 is the complete housing for screw 380 of FIG. 12. Screw head 384 comprises an electrically conductive material and couples to electronic circuitry 310, the first antenna, and the second antenna of FIG. 12. Screw body 386 comprises a non-electrically conductive material (such as plastic or a polymer) and includes a threaded region 390 and a tip 394. In one embodiment, subcutaneous screw 380 can have a length of 39.5 millimeters and an outside diameter of 11 millimeters. In one embodiment, cavity 388 has a diameter of 7 millimeters and length of 28.4 millimeters in screw body 386. Screw head 384 couples to screw body 386 hermetically sealing cavity 388. In one embodiment, a bone of the musculoskeletal system is drilled and tapped having corresponding threads as screw body 386. In the example, an Allen headed wrench is coupled to screw head 384 to rotate screw body 386 into the drilled and tapped bone. In one embodiment, screw housing 392 can be removed from the musculoskeletal system in a minimally invasive procedure.

Figure 14:
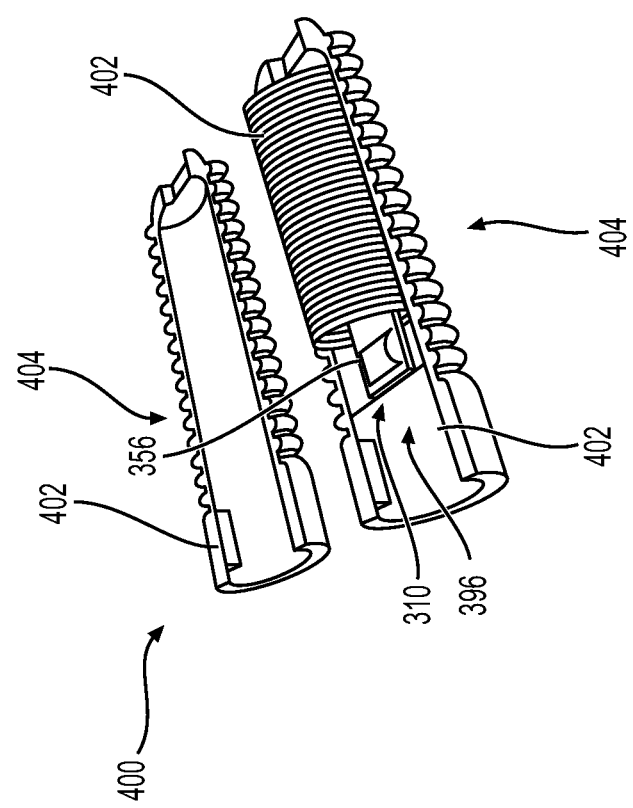
FIG. 14 is an illustration of a partial screw in accordance with an example embodiment.

FIG. 14 is an illustration of a partial screw 400 in accordance with an example embodiment. Partial screw 400 includes a screw body 402 comprising a first half and a second half. In one embodiment, screw body 402 when coupled together has a cavity for receiving module 356 and coil antenna 402. Screw body 402 comprises a non-electrically conductive material such as a plastic or polymer that is transmissive to radio frequency signals. Screw body 402 further includes a threaded section 404 configured to couple to the musculoskeletal system for placement of partial screw 400. Not shown is a screw head of partial screw 400. The screw head comprises couples to screw body 402 by adhesive, mechanical coupling, welding, or both. The screw head is an electrically conductive material that is used as a ground for electronic circuitry 310, printed circuit board 356, coil antenna 402, and a second antenna. Alternatively, a tip can be coupled to screw body 402. The tip can comprise an electrically conductive material that is used as a ground for electronic circuitry 310, printed circuit board 356, coil antenna 402, and a second antenna.

In one embodiment, the interior cavity of screw body 402 is cylindrical. The cylindrical cavity is configured to fit and retain coil antenna 402. Coil antenna 402 is used to improve the energy transfer to partial screw 400. In one embodiment, coil antenna 402 is optimized for a first frequency operating below 1 gigahertz that is used to penetrate skin and fluids of a patient when partial screw 400 is coupled within a bone. It has been shown that coil antenna 402 is capable of generating 10 milli-amperes of current when harvesting a radio frequency signal less than 1 gigahertz using a device such as device 350 of FIG. 11 placed on the skin in proximity to partial screw 400. The current is sufficient to rapidly charge and enable module 396 in 10 seconds or less for providing position or motion data and measuring one or more parameters. The harvested current will also enable module 396 to take continuous measurements and transmit measurement data. In one embodiment, the second antenna is formed on printed circuit board 356 to support Bluetooth communication.

Figure 15B:
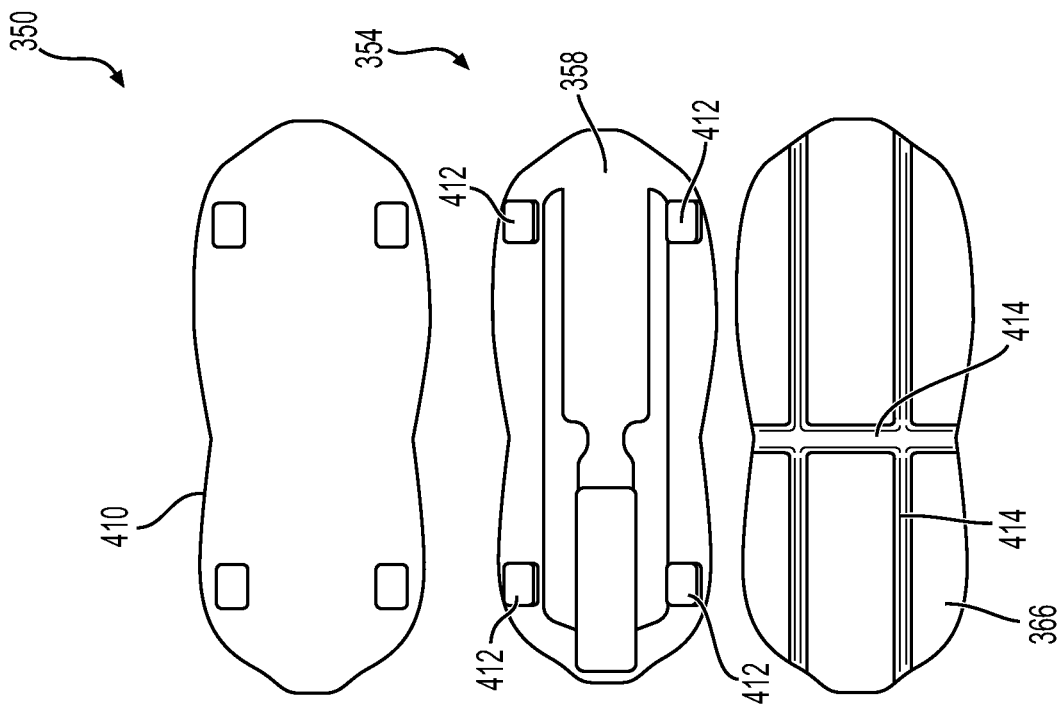
FIG. 15B is an exploded view of the device with the plurality of sensors configured to measure one or more parameters in accordance with an example embodiment.
Figure 15A:
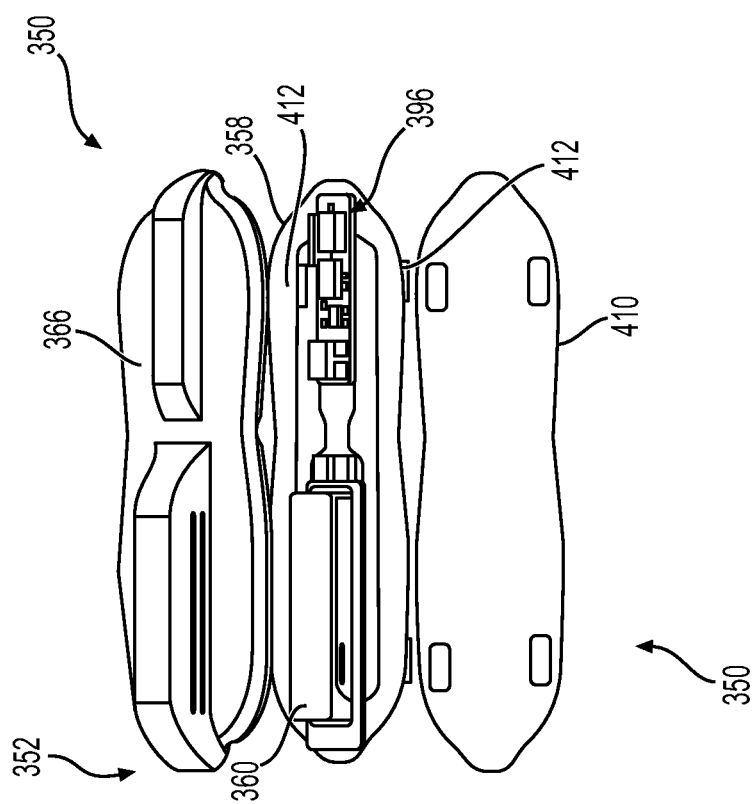
FIG. 15A is an exploded view of the device with a plurality of sensors configured to measure one or more parameters in accordance with an example embodiment.

FIG. 15A is an exploded view of device 350 with a plurality of sensors 412 configured to measure one or more parameters in accordance with an example embodiment. Device 350 is shown from first side 352 perspective. Device 350 comprises module 396, flexible printed circuit board 358, and battery 360. In one embodiment, a plurality of sensors 412 couple to flexible printed circuit board 358. Alternatively, sensors 412 can be devices for providing therapy, health improvement, or rehabilitation. Interconnect on flexible printed circuit board 358 couples plurality of sensors 412 to module 396. Package 366 hermetically seals module 396, battery 360, and flexible printed circuit board 358 from an external environment. In one embodiment, plurality of sensors 412 are exposed to the external environment for taking measurements. An adhesive system 410 couples to package 366 on the second side that is not shown. In one embodiment, adhesive system 410 is a medical grade film adhesive and cover configured to adhere to skin or other objects. Adhesive system 410 has a removable cover that protects the adhesive until device 350 is used. Although not shown, package 366 forms an enclosure completely around module 396, battery 360, and flexible printed circuit board 358. Adhesive system 410 couples to the underside of package 366. Adhesive system 410 can be a double sided adhesive to couple to the underside of package 366 or be coupled to package 366 with an adhesive. In the example, plurality of sensors 412 is exposed to the environment. Package 366 is formed around plurality of sensors 412 such that a surface of each sensor 412 is exposed for measurement. Similarly, adhesive system 410 has cut outs that leave the surface of plurality of sensors 412 exposed.

FIG. 15B is an exploded view of device 350 with a plurality of sensors 412 configured to measure one or more parameters in accordance with an example embodiment. Device 350 is shown from the second side 354 perspective corresponding to an underside of package 366. Adhesive system 410 couples to package 366. In one embodiment, adhesive system 410 is a double-sided film adhesive having one side coupled to the underside of package 366. The exposed side of the double sided film adhesive can have a removable cover that protects the adhesive until device 350 needs to be attached to a surface. As mentioned previously, package 366 will be formed around plurality of sensors 412 such that a surface or surfaces of plurality of sensors 412 is exposed to the external environment to which device 350 is coupled. Similarly, adhesive system 410 has cutouts for plurality of sensors 412 that allow exposure of plurality of sensors 412 to the external environment. In one embodiment, package 350 on second side 354 is grooved. As shown, grooves 414 are vertical and horizontal on the surface of package 366. The grooves support flexing of device 350 to support coupling to a non-planar surface. Coupling to a non-planar surface supports placement of plurality of sensors 412 in locations to provide accurate measurement data.

Figure 15C:
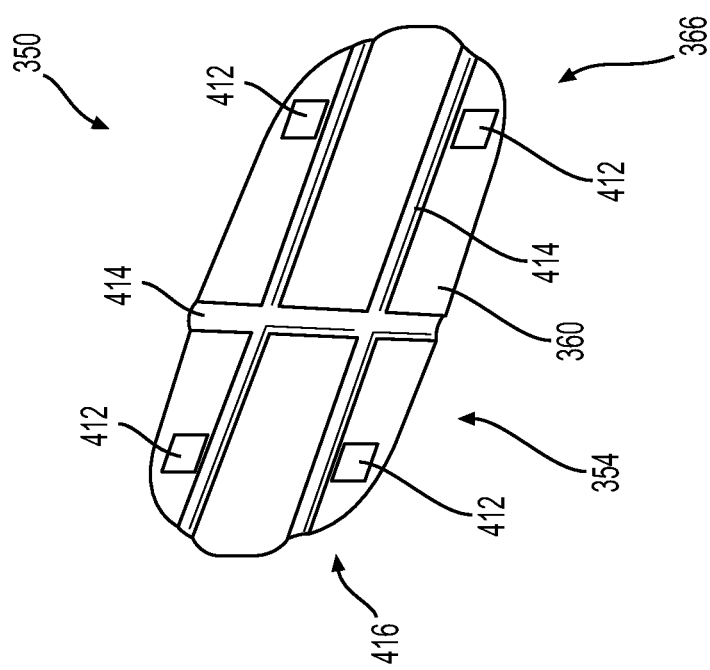
FIG. 15C is a view of an underside of the device with the plurality of sensors exposed for measurement to an external environment in accordance with an example embodiment.

FIG. 15C is a view of an underside of device 350 with plurality of sensors 412 exposed for measurement to an external environment in accordance with an example embodiment. In one embodiment, adhesive system 410 as shown in FIG. 15B supports coupling of device 350 to a non-planar surface. Plurality of sensors 412 can be the same sensor or different sensors depending on the application. Plurality of sensors 412 can also be devices configured to provide therapy, health improvement, or rehabilitation. Although plurality of sensors 412 are shown placed in different quadrants of a sensing surface 416 of device 350 they can be located where needed on sensing surface 416 as dictated by the application. There can also be more or less sensors on device 350. In one embodiment, device 350 is powered by an internal battery. Device 350 is configured to receive and transmit information including measurement data from plurality of sensors 412. In one embodiment, the internal battery is a rechargeable battery that can be charged by receiving one or more radio frequency signals. As mentioned previously, device 350 can be capable of communication via Zigbee, Bluetooth, Bluetooth Low Energy, Wifi, Wimax or other communication standards. In the example, device 350 communicates using Bluetooth. In one embodiment, the Bluetooth transceiver in device 350 is capable of connecting to two or more Bluetooth devices. Thus, multiple devices can be providing radio frequency energy for harvesting by device 350 for charging the rechargeable energy or using the energy for operation. In general, any signal received by the antennas by device 350 will be harvested for energy.

In one embodiment, device 350 can be used as a wound monitor. One or more of plurality of sensors 412 can comprise a camera. Device 350 can be coupled to the skin of a patient to protect the wound from an external environment. Device 350 prevents air or contaminants from entering between the adhesive system and the surface to which device 350 is coupled. Device 350 can transmit pictures taken by the camera or cameras of the wound to a healthcare team, patient, Doctor, or Surgeon to assess the wound status. Alternatively, the pictures of the wound can be run through a program configured to determine if the wound is not healing property. In one embodiment, changes to the wound could be determined over time using pictures taken at periodic intervals. The program could send an alert to appropriate people if the changes do not indicate improving or healing of the wound. Thus, the issue could be addressed in a timely fashion to prevent a more catastrophic outcome. Other sensors but not limited to a temperature sensor, a pH sensor, humidity, pressure, or a chemical sensor can be used to further support monitoring the wound by providing further information related to the wound status. Further benefit can be provided by device 350 by not only monitoring the wound but support healing of the wound area. For example, plurality of sensors 412 can comprise photo diodes, ultra violet diodes, transducers, light emitting diodes, or photo detectors. The wound area can be irradiated by specific frequencies of light or sound waves to support healing and reduce recovery time. Other types of sensors could be added or used to provide different therapies to support wound healing or maintenance.

In one embodiment, device 350 can be used in an electrocardiography system. Plurality of sensors 412 can comprise one or more electro-cardiogram electrodes. Electro-cardiogram electrodes detect electrical activity generated by heart muscle depolarizations that generate pulsating electrical waves that are received at the skin. The signal level of the pulsating electrical waves can be in the microvolt range. In one embodiment, four or more devices 350 are used each coupled to a different location around the heart. For example, a device 350 could be placed around the heart in the chest area at four locations. Alternatively, a device 350 could be placed at each extremity such as right arm, left arm, right leg, and left leg to measure the pulsating electrical waves. As mentioned herein above, device 350 has medical grade tape that will stick to the skin of a patient. Each device 350 used in an electro-cardiogram can connect to a computer via Bluetooth (or other wireless methodology) and transmit the measurement data in real-time from each location. Thus, a wireless electro-cardiogram system can be provided using device 350.

In one embodiment, device 350 can be adapted for photo-plethysmography. Device 350 can measure heart rate, inter-beat interval, heart-rate variability to name a few parameters of interest. Plurality of sensors 412 can comprise optical sensors, photo diodes, or light emitting diodes. For example, the adhesive on device 350 can be used to place plurality of sensors around a fingertip which has substantial capillary tissue. In one embodiment, light from a light emitting diode of plurality of sensors 412 from device 350 is transmitted into the tissue of the finger. The light is either absorbed or reflected to a photo diode also of plurality of sensors 412 from device 350. In one embodiment, the photo diode is used to determine the amount of light reflected or absorbed. The measurement data can be transmitted via Bluetooth (or other wireless methodology) to determine the heart rate. As mentioned previously, device 350 is conformable to a non-planar surface. Thus, device 350 can be wrapped around a finger and held in place by the medical grade adhesive. Device 350 can then be removed after the measurements have been completed.

Figure 16:
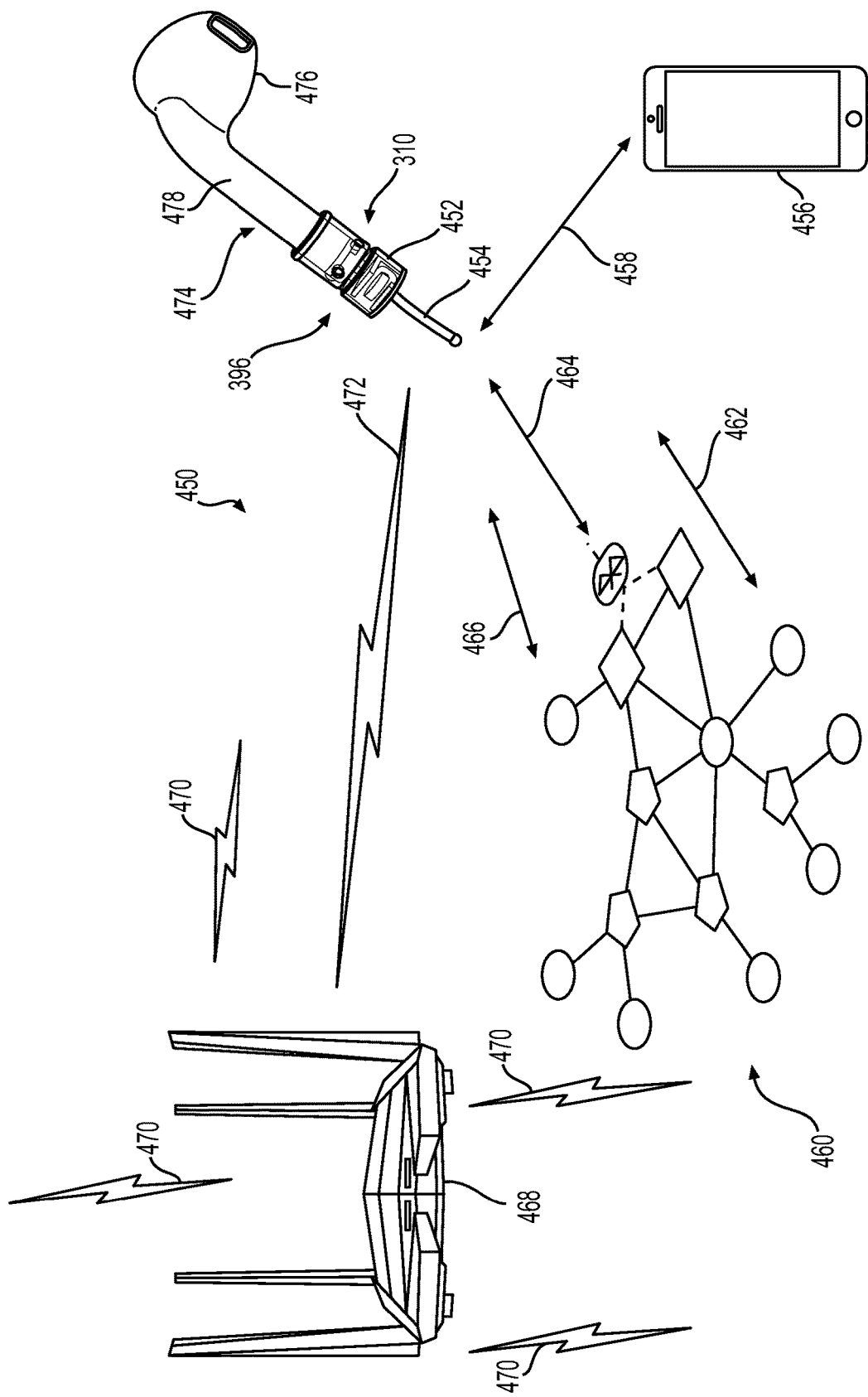
FIG. 16 is an illustration of a system using the electronic circuitry configured to charge a device in accordance with an example embodiment.

FIG. 16 is an illustration of a system 450 using electronic circuitry 310 configured to charge a device in accordance with an example embodiment. In general, a device is any battery operated component configured for radio frequency communication. In one embodiment, a battery in the device should be chargeable with approximate 10 milliamperes of current while in use. In other words, there would be a net gain in charge of the battery even if the device was being used. For example, many devices having an internal battery such as a laptop computer or a cell phone that requires 0.5-1.0 amperes of current to charge may not benefit from electronic circuitry 310. Conversely, other battery operated devices that communicate via Bluetooth, Zigbee, or other low power communication technology are likely candidates for using electronic circuitry 310 of FIG. 10 or module 396 of FIG. 11 as they will use less than 10 milliamperes of current in normal usage. As an example, a device 474 is configured with communication circuitry such as Wifi, Wimax, Bluetooth, Zigbee, or other radio frequency communication circuitry. As a non-limiting example or system 450, device 474 is an earpiece coupled to a cellphone 456 via Bluetooth.

System 450 is used to disclose multiple methodologies to generate sufficient current using module 396 and electronic circuitry 310 to charge device 474. System 450 comprises a Wifi router 468, one or more Bluetooth devices, cell phone 456, and device 474. In one embodiment, device 474 is in direct communication via Bluetooth handshake to cell phone 456. Device 474 can be in use or in standby waiting to communicate with cell phone 456. A typical use of device 474 is to watch some form of content on cell phone, device 474 is coupled to an ear of a user, audio corresponding to the content is transmitted to device 474 and converted to audible sound on device 474 to be received by a user's ear. Alternatively, device 474 can be in standby mode and will be awakened by cell phone 456 to respond to an action such as receiving a phone call.

In a typical environment there are other local systems that may be in communication with other devices or available for connecting to cell phone 456 or device 474. In the example, router 468 is a Wifi system that is a wireless local area network configured for coupling to the internet using I.E.E.E. standard 802.11. In one embodiment, router 468 transmits a Wifi signal in all different directions as indicated by radio frequency signals 470. In one embodiment, Wifi system can include beam forming. Router 468 has spatial filtering that supports directional signal transmission. Router 468 is shown transmitting a stronger radio frequency signal 472 in a direction towards device 474 than the radio frequency signals 470 being transmitted away from device 474. Bluetooth system 460 represents interconnected or individual devices coupled together or paired with other devices for communicating over short distances. In one embodiment, device 474 is a Bluetooth Low Energy device capable of coupling to two or more Bluetooth devices simultaneously. Similarly, Wimax, Zigbee, or other networks could also be present where device 474 is located. As shown, device 474 can be in an environment rich in radio frequency signals.

Device 474 is adapted for harvesting radio frequency energy using electronic circuitry 310 or module 396. A housing 452 includes electronic circuitry 310 that is readily adapted for use with existing battery operated device or new battery operated wireless devices. In general, the wireless technology or technologies are chosen for the device such as Wimax, Wifi, Bluetooth, Bluetooth Low Energy, Zigbee, or other radio frequency communication. In the example, device 474 is configured to receive Bluetooth and Wifi radio signals and includes antennas coupled to electronic circuitry 310. In the example of device 474 being a Bluetooth headset, device 474 comprises a speaker housing 476, a stem 478 extending from speaker housing, and a housing 452. Speaker housing 476 fits and retains device 474 in the Concha of the ear. The interconnection of electronic circuitry 310 is modified to fit in the cylindrical form factor of housing 452 that extends from the speaker housing. Although housing 452 is shown fitted to stem 478 the circuitry therein can be placed anywhere within device 474 that supports coupling to antenna 454. In one embodiment, housing 452 of stem 478 extends away from the ear such that antenna 454 is free to receive radio frequency signals. As mentioned previously, electronic circuitry 310 couples to at least one antenna and can couple to two or more antennas depending on the radio frequencies being harvested.

The following are method steps for harvesting energy to charge a battery in device 474 in accordance with an exemplary embodiment. The method can be practiced with more or less than the steps shown, and is not limited to the order of steps shown. The method steps correspond to FIG. 16 to be practiced with the aforementioned components or any other components suitable for such harvesting of radio frequency energy. In a first step, device 474 is coupled for two way communication to a cell phone 456 or other device as indicated by double headed arrow 458. In one embodiment, device 474 couples uniquely to cell phone 456 using a Bluetooth hand shake. The Bluetooth radio frequency signal transmitted from cell phone 456 can be harvested continuously to charge the battery within device 474. In a second step, device 474 can request an increase in transmit power from cell phone 456. Cell phone 456 may not automatically support the request depending on its own battery status or if it is being charged. Increasing the transmit power to device 474 from cell phone 456 can greatly extend operation of device 474 or maintain the battery of device 474 at full charge.

In a third step, device 474 can request coupling to one or more Bluetooth devices of Bluetooth system 460. As mentioned previously, device 474 has the ability to connect to two or more Bluetooth devices. In one embodiment, device 474 can request coupling via Bluetooth hand shake to harvest energy such that no communication occurs other than the hand shake. Bluetooth devices in proximity to device 474 that are powered by a power supply or have a large power reserve can respond by providing power to device 474. In one embodiment, the time period in which device 474 can be allowed to harvest can be a predetermined time. Alternatively, devices of Bluetooth system 460 can couple to device 474 for communication purposes. If so, electronic circuitry 310 will still harvest the energy. Multiple devices of Bluetooth system 460 coupling to device 474 is indicated by double headed arrows 462, 464, and 466.

In a fourth step, device 474 can request coupling to Router 468. In one embodiment, beam forming is used to send a radio frequency signal of higher strength to support charging the battery of device 474. In one embodiment, device 474 can be simultaneously coupled through Bluetooth and Wifi. Router 468 may not have beam forming capability. In a fifth step, device 474 can request an increase in transmitting power. Typically, systems are optimized to minimize the transmit power. In one embodiment, the requirement to minimize power is over ridden by the request from device 474 for increased transmit power. The energy from the radio frequency signal transmitted by router 468 is harvested to maintain operation of device 474 and charge the battery of device 474.

As mentioned previously, device 474 can be in a radio frequency signal rich environment. In a sixth step, device 474 does not need to couple via a hand shake to a system such as router 468 or Bluetooth system 460 if the radio frequency signals are received by the one or more antennas of device 474. In one embodiment, the radio frequency signals have to be above a predetermined power to harvest the energy. This is the case whether connected by hand shake or receiving a radio frequency signal without a hand shake. In one embodiment, receiving one or more radio frequency signals greater than 100 milliwatts (20 dBm) at the transceiver input of electronic circuitry 310 will initiate a battery charging process in device 474.

Figure 17:
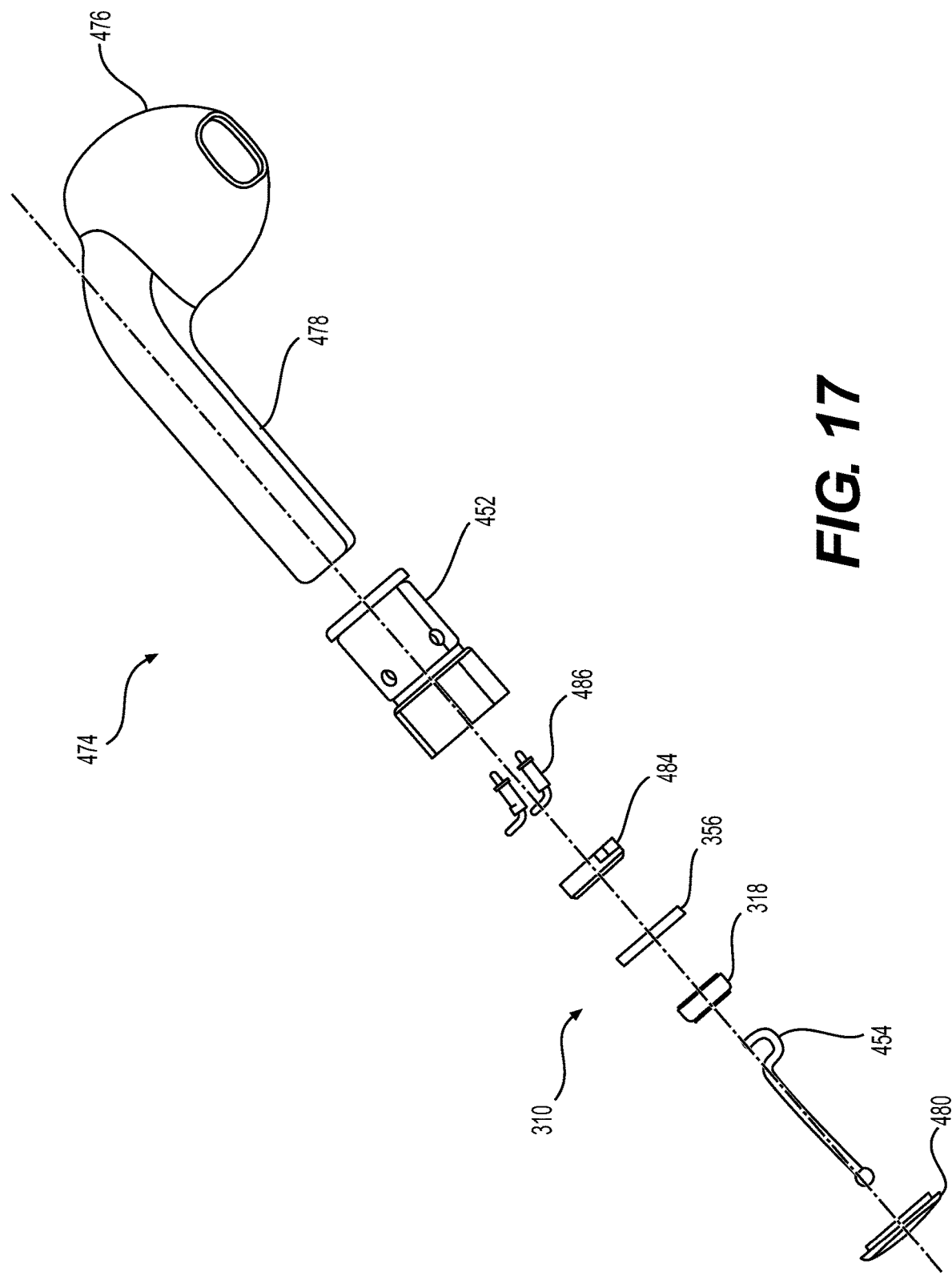
FIG. 17 is an exploded view of the device in accordance with an example embodiment.

FIG. 17 is an exploded view of device 474 in accordance with an example embodiment. In general, electronic circuitry 310 of FIG. 10 and printed circuit board 356 is shown in a form factor that fits within device 474. In the example, device 474 is an earpiece configured to couple to another device for receiving information such as audio content through a radio frequency transmission. Device 474 is not limited to an earpiece but can be any electronic system configured to receive radio frequency communication. Device 474 can be a batteryless device that is powered by energy harvest from the radio frequency transmission. Alternatively, device 474 can be a device having energy storage such as a battery that can be recharged by the radio frequency transmission. In both examples the system should operate or be capable of recharging with a current of 15 milli-amperes or less. In one embodiment, approximately 10 milli-amperes can be generated for operation or charging at distances of 3 feet or less.

Device 474 comprises housing 452, housing cover 480, antenna 454, super capacitor 318, printed circuit board 356, pin holder 484, and a plurality of pins 486. Electronic circuitry 310 fits within housing 352 that couples to stem 478 of device 474. Speaker housing 476 is designed to couple to an ear and provide audio to a user. In the example, speaker housing 476 houses a speaker and a rechargeable battery. Stem 478 of device 474 includes interconnect coupling the speaker and rechargeable battery to electronic circuitry 310. As disclosed in FIG. 10, printed circuit board 356 includes components for two way communication and harvesting radio frequency signals for energy. In the example, printed circuit board 356 utilizes Bluetooth or Bluetooth low energy circuitry for the two way communication. In the example, speaker housing 476 fits in and is retained by the concha of the ear such that the speaker is directed to and partially seals the ear canal. Stem 478 of device 474 places antenna 454 outside the ear in position to receive radio frequency signals. Alternatively, antenna 454 can be placed in housing 452 or step 478 to provide a smaller form factor.

In one embodiment, the components for radio frequency communication and radio frequency energy harvesting are fitted in housing 452 to maintain the form factor of stem 478 of device 474. Antenna 454 extends through an opening in housing cover 480. In one embodiment, antenna 454 has a curved shape at a proximal end that couples around super capacitor 318. The curved shape at the proximal end of antenna 454 retains antenna 454 within housing 452. Antenna 454 and super capacitor 318 couples to printed circuit board 356. Antenna 454 provides one or more radio frequency signals to device 474 and super capacitor 318 stores harvested radio frequency energy for powering device 474 or charging the battery within device 474. A plurality of pins 486 couple to printed circuit board 356. In one embodiment, the plurality of pins 486 are spring loaded pins that can compress. A pin holder 484 holds plurality of pins 486 in predetermined positions to printed circuit board 356. In one embodiment, housing 452 is cylindrical in shape. Printed circuit board 356 and pin holder 484 are circular in shape to fit within housing 452 and be retained. Pins 486 extend beyond pin holder 484. In one embodiment, a distal end of stem 478 includes interconnect pads configured to couple to the plurality of pins 486. In one embodiment, the interconnect pads couple to interconnect that extends through stem 478 to the speaker and the rechargeable battery within device 474. In one embodiment, housing 452 is pressed onto stem 478 of device 474. Plurality of pins 486 couple to corresponding interconnect pads within stem 478. As mentioned previously, plurality of pins 486 can compress to make contact to the corresponding interconnect pads under a force or pressure. Housing cover 480 couples to housing 452 to retain the components within housing 452. Thus, two way communication and radio frequency energy harvesting can be provided in a small form factor capable of powering or recharging device 474 while being used. Thus, electronic circuitry 310 can be adapted to an existing product for harvesting energy to charge a battery or built within the existing product. This provides the benefit of not requiring a charging station for the device as it can be charged by several different wireless methodologies as disclosed herein above while device 474 is in use or not in use.

Figure 18:
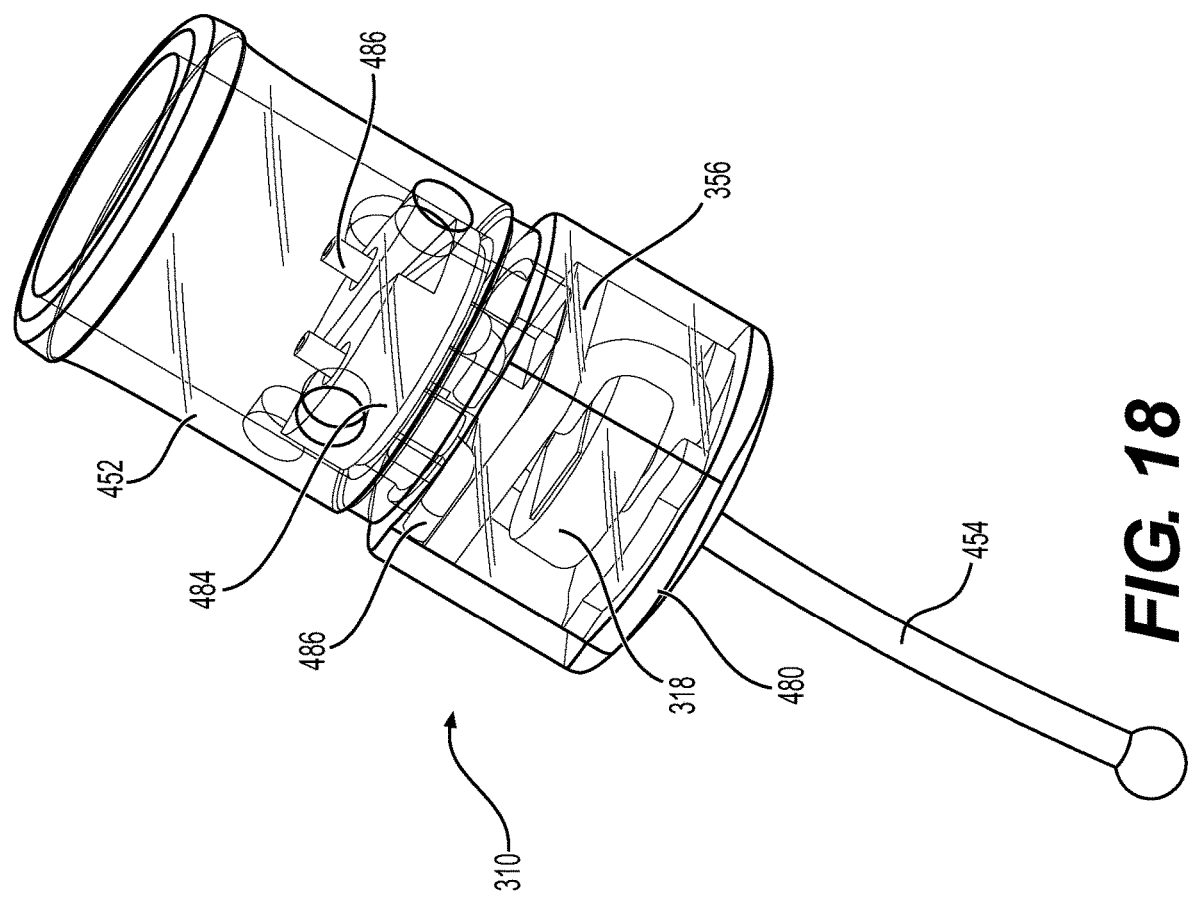
FIG. 18 is an illustration of the electronic circuitry placed in the housing that couples to the device of FIG. 17 in accordance with an example embodiment.

FIG. 18 is an illustration of electronic circuitry 310 placed in housing 452 that couples to device 474 of FIG. 17 in accordance with an example embodiment. Electronic circuitry 310 provides two way communication and energy harvesting of radio frequency signals to charge a battery or power a batteryless device. Plurality of pins 486 extend towards a proximal end of housing 452. In the example, each pin of plurality of pins can compress and apply a force to a corresponding contact or pad in stem 478 of FIG. 17. Plurality of pins 486 are held in place by pin holder 484. In one embodiment, plurality of pins 486 couple through pin holder 484 in predetermined positions. In one embodiment, pin holder 484 is retained within housing 452 by one or more retaining features. Plurality of pins 486 also extend through the distal end of pin holder 484 to couple to predetermined contact points or pads on printed circuit board 356. In one embodiment, a pin of plurality of pins 486 can be bent in a right angle as shown in FIG. 18 to provide more contact surface area and retain the distal portion of the pin on distal side of pin holder 484. Printed circuit board 356 has components mounted thereon and interconnect traces to electrically couple the components together as disclosed in FIG. 10 to form electronic circuitry 310. Electronic circuitry 310 is configured to provide two way communication and energy harvesting of radio frequency signals for powering device 474 or charging a power source within device 474. Printed circuit board 356 has a plurality of pads on a proximal surface that respectively couple to plurality of pins 486 extending from the distal side of pin holder 484. In one embodiment, an internal shape of housing 452 where printed circuit board 356 is located corresponds to the shape printed circuit board 356 to prevent movement or rotation. In the example, printed circuit board 356 is square or rectangular in shape. Antenna 454 and super capacitor 318 couples to a distal side of printed circuit board 356. The distal side of printed circuit board 356 includes a plurality of pads for coupling to super capacitor 318 and antenna 454. It should be noted that components of electronic circuitry 310 can be mounted on the proximal and distal sides of printed circuit board 356. In one embodiment, antenna 454 is curved to retain super capacitor 318 within housing 452. Housing cover 480 couples to the distal end of housing 452 to seal electronic circuitry 310 within housing 452. Antenna 454 extends through an opening in housing cover 480 and is positioned to receive radio frequency signals. Housing 486 is coupled to stem 478 of device 474 of FIG. 17 such that plurality of pins 486 couple to corresponding pads of stem 478 for coupling to the speaker and battery. Housing 486 is held in place compressing plurality of pins 486 under a compressive force that supports holding antenna 454, super capacitor 318, printed circuit board 356, pin holder 484, and plurality of pins 486 in place.

Figure 19:
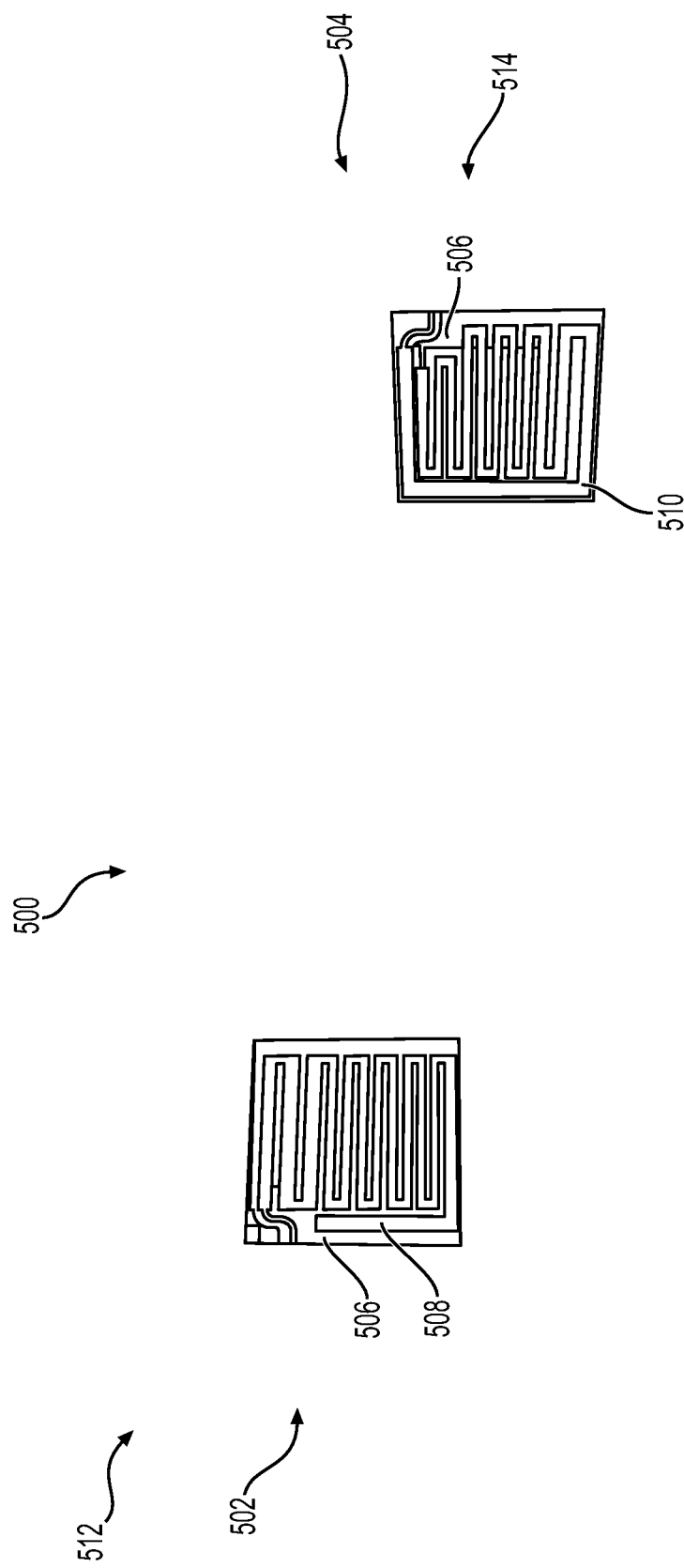
FIG. 19 is an illustration of two antennas formed on the same substrate in accordance with an example embodiment.

FIG. 19 is an illustration of two antennas formed on the same substrate in accordance with an example embodiment. Antennae 500 comprise a first antenna 512 and a second antenna 514. Antennae 500 is a dual band antenna that can be used with electronic circuitry 310 to harvest radio frequency energy at two different frequency bands. In the example, first antenna 512 is configured to operate at a lower frequency band than second antenna 514. In one embodiment, first antenna 512 is configured to operate at frequencies less than 1 gigahertz. Operating at frequencies less than 1 gigahertz supports radio frequency penetration through liquids and solids. For example, a radio frequency signal transmitted from an external environment having a frequency less than 1 gigahertz will be received by a screw embedded in the musculoskeletal system at a much higher signal strength than a 2.4 gigahertz signal being transmitted at the same power level. It has been shown that 10-15 milliamperes of current can be generated by electronic circuitry 310 of FIG. 10 within a screw or device receiving the radio frequency signal of less than 1 gigahertz by communicating with a transmitting device placed at or near a skin surface or within 3 feet of the screw. The 10-15 milliamperes of current is sufficient to power the screw having one or more sensors for taking quantitative measurements continuously. First antenna 512 operates at a frequency less than 1 gigahertz such as an ISM (industrial, scientific, and medical band). Second antenna 514 operates at a higher frequency such as 2.4 gigahertz and uses Bluetooth, Bluetooth low energy, Wifi, Zigbee, Wimax or other communication protocols that have been standardized for transferring data. First antenna 512, second antenna 514, or both can be used for energy harvesting to generate the 10-15 milliamperes.

Antennae 500 is designed to have a predetermined efficiency, predetermined gain, and form factor for use in an energy harvesting application for transmitting or receiving a radio frequency signal. In the example, first antenna 512 is configured to operate at 915 megahertz for transmit and receive functions using the ISM band. The second antenna 514 is configured to operate at 2.4 gigahertz using Bluetooth or Bluetooth low energy. Bluetooth is for short range communication having a maximum output power of 100 milliwatts (20 dBm) while an ISM transmission is higher power at 1 watt. First antenna 512 is formed on a first side 502 of antennae 500 on a dielectric substrate 506. Antenna 512 comprises a conductor 508 formed in a serpentine pattern on first side 502. Similarly, Second antenna 514 is formed on a second side 504 of antennae 500 on dielectric substrate 506. Antenna 514 comprises a conductor 510 formed in a serpentine pattern of second side 504. In one embodiment, first antenna 512 and second 514 are designed to minimize overlap of conductor 508 and 510 to maximize the efficiency of the antenna. It is found that overlapping conductors 508 and 510 produces interference that affects antenna performance.

FIG. 20 is a list of specifications for antennae 500 of FIG. 19 in accordance with an example embodiment. As mentioned previously, dual antenna 500 is formed on a polyimide dielectric substrate that is approximately 17.63 millimeters thick. The gain of each antenna is approximately 2.0 dBi. The efficiency was targeted for approximately 60% to ensure sufficient current could be generated to operate a batteryless device (e.g. 10-15 milliamperes continuous). Dual antenna 500 has a small form factor that is approximately 25 millimeters x 25 millimeters. The gap between two layer minimum is 0.4 millimeters. In one embodiment, each antenna of antennae 500 comprises a copper plated trace that is photolithographically etched to form the serpentine shape.

Figure 21:
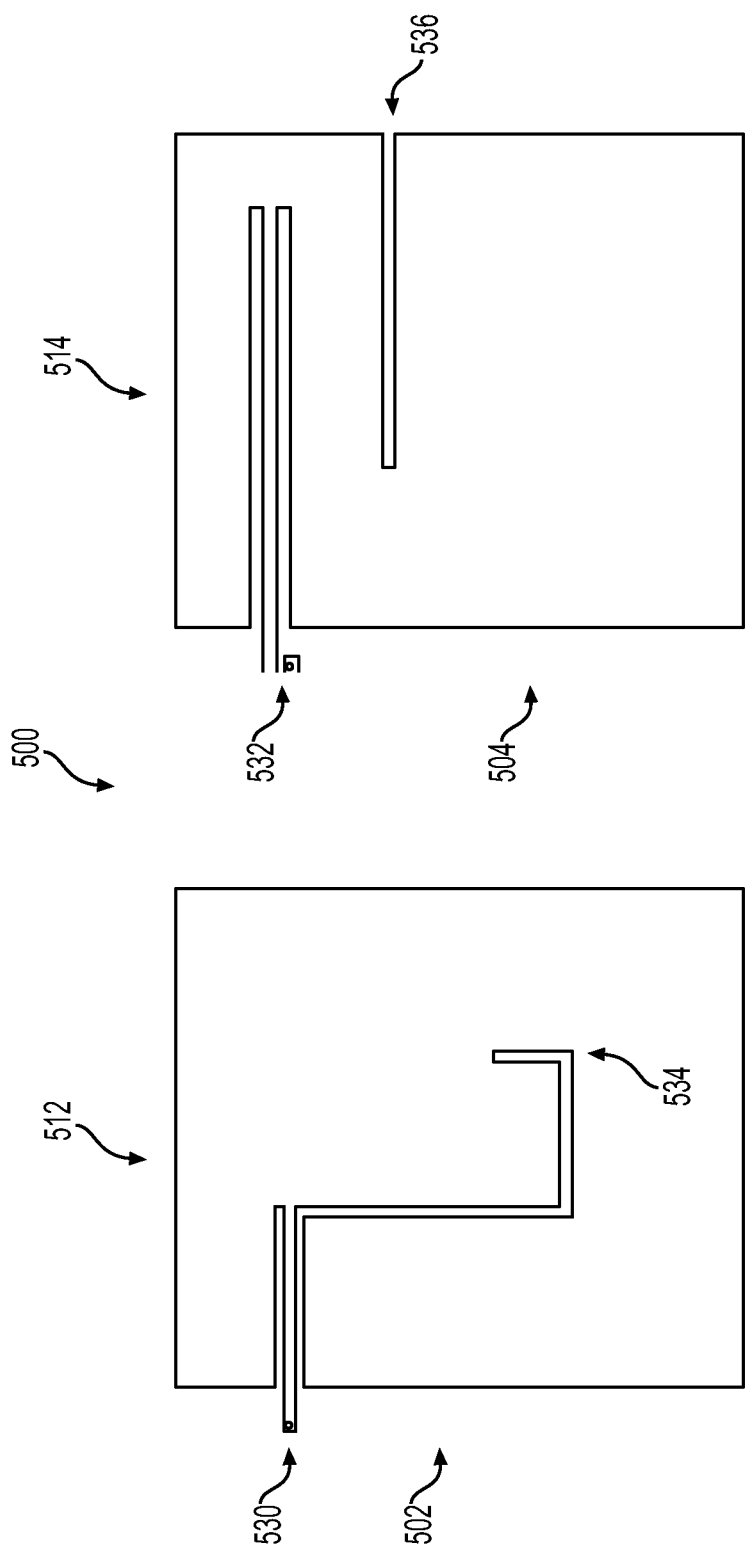
FIG. 21 is an illustration of impedance tuning and frequency tuning of the antennae of FIG. 19 in accordance with an example embodiment.

FIG. 21 is an illustration of impedance tuning and frequency tuning of antennae 500 of FIG. 19 in accordance with an example embodiment. A first side 502 of antennae 500 illustrates impedance tuning and frequency tuning for 915 megahertz. Impedance tuning 530 of first antenna 512 is achieved by adjusting the length of the slot. Frequency tuning 534 is achieved by adjusting the height of the slot. In one embodiment, the impedance of first antenna 512 is 50 ohms. Similarly, second side 504 of antennae 500 illustrates impedance tuning and frequency tuning for 2.4 gigahertz. Impedance tuning 532 of second antenna 514 is achieved by adjusting the length of the slot. Frequency tuning 536 is achieved by adjusting the length of the slot as shown. In one embodiment, the impedance of second antenna 514 is 50 ohms.

Figure 22:
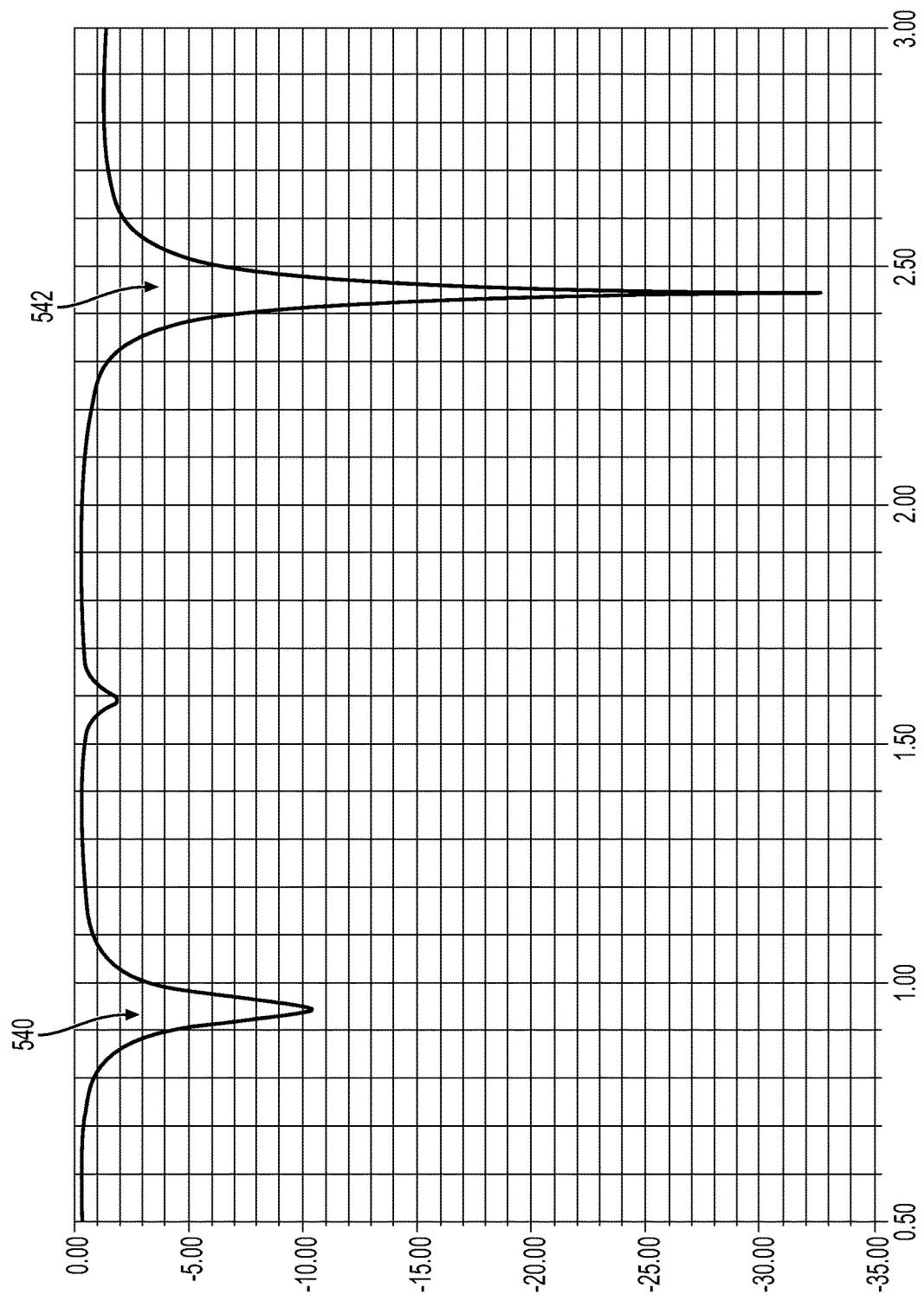
FIG. 22 is an illustration of a measurement of the antennae of FIG. 19 in accordance with an example embodiment.

FIG. 22 is an illustration of a measurement of antenna 512 and antenna 514 of FIG. 19 in accordance with an example embodiment. The measurement illustrates that antennae 500 of FIG. 19 can operate simultaneously with a high Q. The x-axis is frequency in gigahertz and the y-axis is the return loss. Tuning 542 is centered at approximately 2.4 gigahertz while tuning 540 is centered at approximately 915 megahertz. As mentioned previously, antenna 512 and antenna 514 can be operated simultaneously even though both are formed on the same substrate and operate within the same space.

Figure 23:
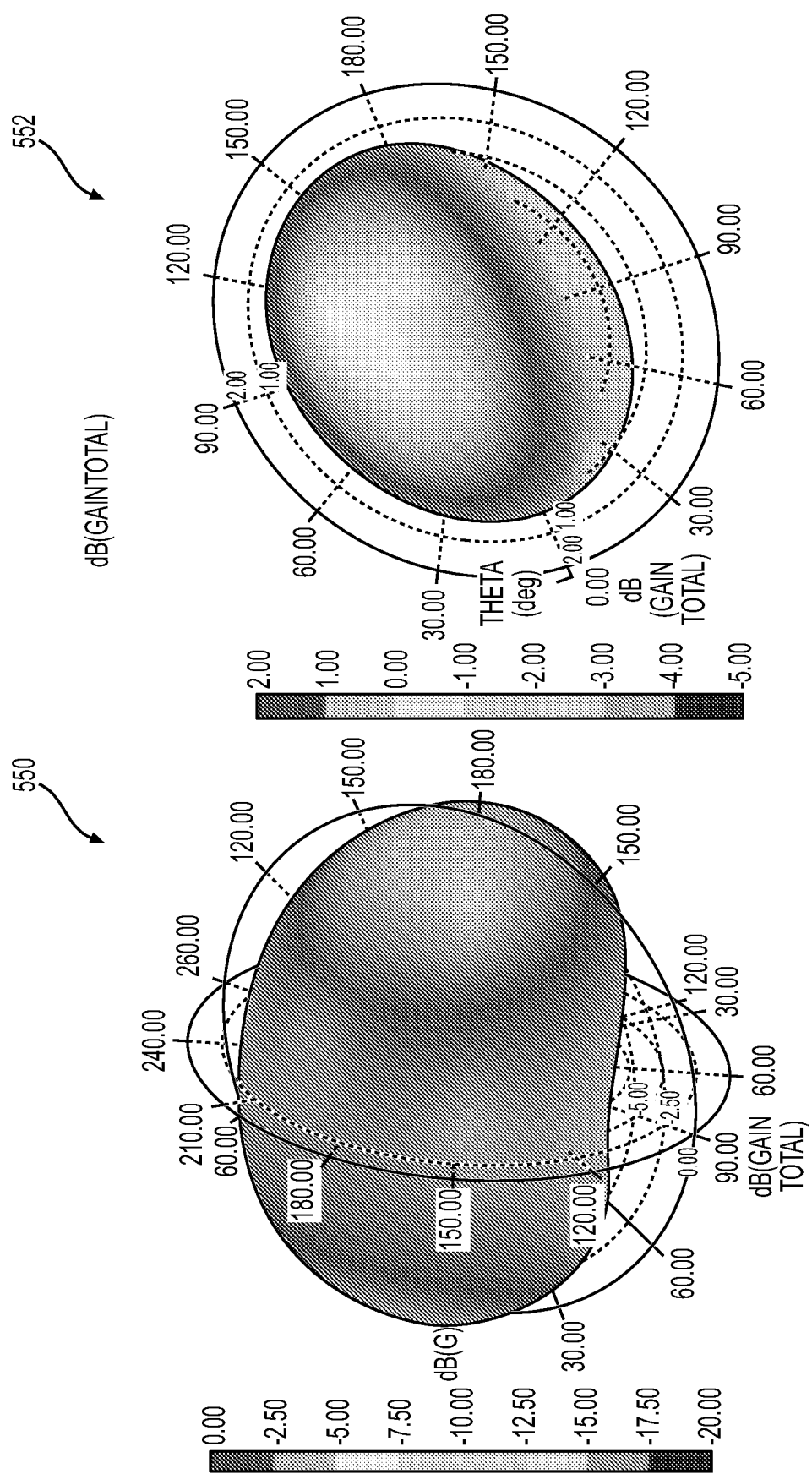
FIG. 23 is an illustration a radiation pattern for the antennae of FIG. 19 in accordance with an example embodiment.

FIG. 23 is an illustration a radiation pattern for antenna 512 and antenna 514 of FIG. 19 in accordance with an example embodiment. Radiation pattern 550 corresponds to antenna 512 operating at 915 megahertz. Radiation pattern 550 is an omni-directional pattern. Radiation pattern 552 corresponds to antenna 514 operating at 2.4 gigahertz. Similarly, radiation pattern 552 is an omni-directional pattern but having more directionality than radiation pattern 550. Thus, a dual antenna on a common substrate operating at two frequencies has been disclosed with omni-directional radiation patterns.

Figure 24:
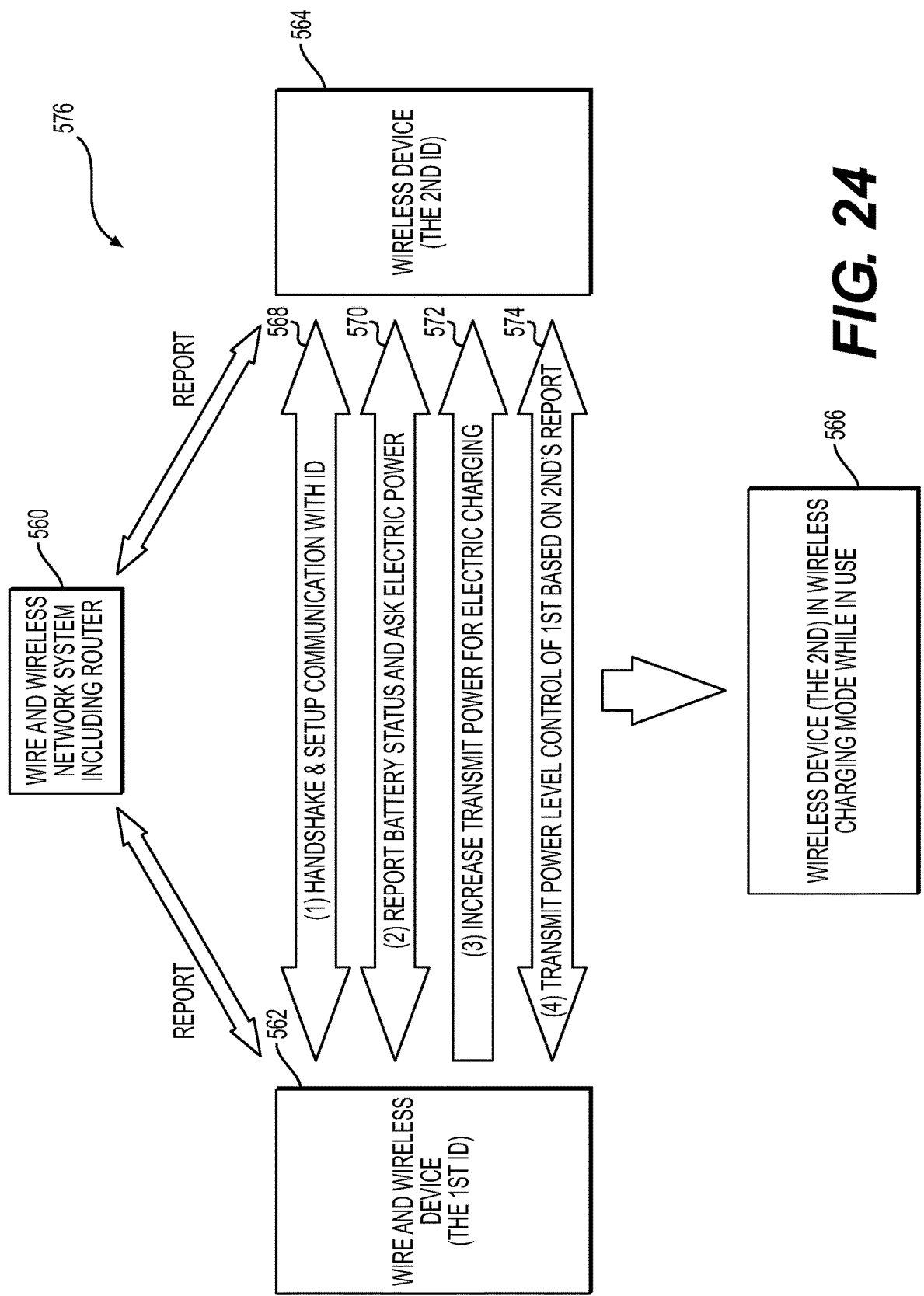
FIG. 24 is a block diagram of a system in accordance with an example embodiment.

FIG. 24 is a block diagram of a system 576 in accordance with an example embodiment. System 576 comprises two way communication between two or more devices. A network system 560 can be wired, wireless, or both. In one embodiment, network system includes a router for providing traffic control of information being sent between devices or the internet. System 576 includes a device 562 and a device 564. Device 562 and device 564 can be wired or wireless devices. Device 562 and device 564 can communicate through network system 560 or directly to each other.

In one embodiment, device 562 and device 564 can be configured to harvest energy from received radio frequency signals. In the example, device 564 is being used in an application that uses energy while harvesting radio frequency signals it receives as disclosed in box 566 to charge an energy source or provide power to maintain operation. In one embodiment, device 562 is in communication with device 564. In a step 568, device 562 and device 564 handshake and set up direct communication with identification. In a step 570, device 564 reports battery status to device 562. Device 564 requests power transfer for operation or to charge an internal battery from device 562. In a step 572, device 562 responds that it will transmit to support charging of device 564. Device 564 increases transmit power or transmits over multiple channels to support the power request. In a step 574, device 564 receives the radio frequency signal from device 562 and provides a report back to device 562 on the signal level or charging status. Device 562 can adjust the power level of the transmission based on the report from device 564. It should be noted that device 564 could also be receiving one or more radio frequency signals from network system 560 to further supplement powering of device 564 or charging a battery within device 564. The process of requesting and increasing the power of the transmission would be similar.

Figure 25:
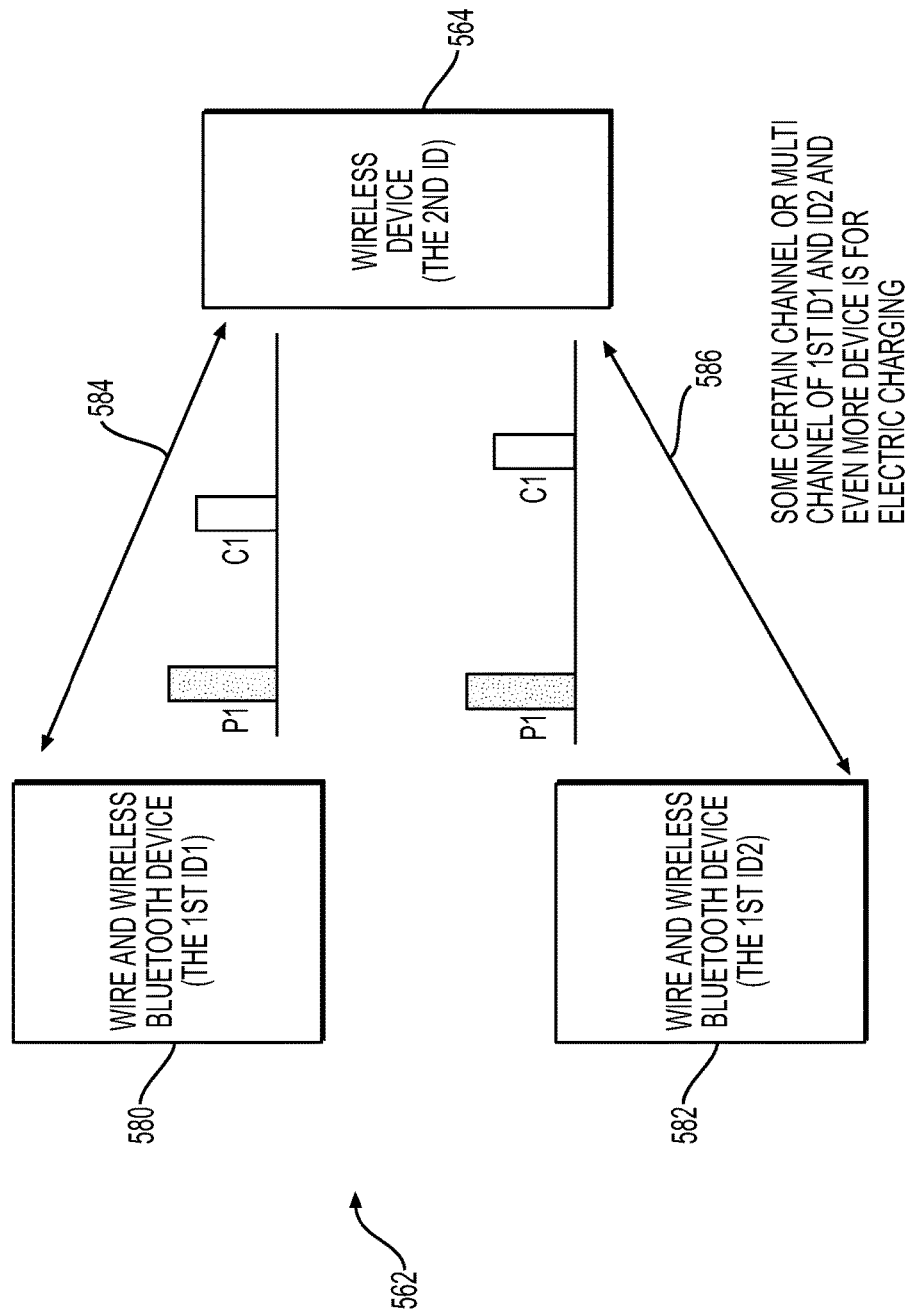
FIG. 25 is a block diagram illustrating two or more channels being transmitted from the devices of FIG. 24 in accordance with an example embodiment.

FIG. 25 is a block diagram illustrating two or more channels being transmitted from device 562 to device 564 in accordance with an example embodiment. In one embodiment, device 562 can transmit and receive with two or more channels. Similarly, device 564 can transmit and receive with two or more channels where each channel. In one embodiment, the energy harvested by device 564 can be increased by transmitting from device 562 through two or more channels. In the example, two channels are transmitted to device 564. In one embodiment, device 564 requests and handshakes with device 562. A channel 580 under an ID1 sends a radio frequency signal 584 that is received by device 564. Device 564 harvests the energy from radio frequency signal 584. In one embodiment, device 564 requests and handshakes with device 562 a second time. A channel 582 under an ID2 sends a radio frequency signal 586 that is received by device 564. Device 564 harvests the energy from radio frequency signal 586. Thus, the amount of energy that can be harvested can be increased by receiving radio frequency signals through multiple channels.

Figure 26:
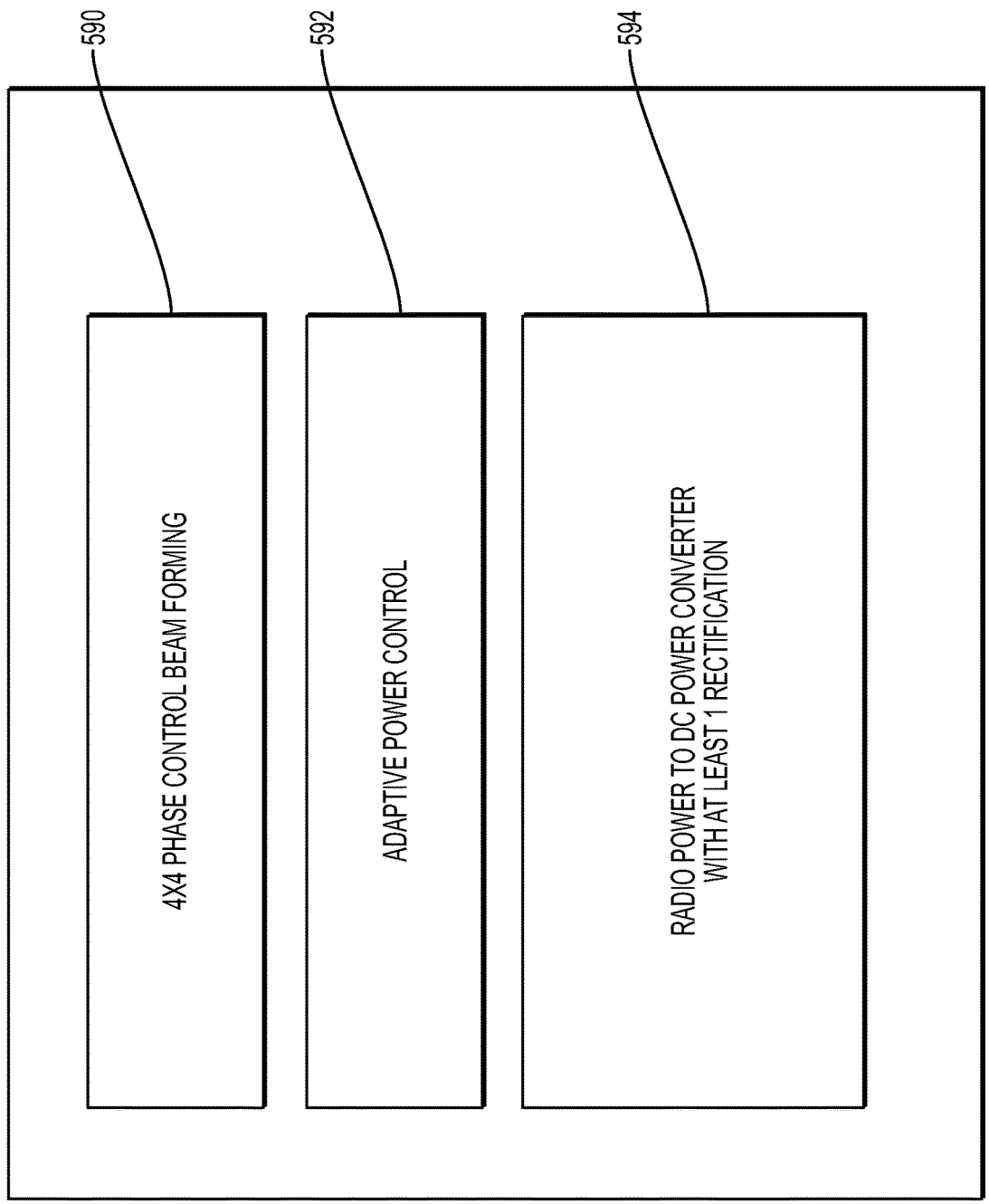
FIG. 26 is a block diagram of circuitry within the devices of FIG. 24 to support energy harvesting in accordance with an example embodiment.

FIG. 26 is a block diagram of circuitry within device 562 and device 564 of FIG. 24 to support energy harvesting in accordance with an example embodiment. In one embodiment, device 562 and device 564 can include beam forming 590 to direct transmission of a radio frequency signal instead. For example, device 562 or network system 560 can beam form a radio frequency signal to device 564 to increase the power of the radio frequency signal that is received by device 564. Device 564 will then harvest energy at a greater rate.

In one embodiment, device 562 and device 564 can include adaptive power control. In the example, where device 564 is requesting coupling to device 564 to receive a radio frequency transmission the adaptive power control can be used to increase the power of transmission. In other words, device 564 can request that the strength of the radio frequency signal be increased to support energy harvesting by device 564.

In one embodiment, device 562 and device 564 will have energy harvesting capability of radio frequency signals. The energy harvesting circuitry will convert one or more radio frequency signals to DC power using a RF to DC power converter. The RF to DC power converter will have at least one rectification.

Figure 27:
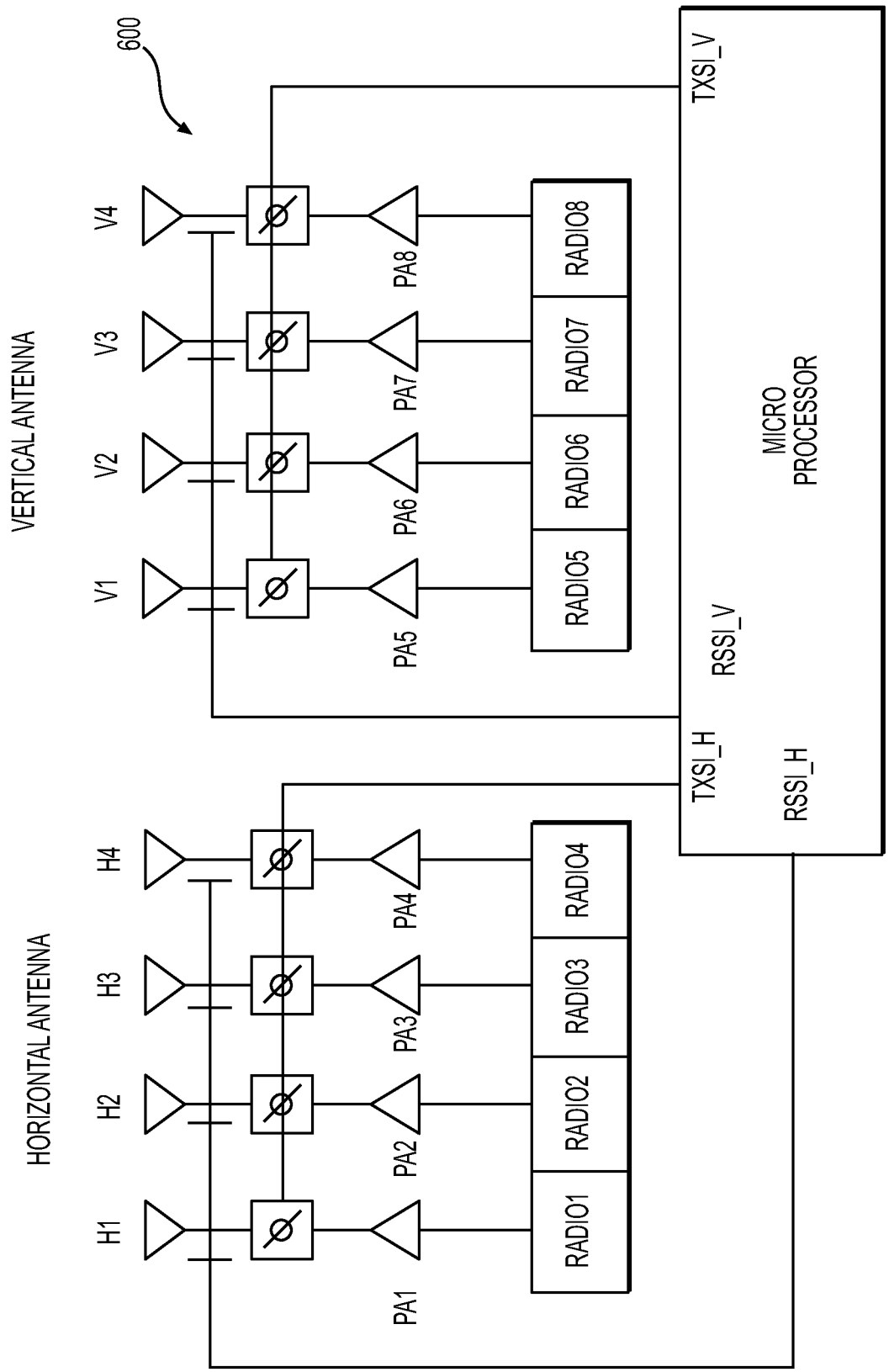
FIG. 27 is a block diagram illustrating a horizontal and vertical antenna array controlled by a microprocessor in accordance with an example embodiment.

FIG. 27 is a block diagram 600 illustrating a horizontal and vertical antenna array controlled by a microprocessor in accordance with an example embodiment. The antenna array can be configured to transmit or receive. Each horizontal antenna has a radio and amplifier for independent control. Similarly, each vertical antenna has a radio and amplifier for independent control. Thus, more than one horizontal or vertical antenna can used simultaneously to increase power output by the antennas.

Components of FIGS. 1-16 will be referred to when discussing the medical system disclosed herein below for monitoring the musculoskeletal system. The description of FIGS. 1-16 are also included in any discussion of structure or operation herein below. The medical system comprises one or more screws (274, 276) coupled to the musculoskeletal system, one or more devices (282, 284), and a computer 278. Computer 278 can be any device configured to receive measurement data from the one or more screws (274, 276) or the one or more devices (282, 284). In one embodiment, a screw 274 is configured to couple a first bone of the musculoskeletal system in a predetermined location. An opening can be drilled in a first bone of the musculoskeletal system and tapped for receiving screw 274. The predetermined location of screw 274 can be registered relative to the bone model of the first bone and stored in computer 278.

Screw 274 comprises electronic circuitry 310, an IMU 330, and a dual band antenna 312. The dual band antenna comprises a first antenna configured to receive or transmit a signal below 1 gigahertz and a second antenna configured to receive or transmit a signal above 1 gigahertz. In one embodiment, the dual band antenna operates at 915 megahertz and 2.4 gigahertz. In one embodiment, screw 274 has a non-electrically conductive body 386 and an electrically conductive cap 384. In one embodiment, body 386 of screw 274 comprises a plastic or polymer material. At least a portion of body 386 has a threaded portion 390 and a tip 394. Threaded portion 390 is configured to hold screw 274 in place and retain screw 274 within the first bone of the musculoskeletal system. Electrically conductive cap 384 couples to body 386 of screw 274 to seal a cavity 388 housing electronic circuitry 310, IMU 330, sensors 332, dual band antenna 312, and other circuitry or components. Electrically conductive cap 384 couples to the ground of electronic circuitry 310. IMU 330 is configured to provide information on position, location, movement, and trajectory corresponding to nine degrees of freedom. In one embodiment, IMU 330 comprises a geomagnetic sensor 324, a gyroscope sensor 326, and an accelerometer sensor 328. Screw 274 further includes a frequency band modulation split circuit 314, a radio frequency to DC radio rectifier circuit 316, energy storage device 318, DC-DC converter 320, sensors 332, and transceiver and control circuit 322. Electronic circuitry 310 is configured to control a measurement process and transmit measurement data. Screw 274 can be in two way communication with one or more devices (282, 284) or one or more computers 278.

Sensors 332 are configured to measure one or more parameters. Sensors can comprise a transducer, a microphone, a temperature sensor, a force sensor, an inertial sensor, a density sensor, an optical sensor, infection detection, blood oxygen level sensor, a position measurement system, a tracking system, a fluid sensor, a magnetic sensor, a mechanical sensor, a pressure sensor, a pH sensor, a photo sensor, a piezo sensor, a capacitive sensor, a strain gauge, a flow sensor, a chemical sensor, an infrared sensor, a flow sensor or a biological sensor. Sensors 332 can also be a device configured to provide therapy, heal, improve health, or support rehabilitation. For example, sensors 332 can emit a continuous frequency or a pulsed signal to support bone healing.

Device 282 is configured to couple to the skin or epidermis in proximity to screw 274. In one embodiment, device 282 is configured as a patch or bandage having an adhesive system 410. Device 282 is flexible to conform and couple to complex shaped surfaces. In one embodiment, package 366 of device 282 comprises silicone to support flexibility. Adhesive system 410 is coupled to a surface of device 282. A cover of adhesive system 410 is removed to expose an adhesive layer prior to coupling device 282 to the skin. The adhesive layer is a medical grade adhesive configured to hold device 282 to the skin. An electronic system is placed within device 282 that is similar to the electronic system placed within screw 274. For brevity, the individual circuits of electronic circuitry 310 will not be disclosed but can be reviewed in FIG. 10. A difference between device 282 and screw 274 is that device 282 further includes a power source. In one embodiment, the power source is battery 360. Battery 360 can be a rechargeable battery. Battery 360 is configured to power electronic circuitry 310 in device 282 but also provide power to screw 274. Device 282 transmits a first signal at a first frequency to screw 274. The first signal is at a frequency of 1 gigahertz or less that penetrates through skin and tissue. In one embodiment, the first signal transmitted by device 282 is at 915 megahertz in the ISM band. Screw 274 receives the first signal transmitted from device 282 and harvests energy from the first signal. In one embodiment, screw 274 does not have any stored energy to operate electronic circuitry 310 therein. Thus, a first step is to begin harvesting energy that is received by the first antenna of screw 274. The first signal is harvested by radio frequency to DC radio rectifier circuit 316 of electronic circuitry 310 in screw 274. The rectified signal is stored on energy storage device 318 in screw 274. The rectified signal typically has a voltage lower than needed by electronic circuitry 310. DC-DC converter couples to energy storage device 318 and generates one or more voltages to power electronic circuitry 310 within screw 274. In one embodiment, electronic circuitry 310 in screw 274 is configured to be enabled when the stored energy in energy storage device 318 in screw 274 is above a predetermined threshold. In one embodiment, energy storage device 318 in screw 274 is a super capacitor. The stored energy above the predetermined threshold is sufficient to power electronic circuitry 310 of screw 274 for a measurement process and transmit the measurement data to device 282, another different device, another different screw, or a computer. Device 282 can continuously send the first signal thereby allowing continuous operation of screw 274 for generating measurement data and transmission of the measurement data. In one embodiment, the first signal transmitted by device 282 to screw 274 supports the generation of a current to charge energy storage device 318 in screw 274 of 10 milliamperes or greater.

Screw 274 and device 282 each have a dual band antenna 312 configured for transmitting or receiving information. Screw or device 274 and device 282 are configured to transmit or receive information at either frequency band that dual band antenna 312 is configured to operate at. In the example, a first antenna of dual band antenna 312 operates at 1 gigahertz or less. A second antenna of dual band antenna 312 operates at 1 gigahertz or more. As disclosed herein operation of the first antenna at 915 megahertz which is within the ISM band while the second antenna is operated at 2.4 gigahertz corresponding to Bluetooth wireless protocol. In one embodiment, the first antenna is a coil antenna 402 as shown in FIG. 14. The second antenna is formed on or couples to printed circuit board 356 and housed within a cavity of screw body 402 with coil antenna 402. In one embodiment, coil antenna couples around module 396. Alternatively, an antenna 500 corresponding to dual band antenna 312 for use on a screw or device as disclosed herein can be formed on a dielectric substrate 506. Antenna 500 has an antenna formed on each side of dielectric substrate 506 thereby forming a dual band antenna. The first antenna 512 is formed having a conductor 508 on a first side 502 of dielectric substrate 506. The second antenna 514 is formed having a conductor 510 on a second side 504 of dielectric substrate 506. In one embodiment, conductor 508 overlies or overlaps conductor 510 less than 50 percent to reduce interference, increase efficiency, and improve a radiation pattern of antenna 500.

In one embodiment, multiple screws, multiple devices, and one or more computers can be in communication with one another as a medical system configured to generate measurement data. The multiple screws will receive power through one or more radio frequency signals where the one or more radio frequency signals are harvested for energy to power the multiple screws. This is depicted in FIG. 9 where computer 278 receives measurement data to display, analyze, or report about the musculoskeletal system using quantitative measurement data or support patient health by providing therapy, promote healing, or rehabilitate. In the example, a device 282 is in communication with screw 274 that is coupled to a femur 270 of a leg. A device 284 is in communication with screw 276 that is coupled to a tibia 272 of the leg. The medical system is configured to provide quantitative measurement data related to a knee joint or provide therapy, promote healing or rehabilitate. Device 284 has electronic circuitry 310 similar to device 282 as disclosed herein above. Similarly, screw 276 has electronic circuitry 310 similar to screw 274 as disclosed herein above. Device 284 has a power source like battery 360 of FIG. 11 to support providing a radio frequency signal to power screw 276. In the example embodiment, devices 282 and 284 respectively couple to the epidermis in proximity to screws 274 and 276 to support efficient radio frequency signal transfer. Devices 282 and 284 can include sensors 332 for generating quantitative measurement data or one or more devices for providing therapy, healing, or rehabilitation. Exact positions of screws 274 and 276 are known respective to femur 270 and tibia 272 whereby movement of the knee joint can be precisely monitored and measured by the IMU 330 in screws 274 and 276. Screws 274 and 276 are zeroed relative to gravity to support measurement with 9 degrees of freedom. In one embodiment, the medical system is configured to measure at least one of a range of motion, rotation, or dynamic stresses related to translation of the musculoskeletal system. In one embodiment, screws 274 and 276 are configured for post-operative monitoring for compliance to a post-operative regimen. In one embodiment, computer 278 is a device or phone that is used in conjunction with the medical system for running software and for transmitting and receiving information from device 282, device 284, screw 274, and screw 276. In one embodiment, the medical system is configured to provide an exercise regimen that can be sent to the device or a phone. Screws 274 and 276 are configured to be activated to monitor the exercise regimen such that the musculoskeletal system remains within a healing zone. In one embodiment, the medical system and computer 278 is configured to review the measurement data from device 282, device 284, screw 274, and screw 27 to evaluate post-operative exercises, post-operative treatment, or pharmaceuticals.

Components of FIGS. 1-27 will be referred to when discussing a wireless system disclosed herein below for performing a task. The description of FIGS. 1-27 are also included in any discussion of structure or operation herein below. The wireless system 450 comprises a device 474 configured to receive one or more radio frequency signals. In one embodiment, device 474 operates at 15 milliamperes or less. In one embodiment, device 474 operates at 10 milliamperes or less. In general, device 474 is configured to harvest energy from any radio frequency signal received by the antenna system of device 474. Energy harvested from one or more radio frequency signals is stored on energy storage device 318. Device 474 includes some or all the electronic circuitry 310 listed in FIG. 10 for energy harvesting one or more radio frequency signals and converting the energy to power electronic circuitry 310 to perform at least one task. In one embodiment, device 474 can operate continuously if the one or more radio frequency signals are continuously provided. Distance and transmit power are important factors for device 474 to be powered continuously with one or more radio frequency signals. Device 474 can be configured to receive and transmit in many different frequency bands and configured for different wireless protocols. Examples of different common wireless protocols are WiFi, Bluetooth, Zigbee, WiMax, ISM, or wireless mesh networks. In general, device 474 has antenna 454. Antenna 454 can be part of an antenna system capable of receiving one or more different frequency bands. For example, the antenna system of disclosed in FIG. 10 is a dual band antenna 312 operating in a first frequency band and a second frequency band. In one embodiment, antenna 454 is an antenna that operates in a frequency band below 1 gigahertz. The second antenna of the dual band antenna 312 of device 474 can be configured for operation in a WiFi frequency band or Bluetooth frequency band. In one embodiment, the WiFi or Bluetooth antenna is housed within the enclosure of device 474. In one other example, dual band antenna 312 can operate to receive and transmit WiFi and Bluetooth radio frequency signals. In one embodiment, device 474 will harvest energy from all signals received on the antenna system. For example, device 474 will harvest WiFi and Bluetooth signals received if device 474 is configured to receive WiFi signals from WiFi router 468, Bluetooth from cell phone 456, or Bluetooth from Bluetooth system 460. In the example, Bluetooth system 460 is a mesh network capable of providing interconnectivity over a wide area.

A second wireless device is configured to couple to device 474. For example, cell phone 456 has a rechargeable battery capable of delivering high current. Router 468 or Bluetooth system 460 is powered by the electric grid and has a transmission range (e.g. signal strength) limited by regulation. Thus, the cell phone 456, router 468, or Bluetooth system 460 can be the second wireless device configured to power device 474 using a radio frequency signal. In general, the second wireless device is configured to transmit one or more radio frequency signals to device 474. In one embodiment, cell phone 456 is configured to transmit a radio frequency signal to device 474. The radio frequency signal is a Bluetooth signal. Alternatively, router 468 is configured to transmit a radio frequency signal to device 474. As an example, the antenna system of device 474 is configured to receive the Bluetooth or WiFi radio frequency signal respectively from cell phone 456 or router 468. In one embodiment, antenna system of device 474 receives a Bluetooth signal from cell phone 456. Device 474 is configured to harvest energy from the Bluetooth signal from cell phone 456. Device 474 will also harvest energy from other Bluetooth signals the antenna system receives. Device 474 is enabled for operation after a predetermined amount of energy is harvested from the Bluetooth signal from cell phone 456. In one embodiment, energy harvested from the Bluetooth signal from cell phone 456 is stored on energy storage device 318 of device 474. Electronic circuitry 310 of device 474 is enabled when a predetermined amount of energy is harvested. In one embodiment, the predetermined amount of energy is sufficient to enable electronic circuitry 310, perform at least one task, transmit information related to the at least task, and finish with an orderly shutdown of electronic circuitry 310. A communication handshake can occur between cell phone 456 and device 474 once electronic circuitry 310 within device 474 is enabled thereby establishing communication. Cell phone 456 can continue being in communication with device 474. Energy is harvested by device 474 as long as cell phone 456 is in communication with device 474 thereby supporting continuous operation of device 474.

In general, device 474 can communicate to the second wireless device that more power is required by device 474 to continue operation. For example, if the distance increases between device 474 and the second wireless device the signal strength may need to be increased to generated sufficient power to maintain operation. Similarly, the signal could be blocked or reflected requiring an increase in signal strength. In one embodiment, the communication between device 474 and the second wireless device can be a feedback path to modulate a transmit power of the second medical device to support continuous operation of device 474. Thus, the transmit power can be increased or decreased depending on amount of energy being harvested and the task being performed by device 474. In one embodiment, harvested energy stored on energy storage device 318 is monitored. Monitoring the harvested energy supports communication on the feedback to modulate the transmit power sent by the second wireless device. In one embodiment, the communication between device 474 and the second wireless device to increase or decrease the transmit power can include using beam forming. Beam forming increases the directivity of the transmit power from the second wireless device. The transmission is more focused at device 474 thereby increasing the transmit power by reducing radiation in other directions.

Although device 474 does not require a power source, it may in some circumstances be beneficial to have a local power source within device 474. For example, device 474 can include a rechargeable battery. In one embodiment, DC-DC Converter 320 of electronic circuitry 310 within device 474 can include the ability to charge the rechargeable battery while electronic circuitry 310 is enabled or when electronic circuitry 310 is not communication within another device. This supports keeping device 474 powered in the event that the signal between device 474 and the second wireless device weakens or is blocked for a short period of time. The battery can sustain activity and keep electronic circuitry 310 with device 474 operating. Energy harvesting by device 474 provides the benefit of eliminating a battery charging station for device 474.

In one embodiment, device 474 has dual band antenna 312. Dual band antenna 312 comprises two or more antennas operating at two or more frequency bands. The two or more frequency bands are non-overlapping. In one embodiment, dual band antenna has a first antenna that operates at frequencies below 1 gigahertz and a second antenna that operates at frequencies above 1 gigahertz. The lower frequency antenna supports better penetration through different materials thereby improving efficiency for radio frequency energy transfer. The second antenna can comprise more than one antenna for the frequency bands above 1 gigahertz and can support Bluetooth, WiFi, or other communication standards for two way communication with device 474. The second wireless device can comprise router 468, cell phone 456, Bluetooth system 460, or a patch device 256 (as shown in FIG. 8) as examples of interconnectivity to device 474. In one embodiment, patch device 256 transmits at the first frequency below 1 gigahertz to device 474. In one embodiment, router 468, cell phone 456, or Bluetooth system 460 can communicate to device 474 through the frequency band above 1 gigahertz. In the example, power transfer to device 474 is performed efficiently by using a lower frequency while communication can occur using a standard protocol. In one embodiment, dual band antenna 312 of device 474 has a first antenna 512 formed on first side of a substrate 506 and a second antenna 514 formed on a second side 504 of substrate 506 thereby reducing a form factor. The first antenna 512 and the second antenna 514 of dual band antenna 312 of device 474 operates at different non-overlapping frequencies. In one embodiment, a conductor 508 of first antenna 512 and a conductor 510 of the second antenna 514 overlaps each other less than 50 percent to improve efficiency.

Device 474 includes a radio frequency to DC radio rectifier circuit 316, energy storage device 318, a DC-DC converter 320, and an IMU 330. DC radio rectifier circuit 316, energy storage device 318, a DC-DC converter 320 are configured to receive, harvest, store, and convert energy from one or more radio frequency signals coupled to device 474 into one or more voltages to power transceiver and control circuit 322 of electronic circuitry 322. In one embodiment, IMU 330 comprises geomagnetic sensor 324, gyroscope sensor 326, and accelerometer sensor 328. IMU 330 is a position and trajectory tracking system having nine degrees of freedom to determine position, location, or trajectory. An example of device 474 that operates with a current of 15 milliamperes is an audio device such as ear phones or ear buds used with cell phone 456. Cell phone 456 can sustain used of device 474 as an audio device through harvesting of the RF signal communicating between cell phone 456 and device 474. In one embodiment, device 474 includes sensors 332 of electronic circuitry 310. Sensor 332 of device 474 is configured to measure one or more parameters. The parameters can then be reported to the second wireless device such as cell phone 456 or other device in communication with device 474. In one embodiment, device 474 can include a rechargeable battery. In one embodiment, harvested energy by device 474 is used to recharge the rechargeable battery in device 474. The second wireless device in communication with device 474 is configured to request modulation of a transmit power of the transmission of the radio frequency signal of the second wireless device to support continuous operation of device 474.

Components of FIGS. 1-27 will be referred to when discussing a medical system disclosed herein below for performing a task. The description of FIGS. 1-27 are also included in any discussion of structure or operation herein below. The medical system includes a first medical device, a second medical device, and a computer. The first medical device and second medical device can be in communication with each other. The first or second medical device can also be in communication with the computer. In one embodiment, the first medical device is configured to be placed below the dermis. In one embodiment, the first medical device does not have a power source. The first medical device harvests energy from one or more radio frequency signals and stores the energy until enough energy is stored to complete a task. The first medical device includes electronic circuitry 310 configured to perform the at least one task. The first medical device can have sensors 332 configured to measure one or more parameters. Sensor 332 can also comprise one or more devices configured to provide therapy, heal, or support rehabilitation. The first medical device also includes IMU 330 that is configured to measure position, location, and trajectory and operates with 9 degrees of freedom. In one embodiment, a module 396 comprises printed circuit board 356 and electronic circuitry 310. The enclosure is sealed with a cap that isolates the electronic circuitry 310 from an external environment. In one embodiment, subcutaneous screw 380 comprises screw body 386 and screw head 384. Screw body 386 is the enclosure and screw head 384 is the cap to seal the enclosure from an external environment. Module 396 is placed within cavity 388 of screw body 388 prior to sealing the cap to the enclosure. At least a portion of screw body 388 has a threaded region 390. In one embodiment, screw body 388 comprises a non-conductive material such as a plastic, polymer, or other biocompatible material. In one embodiment, the cap comprises electrically conductive material. The cap or screw head 384 is configured to couple to ground of electronic circuitry 310 and a terminal of dual band antenna 312. In one embodiment, subcutaneous screw 380 is configured to screw into a bone of the musculoskeletal system where it can be retained permanently or for a predetermined time (and then removed).

The first medical device is configured to be in communication with the second medical device or a computer. For example, subcutaneous screw 264 (first medical device) is configured to communicate with patch device 256 (second medical device) or computer 252 as shown. In one embodiment, the first medical device such as subcutaneous screw 264 includes dual band antenna 312 that couples to electronic circuitry 310. Electronic circuitry 310, IMU, 330, sensors 332, and dual band antenna 312 are configured to fit within the cavity of the first medical device. Electronic circuitry 310 controls IMU 330 and sensors 332 measurement and transmits measurement data to patch device 256 or computer 252. Dual band antenna 312 of the first medical device comprises a first antenna and a second antenna. The first antenna is configured to operate within a first frequency band below 1 gigahertz. The second antenna is configured to operate with a second frequency band above one gigahertz. The first frequency band supports efficient transfer of energy beneath tissue of a body. The second frequency band utilizes many of the common short range communication protocols for transferring information or measurement data such as WiFi, Bluetooth, Zigbee, WiMax, or other communication standards. The first medical device can have more than 2 antennas. Electronic circuitry 310 of the first medical device is configured to harvest energy received by dual band antenna 310 of the first medical device. Energy is harvested until operation of the electronic circuitry 310 can be sustained to perform at least one task. In one embodiment, radio frequency signals coupled to dual band antenna 312 are harvested, rectified, stored, converted to one or more voltages to enable electronic circuitry to control a measurement process, transmit measurement data, and operate an orderly shutdown of electronic circuitry 310.

Electronic circuitry 310 of the first medical device includes energy storage device 318. In one embodiment, energy storage device 318 of the first medical device is a super capacitor that is configured to receive the harvested energy received by dual band antenna 312 of the first medical device. The first medical device includes a position, motion, and trajectory tracking system. In one embodiment, the position, motion, and trajectory system of the first medical device is IMU 330 having 9 degrees of freedom. In one embodiment, electronic circuitry 310 is not enabled until a predetermined energy is stored on energy storage device 318 of the first medical device.

In one embodiment, the first antenna of the first medical device is a coil antenna 402. Coil antenna 402 supports higher efficiency of received signals by the first antenna of dual band antenna 312 of the first medical device. Coil antenna 402 is configured to fit within the cavity of the first medical device. In one embodiment, the second antenna of dual band antenna 312 is formed on printed circuit board 356 of module 396. Module 396 is configured to fit within coil antenna 402. Both coil antenna 402 and module 396 are retained within the cavity.

In one embodiment, first antenna 512 of dual antenna 312 of the first medical device is formed on a first side 502 of a dielectric substrate 506. Second antenna 514 of dual antenna 312 of the first medical device is formed on a second side 504 of the dielectric substrate 506. The conductor 508 of the first antenna of dual antenna 312 of the overlies the conductor 510 of the second antenna of dual antenna 312 of the first medical device by 50 percent or less. Reducing overlap of conductors 508 and 510 increases the efficiency of dual antenna 312 at the first and second operating frequency bands. In one embodiment, the cap comprises an electrically conductive material. An electrode of first antenna 512 of the first medical device is configured to couple to the electrically conductive material of the cap. Similarly, an electrode of the second antenna 514 of the first medical device is configured to couple to the electrically conductive material of the cap.

In the example, of the first medical device the enclosure is a screw body 386 and the cap is a screw head 384 forming subcutaneous screw 380. Screw body 386 has a cavity 388 that can receive module 396 and dual band antenna 312. Screw head 384 coupled to screw body 386 forms a hermetic seal of cavity 388. In one embodiment, the first medical device is a passive device that does not have a power source. Operation is enabled by harvesting energy from a radio frequency signal. The example of the first medical device shows that the enclosure and the cap of first medical device can take many different forms and shapes depending on the application and where it is placed below the dermis. Subcutaneous screw 380 as the first medical device is configured to couple to the musculoskeletal system and more specifically can be screwed into a bone of the musculoskeletal system for performing a task such as position tracking, measurement of one or more parameters, providing a therapy, or supporting rehabilitation. In one embodiment, screw body 386 can have one or more openings or one or more sealed opening. The one or more openings can provide access for a sensor or device within the first medical device to measure an external environment, provide therapy, or rehabilitate. The sealed openings can provide a path for one or more signals. For example, the one or more openings of screw body 386 can be sealed with a material that is transmissive to different frequency light. The light can be used for measurement, therapy, or rehabilitation.

In one embodiment, a washer 164 is configured to couple to a screw. Washer 164 can include electronic circuitry 310 and dual band antenna 312 of FIG. 10. Washer 164 is configured to harvest energy of one or more radio frequency signals received by dual band antenna 312 in washer 164 as disclosed herein above for electronic circuitry 310. The harvested energy of washer 164 enables operation of electronic circuitry 310 within washer 164 to perform at least one task such as performing a measurement, providing therapy, or supporting rehabilitation. Washer 164 couples to a head of the screw and distributes a force from the screw head to an area of a surface of washer 164 thereby reducing the force per unit area. In one embodiment, washer 164 can couple to subcutaneous screw 380.

In one embodiment, a plate 190 is configured to couple to one or more screws or one or more washers. Plate 190 can include electronic circuitry 310 and dual band antenna 312 of FIG. 10. Plate 190 is configured to harvest energy of one or more radio frequency signals received by dual band antenna 312 in plate 190 as disclosed herein above for electronic circuitry 310. The harvested energy of plate 190 enables operation of electronic circuitry 310 within plate 190 to perform at least one task such as performing a measurement, providing therapy, or supporting rehabilitation. Plate 190 couples to a head of the screw or a washer and distributes a force from the screw head or washer to an area of a surface of plate 190 thereby reducing the force per unit area. In one embodiment, plate 190 can couple to subcutaneous screw 380 or washer 164.

The second medical device of the medical system comprises a flexible enclosure, electronic circuitry 310, a power source coupled to the electronic circuitry, and a dual band antenna. In one embodiment, the second medical device is patch device 256 as shown in FIG. 8. Patch device 256 is a device 350 as shown in more detail in FIG. 11 as device 350. In the example, patch device 256 or device 350 will be referred to interchangeably as the second medical device of the medical system. In one embodiment, patch device 256 is over-molded with a flexible material such as silicone to form a flexible enclosure around the power source, module 396, and dual antenna 312. Device 350 comprises module 396, battery 360, and printed circuit board 358. Module 396 comprises printed circuit board 356 and electronic circuitry 310. In one embodiment, battery 360 is a rechargeable battery. Battery 360 couples to module 396 through interconnect on stripe 368 of flexible printed circuit board 358 of the second medical device. Dual band antenna 312 of the second medical device comprises a first antenna 358 formed on flexible printed circuit board 358 and a second antenna 364 is formed on printed circuit board 356 of module 396. The large circumference of flexible printed circuit board 358 supports a larger antenna to be formed for receiving signals below 1 gigahertz. In one embodiment, patch device 256 has an adhesive system that couples patch device 256 to the skin in proximity to the first medical device to support efficient energy transfer. Note that the second medical device has similar electronic circuitry and dual antenna system as the first medical device. A main difference between the first and second medical devices is that the second medical device has battery 360 and the first medical device does not have a battery or power source. Energy has to be harvested by the first medical device in order for it to operate. The medical system is configured to have the second medical device transmit a radio frequency signal in a first frequency band to the first medical device. In the example, the first antenna 358 of the second medical device is configured to transmit a signal to the first medical device. As mentioned the signal will be within a first frequency band less than 1 gigahertz. The first frequency band supports the signal penetrating through tissue to the first medical device. In one embodiment, the second medical device is configured to transmit the signal continuously thereby powering the first medical device continuously. The first medical device such as subcutaneous screw 262 is configured to be in communication with the first medical device such as patch device 256 after the subcutaneous screw 262 has harvested enough energy to enable electronic circuitry 310 within subcutaneous screw 262. In one embodiment, the communication can occur at a second frequency band that supports the transmission of data or information such as Bluetooth, WiFi, Zigbee, WiMax, or other standard protocols. The second frequency band corresponds to the second antenna 364 of device 350. Subcutaneous screw 364 also has an antenna formed on printed circuit board 356 of module 396 within the first medical device for communicating with the second medical device. The first and second medical devices can be in communication with each other or other devices. For example, the first and second medical devices can be in communication with computer 252. The first and second medical devices can also be in communication with other similar devices if implanted or place in proximity to the first and second medical devices.

Components of FIGS. 1-27 will be referred to when discussing a medical system disclosed herein below for performing a task. The description of FIGS. 1-27 are also included in any discussion of structure or operation herein below. A medical system comprises a patch device 256, a computer 252, and a device. The patch device 256 of FIG. 8 is shown as device 350 in FIG. 11. Patch device 256 or device 350 will be used interchangeable in disclosing operation or components therein. In one embodiment, patch device 256 comprises a module 396, a battery 360, an antenna system, and a printed circuit board 358. In one embodiment, patch device 256 is configured to be similar to a bandage that can be coupled to the skin to take measurement, provide a therapeutic benefit, or be in communication with the device. Module 396 comprises a printed circuit board 356 and electronic circuitry 310. Electronic circuitry 310 is disclosed in FIG. 310. Electronic circuitry 310 includes an IMU 330 and sensors 332. Sensors 332 can be configured to measure one or more parameters. Sensors 332 can also comprise one or more devices for providing a therapy, support healing, or rehabilitate. IMU 33 is coupled to the electronic circuitry and is configured to measure position, movement, and trajectory of patch device 256. In one embodiment, the antenna system is configured to harvest energy from one or more radio frequency signals received by the antenna system. In one embodiment, electronic circuitry 310 is configured to recharge battery 360 with the harvested energy from the one or more radio frequency signals. For example, a radio frequency signal from computer 252 to patch device 256 can be harvested. The radio frequency signal is also a communication path for information between computer 252 and patch device 256. Package 366 of patch device 256 comprises a flexible enclosure. The flexible enclosure of package 366 is configured to couple to a non-planar surface. In one embodiment, patch device 256 comprises an area 50 millimeters by 25 millimeters or less. In one embodiment, package 366 is configured to couple to skin similar to a bandage. In one embodiment package 366 is less than 4 millimeters thick. In one embodiment, battery 360 is a flexible battery configured to conform to a shape of a surface to which the patch device couples.

Electronic circuitry 310 further comprises radio frequency to DC radio rectifier circuit 316, energy storage device 318, and DC-DC converter 320. Radio frequency to DC radio rectifier circuit 316, energy storage device 318, and DC-DC converter 320 support harvesting the energy from the one or more radio frequency signals, storing the energy, and providing one or more voltages for enabling electronic circuitry 310. Patch device 256 includes transceiver and control circuit 322. The transceiver can couple to other devices having electronic circuitry 310 or a computer such as computer 252. Control circuitry within transceiver and control circuit 322 controls a measurement process or manages a therapy. Transceiver and control circuit 322 is configured to communicate to other devices or computer 252 to provide measurement data, information related to therapy, or motion information. In one embodiment, the antenna system of patch device 256 comprises a dual band antenna 312. Antenna 362 is formed on printed circuit board 358 where at least a portion of a conductor of antenna 362 has a serpentine shape. In one embodiment, antenna 362 of patch device 256 is formed around a periphery of printed circuit board 368. Printed circuit board 368 is flexible and conforms to non-planar surfaces. Antenna 362 is configured to operate in a first frequency band that is less than 1 gigahertz in frequency. Antenna 364 of dual band antenna 312 is formed on printed circuit 356 of module 396 in patch device 256. Antenna 364 fits in less area than antenna 362 and is configured to operate in a frequency band greater than 1 gigahertz. In one embodiment, the frequency band of antenna 362 does not overlap the frequency band of antenna 364. In one embodiment, a majority of electronic circuitry 310 is coupled to printed circuit board 356. In one embodiment, all of electronic circuitry 310 is coupled to printed circuit board 356 of module 396. Printed circuit board 356 comprises less area than printed circuit board 358. This supports migrating module 396 for different device applications, lower manufacture costs, increase volume, simplify assembly and packaging. Electronic circuitry 310 is configured to perform the at least one task and transmit information related to the at least one task. In one embodiment, battery 360 and module 396 of patch device 256 is placed on printed circuit board 358 along a long axis. Battery 360 and module 360 would be placed centrally along the 50 millimeter length long axis of patch device 256. In one embodiment, a stripe 368 of printed circuit board 358 is formed on the long axis of patch device 256. Battery 360, module 396, and antenna 362 couple to interconnect on stripe 368 to form patch device 256. Package 366 forms the enclosure around printed circuit board 358, battery 360, and module 396 of patch device 256. In one embodiment, package 366 comprises silicone and is molded to seal printed circuit board 358, battery 360, and module 396 from an external environment.

Patch device 256 is configured to couple to a non-planar surface. In the example, patch device 256 is configured to couple to skin in proximity to a second device. In one embodiment, patch device 256 includes an adhesive system. The adhesive system 410 couples to patch device 256. Adhesive system 410 includes a cover that is removed to expose an underlying adhesive layer to couple patch device 256 to a surface. Patch device 256 is configured to transmit a radio frequency signal to a screw 264 or computer 252. In the example, screw 264 is a device having electronic circuitry 310 and the antenna system but no power source. The radio frequency signal transmitted by patch device 256 is harvested by screw 264. After a predetermined amount of energy is stored within screw 264, electronic circuitry 310 of screw 264 is enabled to perform at least one task such as taking a measurement with one or more sensors or provide a therapy support healing or rehabilitation by a device therein. In one embodiment, screw 264 can be operated continuously with an uninterrupted radio frequency signal from patch device 256. In one embodiment, screw 264 in communication with patch device 256 can request a change in transmit power of the radio frequency signal from patch device 256. Screw 264 can request an increase or decrease in transmit power to modulate the transmit power to adjust the energy harvested by screw 264 thereby keeping screw adequately powered to perform one or more tasks. In one embodiment, medical patch 256 includes a dual band antenna 312 comprising a first antenna 512 formed on a first side 502 of a dielectric substrate 506 and a second antenna 514 formed on a second side 504 of dielectric substrate 506. A conductor 508 of the first antenna 512 overlies a conductor 510 of the second antenna 514 by less than 50 percent.

In one embodiment patch device 256 is in communication with computer 252. A WiFi router 468 or Bluetooth network 460 can support communication between patch device 256 and computer 252. At least one radio frequency signal is harvested by patch device 256 to recharge battery 360 within patch device 256. Patch device 256 can be used to monitor a wound and support healing of the wound. Patch device 256 can come in different sizes to cover a wound. In general, the adhesive system 410 of patch device 256 couples to a wound area. In one embodiment, the adhesive system 410 overlies the wound and seals patch device 256 to the wound area thereby isolating the wound area from an external environment. Sensors 332 of patch device 256 includes at least one camera. At least one task of patch device 256 is to continuously, periodically, or randomly monitor the wound. Pictures or video from patch device 256 can be transmitted to computer 252 continuously, periodically, or randomly. Computer 252 can include software to analyze photo or video information on the wound. In one embodiment, computer 252 can send out an alert to indicate a positive or negative change in wound status to the patient or medical staff. Computer 252 can also send wound information to the medical staff for their interpretation and feedback on care for the wound. Sensors 332 of patch device 256 can include at least one of a temperature sensor, a pH sensor, a humidity sensor, a pressure sensor, a MEMs sensor, a chemical sensor, photo diode, ultra violet diodes, light emitting diodes, photo detectors, a transducer or a biosensor to support monitoring the wound or providing treatment to the wound. For example, certain types of light or a signal of a predetermined frequency or amplitude can provide therapy to the wound.

In one embodiment, a plurality of patch devices 256 can be used to perform wireless electrocardiography. Sensors 332 of each patch device 256 includes one or more electrocardiogram electrodes configured to detect electrical activity generated by heart muscle depolarizations. The heart muscle depolarizations generate pulsating electrical waves that are received by the electro-cardiogram electrodes. The electrocardiogram electrode or electrodes of patch device 256 are exposed for coupling to the skin. Adhesive system 410 holds the electro-cardiogram electrode or electrodes to the skin for detecting the electrical activity. In one embodiment, at least four patch devices 256 are used for an electrocardiogram. The four patch devices 256 are configured to be placed a predetermined locations to the skin of the patient. Each patch device 256 has the same circuitry and electro-cardiogram electrodes. In one embodiment, computer 252 has multiple channels for communication. Each patch device 256 is configured to couple to a different communication channel. For example, each channel can be configured for Bluetooth device pairing such that each patch device 256 is paired to a channel of computer 252. Computer 252 receives the information from each patch device and can display the electrocardiographic data. Computer 252 can further analyze the measurement data and indicate points of interest or concern.

Patch device 256 can be configured for photoplethysmography. Patch device 256 is a wireless system for detecting blood volume changes in tissue. Patch device 256 can be used to detect a signal through tissue or a signal reflected back after going through tissue. For example, patch device 256 can be wrapped around a finger where a light source sensor is on one side of the finger and a light detector is on an opposing side of the finger. Patch device 256 is flexible and adhesive system 410 will couple patch device to the skin as it is wrapped around the finger. Alternatively, patch device 256 can have the light source sensor and the photo diode placed to detect reflected signals such that patch device 256 does not require wrapping around the finger. As mentioned sensors 332 includes a light source and a photo detector. The light source is configured to transmit a light signal into tissue. The photo detector is positioned to receive light transmitted through the tissue or reflected off the tissue. The measurement data from the photo detector is transmitted to computer 252. Computer 252 is configured to use the photo detector measurement data to measure heart rate, inter-beat interval, or heart-rate variability, as well as other heart measurements.

Components of FIGS. 1-27 will be referred to when discussing a medical system disclosed herein below for performing a task. The description of FIGS. 1-27 are also included in any discussion of structure or operation herein below. An orthopedic system for pre-operative, intra-operative and post-operative measurement is disclosed herein. The orthopedic system comprises a screw 274, a screw 276, and a computer 278. In one embodiment, screw 274 and the screw 276 do not have an internal power source. The screw 274 is configured to couple to a first bone of a musculoskeletal system and the screw 276 is configured to couple to a second bone of the musculoskeletal system. In the example, screw 274 is coupled to a femur 270 and screw 276 is coupled to a tibia 272. Openings are drilled in the femur 270 and tibia 272 to respectively receive screws 274 and 276. In one embodiment, screws 274 and 276 are configured to monitor a knee joint of a leg. Although the knee joint is used as an example screws 274 and 276 can be mounted in two different bones to monitor movement of a joint of the musculoskeletal system or two bones relative to one another. Thus, screws 274 can be used to monitor a knee joint, hip joint, shoulder joint, spine, ankle, wrist, fingers, or toes as an example. The position and location of screws 274 and 276 are precisely known relative to bone landmarks or location of the specific femur and tibia to which they are attached. The position and location of screws 274 and 276 can be identified precisely using pictures or scans of the musculoskeletal system. The position and location information is provided to computer 278. Computer 278 includes one or more software programs that use measurement data from screws 274 and 276 to assess a joint of the musculoskeletal system, support surgical repair, or support installation of one or more prosthetic components. Screw 274 is configured to harvest radio frequency energy to enable electronic circuitry 310 within screw 274 to perform at least one task. Electronic circuitry 310 within screw 274 includes one or more sensors 332 and an IMU 330 to provide position, movement, and trajectory information. Sensors 332 can include devices for providing a therapy, support healing, or rehabilitation. Examples of devices within sensors 332 are pain mitigation, bone density support, infection support, bone fracture repair, and other therapies that can be provided locally by screws 274 and 276. Similarly, second screw 276 is configured to harvest radio frequency energy to enable electronic circuitry 310 within screw 276 to perform at least one task. Electronic circuitry 310 within screw 276 includes sensors 332 and IMU 330 similar to that disclosed for screw 274. Computer 278 is configured to receive measurement data from screws 274 and 276. IMU 330 in screws 274 and 276 are configured to monitor movement of the first bone relative to the second bone which is included in the measurement data sent to computer 278. The one or more tasks performed by screws 274 and 276 can comprise generating measurement data or performing a therapy as disclosed herein above. The one or more tasks performed by screws 274 and 276 and the measurement data from screws 274 and 276 are used by computer 278. Computer 278 includes one or more software programs that can use the measurement data from screws 274 and 276 to provide information related to alignment, range of motion, loading, impingement, contact points, movement, translation, kinetic assessment, balance, stability, rotation, graft adherence, graft failure, exercises assessment, muscle strength, gait analysis, proprioception, or functional healing to name but a few that the orthopedic system can support analysis of. Computer 278 and display 280 can be configured to provide the information in a manner that supports rapid assimilation of measurement data through graphics, audible, or haptic means.

IMU 330 of screw 274 and IMU 330 of screw 276 are zeroed relative to gravity to support accurate position, movement, and trajectory measurement. IMU 330 of screw 274 and IMU 330 of screw 276 are zeroed relative to each other. Computer 278 has a position or location of the screw 274 relative to femur 270. Similarly, computer 278 has a position or location of screw 276 relative to tibia 272. Measurement data from IMU 330 of screw 274 and measurement data from IMU 330 of screw 276 is provided to computer 278 once screws 274 and 276 are enabled. In one embodiment, computer 278 can include multiple channels for connecting to screws 274 and 276 such that both can be providing information simultaneously in real-time. Computer 278 is configured to calculate a position of femur 270 relative to tibia 272 in real-time from measurement data respectively from screw 274 and screw 276.

In one embodiment, a device 282 and a device 284 are respectively placed in proximity to screw 274 and screw 276. For example, devices 282 and 284 can be coupled to the skin of the leg with an adhesive. Alternatively, devices 282 and 284 can be in a brace or sleeve that when worn around the knee joint will locate devices 282 and 284 in proximity to screws 274 and 276. Device 282 and device 284 each include a power source. In one embodiment, device 282 and device 284 each have a rechargeable battery 360. In one embodiment, device 282 and device 284 transmit a radio frequency signal in a band below 1 gigahertz respectively to screw 274 and screw 276. Screws 274 and 276 respectively harvest energy from the radio frequency signal in a frequency band below 1 gigahertz from device 282 and device 284. After a predetermined amount of energy is stored by energy storage device 318 in screw 274, screw 274 is enabled to perform at least one task. Similarly, screw 276 is enabled to perform at least one task after a predetermined amount of energy is stored by energy storage device 318 in screw 276. Computer 278 is configured to report position, motion, or rotation of femur 270 or tibia 272 using measurement data from screw 274 or screw 276. Computer 278 can also process movement of femur 270 and tibia 272 relative to one another. Movement or location information can be reported on display 280 of computer 278 in a surgical environment or post-operatively. Computer 278 is configured to assess aspects of a knee joint of a leg such as alignment, range of motion, extension, and flexion. Computer 278 records movement of femur 270 and tibia 272 as the leg is moved through one or more different motions using measurement data from screw 274 and screw 276.

In one embodiment, an anterior-posterior drawer is performed on the knee joint. Computer 278 is configured to measure translation and displacement relative to screws 274 and 276 from the measurement data from screws 274 and 276. In general, the measurement is used to determine if there is excessive posterior translation in the knee joint. The amount of posterior translation can be disclosed or indicated on display 280 of computer 278. In one embodiment, a Lachman Test is performed on the knee joint. Computer 278 is configured to assess the anterior motion of the tibia to define ACL stability from the measurement data received from screws 274 and 276. The assessment can be disclosed on display 280 of computer 278. In one embodiment, medial-lateral forces can be applied to the knee joint at 20 degrees. The forces can be applied by a device that measures the applied forces. In one embodiment, computer 278 receives an approximate applied force. The computer is configured to assess the collateral ligament stability from measurement data from screw 274 and screw 276. The assessment of collateral ligament stability can be displayed on display 280 of computer 278.

Computer 278 can be configured for post-operative monitoring of the knee joint using measurement data from screw 274 and screw 276. In one embodiment, a post-operative exercise regimen is prescribed to a patient. Screw 274 and screw 276 can be enabled during an exercise session. The patient post-operative exercise regimen is compared to monitored movement of the knee joint by measurement data from screw 274 and screw 276. Screw 274 and 276 provides the measurement data to computer 278. Computer 278 receives and uses the measurement data to provide an assessment, rehabilitation report or workflow for improvement. The leg can be placed in a defined extension maneuver with an applied resistance. A device can be used to measure and apply the resistance. The applied resistance is provided to computer 278. Computer 278 is configured to measure quadriceps strength and torque using measurement data from screws 274 and 276 knowing the extension maneuver and the applied resistance. Computer 278 can display the quadriceps strength and torque on display 280. Screws 274 and 276 can be enabled to monitor the leg in motion under normal walking or running conditions. Movement of the leg is monitored using measurement data from screw 274 and 276. Computer 278 receives the measurement data and assesses gait mechanics such as stride, cadence, activity, steps, and other movement. Computer 278 can report on the gait mechanics. Computer 278 can also provide an improvement plan based on the measurement data from screws 274 and 276. Furthermore, a knee exam can be performed with measurement data from screw 274 and screw 276 in real-time for activities such as walking, running, acceleration, or deceleration. The computer is configured to assess final healing of the knee joint from the measurement data doing the above mentioned activities. The computer can also provide a plan or work flow for continued improvement or determine areas of concern if the knee joint has not healed based on the assessment.

Components of FIGS. 1-27 will be referred to when discussing a medical system disclosed herein below for performing a task. In one embodiment, the medical system is an orthopedic medical system. The description of FIGS. 1-27 are also included in any discussion of structure or operation herein below. An orthopedic system for pre-operative, intra-operative, and post-operative measurement comprises a computer 278, a device 282, a device 284, a screw 274, and screw 276. Device 282, device 284, screw 274, and screw 276 each have electronic circuitry 310. In one embodiment, device 282, device 284, screw 274, and screw 276 each have an IMU 330 for position and motion tracking. Device 282, device 284, screw 274, and screw 276 may not have the same sensors 332, each can have it's own complement of unique sensors for measuring one or more parameters. Sensors 332 can also include devices configured for providing a therapy, healing, pain mitigation, or to support rehabilitation. Device 282 and device 284 include a power source such as a battery. Screw 274 and screw 276 are passive devices requiring energy to be provided before being enabled to perform at least one task. In one embodiment, device 282, device 284, or both can be used with computer 278 to perform a task related to the musculoskeletal system. In one embodiment, computer 278, device 282, device 284, screw 274, and screw 276 are configured to perform a task related to the musculoskeletal system.

Device 282 is configured to couple to a first bone of a musculoskeletal system. Device 282 has an antenna system configured for transmitting and receiving information or measurement data. Device 282 is configured to harvest energy from at least one radio frequency signal received by the antenna system of device 282. In one embodiment, the antenna system is a dual band antenna 312. Device 282 includes an IMU 330 configured to measure movement or location of device 282.

Device 284 is configured to couple to a second bone of a musculoskeletal system. Device 284 has an antenna system configured for transmitting and receiving information or measurement data. Device 284 is configured to harvest energy from at least one radio frequency signal received by the antenna system of device 284. In one embodiment, the antenna system of device 284 is a dual band antenna 312. Device 284 includes an IMU 330 configured to measure movement or location of device 282. Computer 278 is configured to receive measurement data from device 282 or device 284. Devices 282 and 284 are configured to monitor movement of the first bone, the second bone, or the first bone in relation to the second bone. Device 282 and device 284 can have an adhesive system configured to couple device 282 or device 284 to a surface or skin. In one embodiment, device 282 and device 284 are flexible to couple to a non-planar surface or a contour. Alternatively, device 282 and device 284 can part of a brace, wrap, or sleeve to be used with the musculoskeletal system. The brace, wrap, or sleeve couples to the musculoskeletal system placing device 282 and device 284 on or near the skin. In one embodiment, the brace or wrap places devices 282 and 284 at predetermined locations that can respectively be related to the first bone and the second bone.

In one embodiment, IMU 330 of device 282 and IMU 330 of device 284 are zeroed relative to gravity. In one embodiment, IMU 330 of device 282 and IMU 330 of device 284 are also zeroed relative to each other. Measurement data from IMU 330 of device 282 and measurement data from IMU 330 of device 284 is transmitted to computer 278. Computer 278 is configured to use the measurement data to track the positions of devices 282 and 284 and display movement or location on display 280. In one embodiment, computer 278 has a position of device 282 relative to the first bone. Similarly, computer 278 has a position of device 284 relative to the second bone. In one embodiment, computer 278 can translate the positions of devices 282 and 284 relative to the first bone and the second bone to track movement of the first bone and the second bone. Computer 278 is configured to calculate a position of the first bone relative to the second bone in real-time using measurement data from devices 282 and 284.

In one embodiment, computer 278 is configured to report position, motion, or rotation of the first bone or the second bone using measurement data from the first device or the second device. The position, motion, or rotation of the first bone or the second bone is configured to be displayed on display 280. In one embodiment, the orthopedic system is used pre-operatively to generate pre-operative measurement data using device 282 and device 284. The pre-operative measurement data is relate to the first bone and the second bone. In one embodiment, computer 278 is configured to use data analytics and the pre-operative measurement data to support a surgical solution. I In one embodiment, the orthopedic system is used post-operatively to generate post-operative measurement data during a rehabilitation process. The rehabilitation process comprises one or more exercises. Devices 282 and 284 generate the post-operative data as a patient performs the one or more exercises and provides the post-operative measurement data to computer 278. The post-operative measurement data is configured to be displayed on display 280 to indicate progress in rehabilitation. Computer 278 can adjust a regimen for rehabilitation based on the post-operative measurement data. In general, the post-operative measurement data from device 282 and device 284 is configured to be used by computer 278 in an assessment to determine resumption of normal activities. Computer 278 can include a program that uses the post-operative measurement data to support the determination whether the patient is healed.

In one embodiment, the first bone is a femur 270 and the second bone is a tibia 272. Although the example relates to a knee joint and an installation of a prosthetic knee, the concept can be used anywhere on the musculoskeletal system and more specifically on joints of the musculoskeletal system where one bone moves in relation to a second bone. The orthopedic system can be used on joints of the musculoskeletal system such as the spine, hip, shoulder, ankle, elbow, hand, foot, ankle, or wrist. Computer 278 is configured to assess the knee joint of the leg using measurement data from devices 282 and 284. Computer 278 uses the measurement data from devices 282 and 284 to record a range of motion, full extension, flexion, and rotation of the knee joint as the leg is moved through one or more different motions. Other parameters as disclosed herein above can be measured using sensors 332 on device 282 or device 284 and reported to computer 278 or used in a calculation of an assessment.

In one embodiment, an anterior-posterior drawer is performed on the knee joint. Computer 278 is configured to measure a translation and displacement relative to device 282 and device 284 from the measurement data. The translation and displacement of devices 282 and 284 respectively can be converted to movement of femur 270 or tibia 272. The results of the anterior-posterior drawer can be displayed on display 280. In one embodiment, a Lachman Test is performed on the knee joint. Computer 278 is configured to assess the anterior motion of the tibia to define an ACL stability from the measurement data from the devices 282 and 284. As mentioned previously, movement devices 282 and 284 respectively can be converted to movement of femur 270 or tibia 272. The stability of the ACL can be calculated and displayed on display 280. In one embodiment, computer 278 is configured for pre-operative monitoring of the knee joint. Computer 278 uses measurement data from devices 282 and 284 to measure gait mechanics. The gait mechanics from the measurement data is used by computer 278 to support a rehabilitation program or a surgical solution. For example, the gait mechanics can indicate that improvement of the leg function could be achieved through exercise, an external brace, or strengthening specific muscles without the need for surgery. Computer 278 can suggest a work flow or exercise program to improve specific elements of the gait mechanics and rehabilitate the knee. Conversely, the gait mechanics analyzed by computer 278 can indicate that a surgical solution is required as the knee joint or parts of the knee joint may be degraded to a point where replacement is required. Computer 278 can analyze a surgical solution based on the gait mechanics and suggest specific bone cuts, prosthetic components, or installation strategies that will improve the gait mechanics after a prosthetic knee is installed.

Computer 278 can be configured for post-operative monitoring of the knee joint using measurement data from devices 282 and 284. In general, computer 278 can take many different forms. Computer 278 can be a desktop computer, a handheld device, a tablet, a cell phone, or any device having one of digital circuitry, control logic, microcontroller, a processor, or a digital signal processor. Devices 282 and 284 can be incorporated in a brace, wrap, or sleeve that is configured to couple to the leg placing devices 282 and 284 at predetermined locations. Devices 282 and devices 284 can include sensors 332 configured to monitor a surgical wound, detect infection, support pain mitigation, or promote bone healing. In one embodiment, a post-operative exercise regimen is prescribed. Computer 278 has the post-operative exercise regimen that can be provided to a patient. Measurement data from devices 282 and 284 received by computer 278 can be related to specific exercises. In one embodiment, an application using measurement data from devices 282 and 284 is configured to monitor progress of the post-operative exercise regimen. Computer 278 is configured to provide feedback on progress based on the measurement data to the patient or medical staff. In one embodiment, the leg is configured to be placed in a defined extension maneuver with an applied resistance. The amount of applied resistance can be measured and provided to computer 278. Computer 278 is configured to receive measurement data related to the extension maneuver and configured to calculate one or more muscle strength measurements. In one embodiment, computer 278 is configured to measure quadriceps strength and torque using measurement data from devices 282 and 284. In one embodiment, computer 278 is configured to monitor movement of the leg using devices 282 and 284. Computer 278 can assess gait mechanics such as stride, cadence, activity, steps, and other movement using the measurement data. Computer 278 is configured to provide feedback or an improvement plan based on the measurement data. In one embodiment, a knee exam is performed on the knee joint. Devices 282 and 284 are configured to provide the measurement data to computer 278 related to one or more predetermined leg tests. The measurement data measures at least one of range of motion, balance, stability, rotation, graft adherence, proprioception, gait mechanics, or muscle strength that is used to determine if the knee joint is healed. Computer 278 is configured to assess if the knee joint is healed from the measurement data related to the one or more predetermined leg tests. Computer 278 can provide the assessment to a doctor or medical staff for further review.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims. While the subject matter of the invention is described with specific examples of embodiments, the foregoing drawings and descriptions thereof depict only typical embodiments of the subject matter and are not therefore to be considered to be limiting of its scope, it is evident that many alternatives and variations will be apparent to those skilled in the art. Thus, the description of the invention is merely descriptive in nature and, thus, variations that do not depart from the gist of the invention are intended to be within the scope of the embodiments of the present invention. Such variations are not to be regarded as a departure from the spirit and scope of the present invention.

While the present invention has been described with reference to embodiments, it is to be understood that the invention is not limited to the disclosed embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of an invention. Furthermore, while some embodiments described herein include some but not other features included in other embodiments, combinations of features of different embodiments are meant to be within the scope of the invention, and form different embodiments, as would be understood by those skilled in the art.

What is claimed is:

1. A wireless system comprising:
a first wireless device including an antenna system; and
a second wireless device having a power source,
   wherein the second wireless device is configured to transmit one or more radio frequency signals to the first wireless device, wherein the antenna system of the first wireless device is configured to receive the one or more radio frequency signals from the second wireless device, wherein the first wireless device is configured to harvest energy from the one or more radio frequency signals, wherein a communication handshake between the first wireless device and the second wireless device indicates that a communication link has been established, and wherein the first wireless device is configured to perform at least one task using the harvested energy.

2. The wireless system of claim 1, wherein the first wireless device is configured to communicate with the second wireless device to modulate a transmit power of a second medical device to support continuous operation of the first wireless device.

3. The wireless system of claim 2, wherein an energy storage device of the first wireless device stores the harvested energy of the one or more radio frequency signals, wherein the energy stored on the energy storage device is monitored to support modulation of the transmit power of the second wireless device, and wherein the first wireless device is enabled for operation once energy has been harvested from the one or more radio frequency signals.

4. The wireless system of claim 3, wherein beam forming is used to increase transmit power from the second wireless device.

5. The wireless system of claim 1, wherein the first wireless device is configured to charge a battery with the harvested energy from the one or more radio frequency signals.

6. The wireless system of claim 1, wherein the antenna system of the first wireless device comprises two or more antennas operating at two or more frequency bands, and wherein the two or more frequency bands are non-overlapping.

7. The wireless system of claim 6, wherein the second wireless device transmits at a first frequency band to provide energy to the first wireless device, and wherein the second wireless device communicates to the first wireless device through a second frequency band.

8. The wireless system of claim 7, wherein the two or more antennas include a first antenna and a second antenna, wherein a first conductor of the first antenna and a second conductor of the second antenna overlap less than 50 percent.

9. The wireless system of claim 1, wherein the first wireless device is configured to harvest energy from any signal received by the antenna system.

10. The wireless system of claim 1, wherein the antenna system is a dual band antenna including a substrate, wherein a first antenna is formed on a first side of the substrate, wherein a second antenna is formed on a second side of the substrate, and wherein the first antenna and the second antenna operate at different non-overlapping frequencies.

11. The wireless system of claim 1, wherein an electronic circuitry includes an IMU to support position location.

12. The wireless system of claim 1, wherein an electronic circuitry of the first wireless device includes a radio frequency to DC radio rectifier circuit, an energy storage device, and a DC-DC converter.

13. The wireless system of claim 1, wherein the first wireless device is configured to provide audio, and wherein the second wireless device is a cell phone.

14. The wireless system of claim 1, wherein the first wireless device includes one or more sensors configured to measure one or more parameters, and wherein the one or more parameters are transmitted to the second wireless device.

15. A wireless system comprising:

a first wireless device configured to operate with less than 15 milliamperes of current and which includes an antenna system; and a second wireless device having a power source, wherein the second wireless device is configured to transmit one or more radio frequency signals to the first wireless device, wherein the antenna system of the first wireless device is configured to receive the one or more radio frequency signals from the second wireless device, wherein the first wireless device is configured to harvest energy from the one or more radio frequency signals, and wherein the first wireless device is enabled for operation after a predetermined amount of energy is harvested from the one or more radio frequency signals.

16. The wireless system of claim 15, wherein the first wireless device is configured to employ a communication protocol that dynamically modulates the transmit power of the second wireless device based on the energy harvested from the one or more radio frequency signals.

17. The wireless system of claim 15, wherein the first wireless device comprises a radio frequency to DC rectifier, an energy storage device, and a DC-DC converter.

18. A wireless system comprising:

a first wireless device configured to operate with less than or equal to 10 milliamperes of current harvested from one or more radio frequency signals, wherein the first wireless device includes an antenna system, wherein the antenna system includes dual band antenna, wherein a first antenna of the antenna system is formed on a first side of a substrate, wherein a second antenna of the antenna system is formed on a second side of the substrate, wherein the first antenna and the second antenna operate at different non-overlapping frequencies;

wherein the antenna system of the first wireless device is configured to receive one or more radio frequency signals and harvest energy from the one or more radio frequency signals.

19. The wireless system of claim 18, wherein the first wireless device is configured to modulate power of the one or more radio frequency signals depending on a distance between the first wireless device and a source of the one or more radio frequency signals, wherein the first wireless device is enabled after a predetermined amount of energy is harvested from the one or more radio frequency signals, wherein the first wireless device is configured to store the harvested energy on a super capacitor.

20. The wireless system of claim 18, wherein electronic circuitry of the first wireless device includes a radio frequency to DC radio rectifier circuit, an energy storage device, and a DC-DC converter, and wherein a conductor of the first antenna overlies a conductor of the second antenna 50 percent or less.

* * * * *